(12) United States Patent
Cresina et al.

(10) Patent No.: US 10,595,901 B2
(45) Date of Patent: Mar. 24, 2020

(54) RATCHETING STRUT

(71) Applicant: Biomet Manufacturing, LLC, Warsaw, IN (US)

(72) Inventors: Jeffery Cresina, Middlesex, NJ (US); Mark Lester, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 86 days.

(21) Appl. No.: 15/817,781

(22) Filed: Nov. 20, 2017

(65) Prior Publication Data

US 2018/0132898 A1    May 17, 2018

Related U.S. Application Data

(60) Division of application No. 13/826,735, filed on Mar. 14, 2013, now Pat. No. 9,820,776, which is a continuation-in-part of application No. 13/464,502, filed on May 4, 2012, now Pat. No. 9,474,552.

(51) Int. Cl.
*A61B 17/64* (2006.01)
*A61B 17/66* (2006.01)

(52) U.S. Cl.
CPC .......... *A61B 17/6416* (2013.01); *A61B 17/66* (2013.01)

(58) Field of Classification Search
CPC . A61B 17/6416; A61B 17/64; A61B 17/7014; A61B 17/7025; A61B 17/7216; A61B 17/7225; A61B 17/66
See application file for complete search history.

(56) References Cited

U.S. PATENT DOCUMENTS

| | | |
|---|---|---|
| 2,238,869 A | 4/1941 | Haynes |
| 4,308,863 A | 1/1982 | Fischer |
| 5,601,551 A | 2/1997 | Taylor et al. |
| 5,725,526 A | 3/1998 | Allard et al. |
| 6,451,019 B1 * | 9/2002 | Zucherman ........ A61B 17/7062 606/249 |
| 8,439,914 B2 | 5/2013 | Ross et al. |

(Continued)

FOREIGN PATENT DOCUMENTS

| | | |
|---|---|---|
| WO | WO-0053109 A1 | 9/2000 |
| WO | WO-2006126167 A2 | 11/2006 |
| WO | WO-2009102904 A1 | 8/2009 |

OTHER PUBLICATIONS

"U.S. Appl. No. 13/464,502, Examiner Interview Summary dated Feb. 23, 2015", 2 pgs.

(Continued)

*Primary Examiner* — Julianna N Harvey
(74) *Attorney, Agent, or Firm* — Schwegman Lundberg & Woessner, P.A.

(57) ABSTRACT

A ratcheting strut comprising: (a) a ratchet box including a through passage; (b) a first tube sized to extend at least partially through the passage, the first tube including teeth that engage corresponding teeth of the ratchet box; (c) a second tube mounted to the ratchet box in parallel with the first tube, the second tube operatively coupled to a second fixation adapter; and, (d) a threaded rod operatively coupled to a nut and a first fixation adapter, the threaded rod repositionably mounted to the first tube, where the nut is operatively coupled and repositionable with respect to the first tube.

15 Claims, 54 Drawing Sheets

(56) References Cited

U.S. PATENT DOCUMENTS

| | | |
|---|---|---|
| 9,474,552 B2 | 10/2016 | Barnett et al. |
| 9,820,776 B2 | 11/2017 | Cresina et al. |
| 2002/0193666 A1 | 12/2002 | Sherts et al. |
| 2003/0149378 A1* | 8/2003 | Peabody .............. A61B 5/1072 600/587 |
| 2006/0195087 A1 | 8/2006 | Sacher et al. |
| 2006/0217735 A1 | 9/2006 | MacDonald et al. |
| 2009/0216231 A1 | 8/2009 | Lanz |
| 2010/0312243 A1* | 12/2010 | Ross ...................... A61B 17/62 606/56 |
| 2011/0137347 A1 | 6/2011 | Hunziker |
| 2011/0208187 A1 | 8/2011 | Wong |
| 2012/0203225 A1 | 8/2012 | Mingozzi et al. |
| 2013/0296857 A1 | 11/2013 | Barnett et al. |
| 2014/0276822 A1 | 9/2014 | Cresina et al. |
| 2017/0150994 A9 | 6/2017 | Cresina et al. |

OTHER PUBLICATIONS

"U.S. Appl. No. 13/464,502, Final Office Action dated Nov. 4, 2015", 11 pgs.

"U.S. Appl. No. 13/464,502, Non Final Office Action dated Mar. 4, 2015", 10 pgs.

"U.S. Appl. No. 13/464,502, Notice of Allowance dated Jun. 21, 2016", 7 pgs.

"U.S. Appl. No. 13/464,502, Preliminary Amendment filed May 4, 2012", 4 pgs.

"U.S. Appl. No. 13/464,502, Response filed May 3, 2016 to Final Office Action dated Nov. 4, 2015", 8 pgs.

"U.S. Appl. No. 13/464,502, Response filed Aug. 3, 2015 to Non Final Office Action dated Mar. 4, 2015", 9 pgs.

"U.S. Appl. No. 13/464,502, Response filed Oct. 15, 2014 to Restriction Requirement dated Oct. 1, 2014", 4 pgs.

"U.S. Appl. No. 13/464,502, Restriction Requirement dated Oct. 1, 2014", 8 pgs.

"U.S. Appl. No. 13/826,735, Examiner Interview Summary dated May 23, 2017", 3 pgs.

"U.S. Appl. No. 13/826,735, Final Office Action dated Jan. 29, 2016", 11 pgs.

"U.S. Appl. No. 13/826,735, Non Final Office Action dated Mar. 22, 2017", 17 pgs.

"U.S. Appl. No. 13/826,735, Non Final Office Action dated Aug. 11, 2015", 13 pgs.

"U.S. Appl. No. 13/826,735, Notice of Allowance dated Jul. 21, 2017", 7 pgs.

"U.S. Appl. No. 13/826,735, Notice of Allowance dated Aug. 17, 2016", 7 pgs.

"U.S. Appl. No. 13/826,735, Response filed Apr. 29, 2016 to Final Office Action dated Jan. 29, 2016", 12 pgs.

"U.S. Appl. No. 13/826,735, Response filed May 26, 2017 to Non Final Office Action dated Mar. 22, 2017", 10 pgs.

"U.S. Appl. No. 13/826,735, Response filed Oct. 15, 2014 to Restriction Requirement dated Sep. 16, 2014", 11 pgs.

"U.S. Appl. No. 13/826,735, Response filed Nov. 11, 2015 to Non Final Office Action dated Aug. 11, 2015", 10 pgs.

"U.S. Appl. No. 13/826,735, Restriction Requirement dated Sep. 16, 2014", 9 pgs.

"European Application Serial No. 13714106.5, Response filed Jun. 29, 2015 to Communication pursuant to Rules 161(1) and 162 EPC dated Dec. 19, 2014", 28 pgs.

"European Application Serial No. 13714106.5, Response filed Aug. 16, 2017 to Office Action dated Apr. 7, 2017", 41pgs.

"International Application Serial No. PCT/US2013/031539, International Search Report dated Jun. 28, 2013", 6 pgs.

"International Application Serial No. PCT/US2013/031539, Written Opinion dated Jun. 28, 2013", 7 pgs.

* cited by examiner

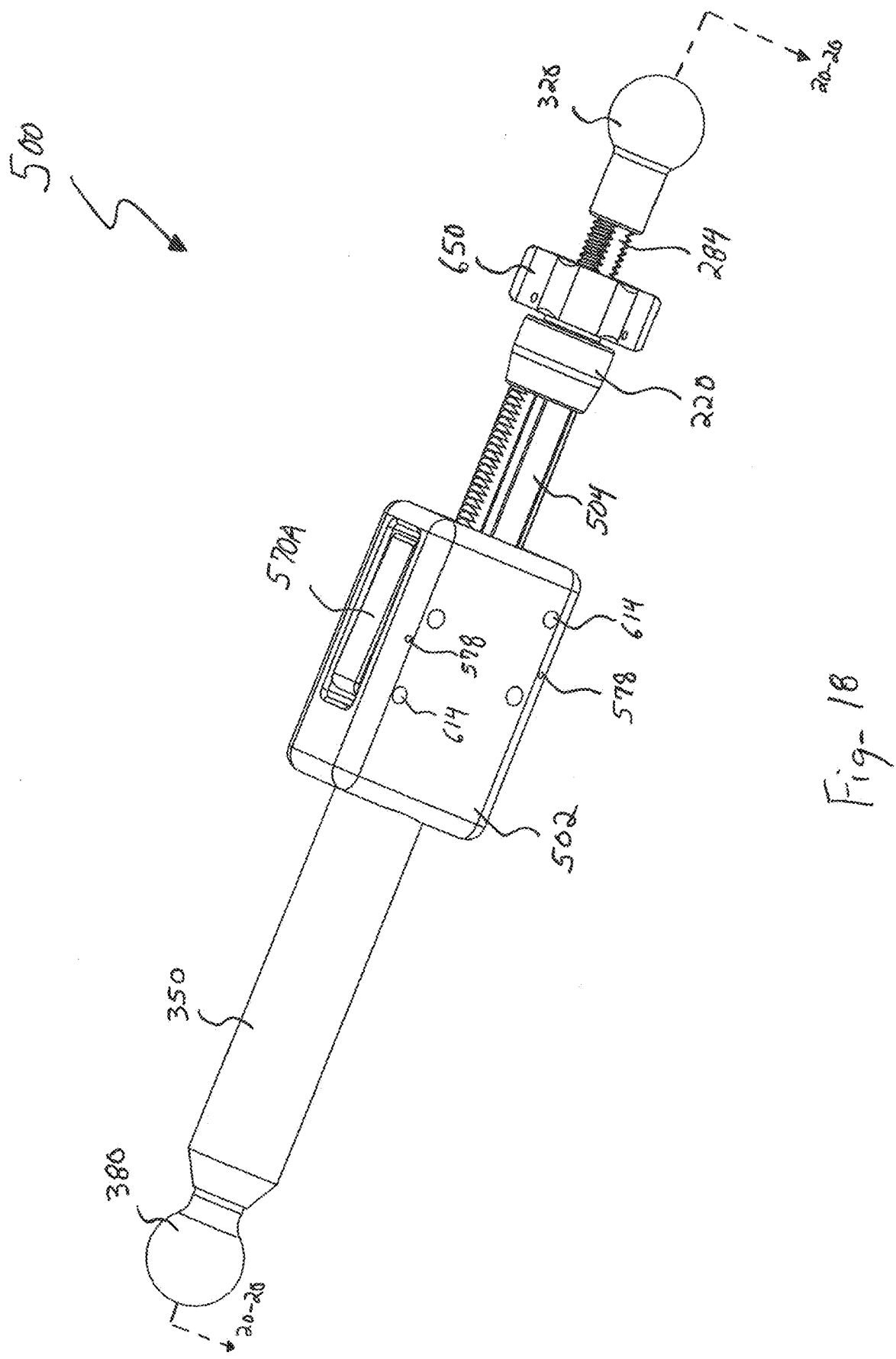

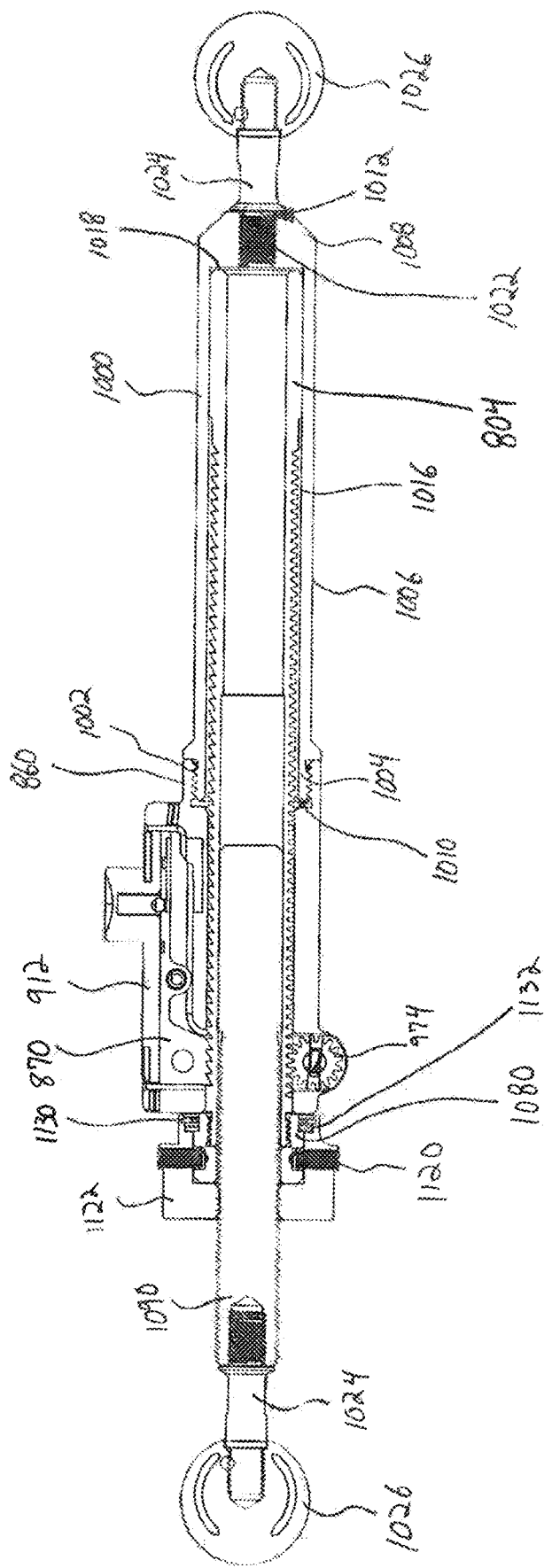

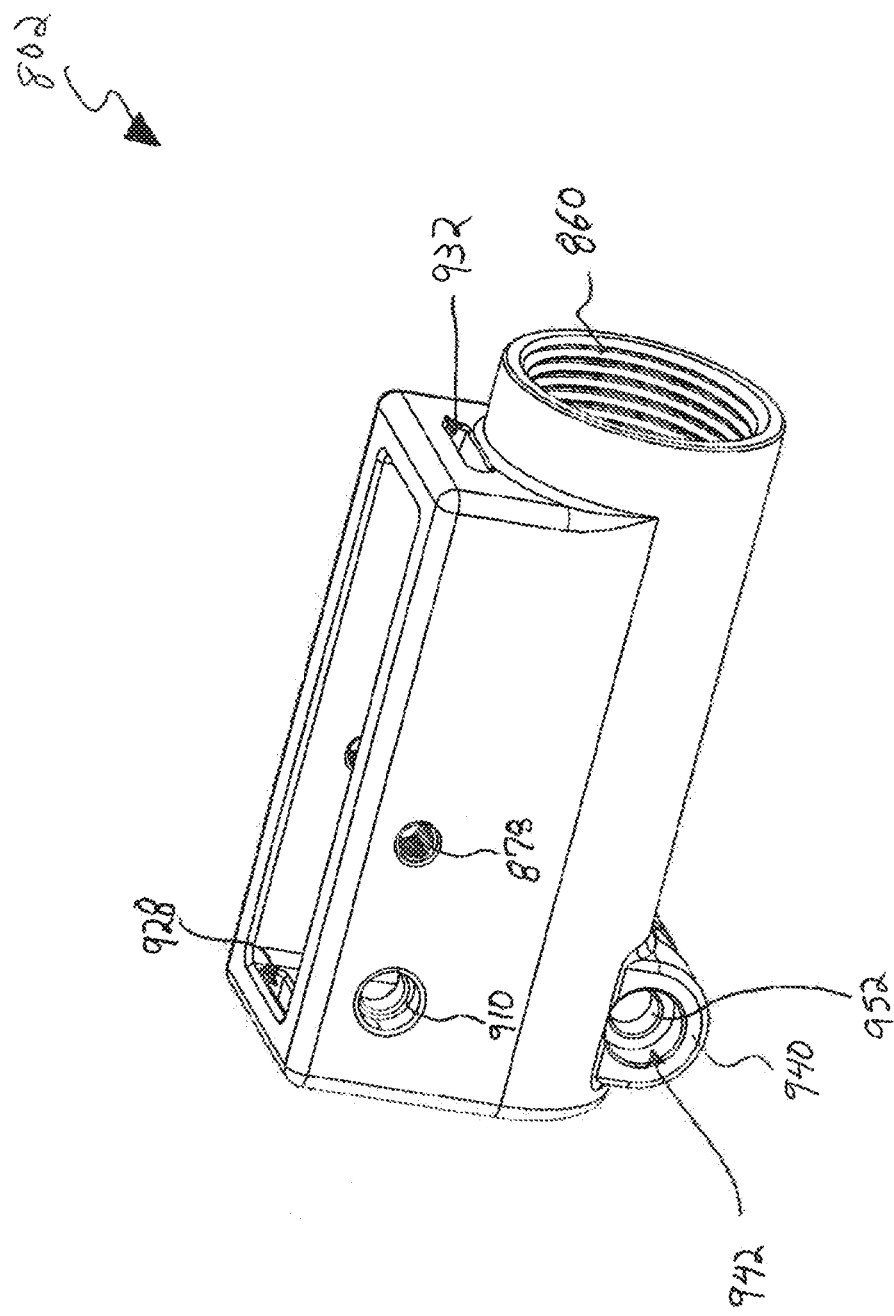

RATCHETING STRUT

CROSS REFERENCE TO RELATED APPLICATIONS

This application is a divisional application of U.S. patent application Ser. No. 13/826,735, filed Mar. 14, 2013, which application is a continuation-in-part of U.S. patent application Ser. No. 13/464,502, filed May 4, 2012, issued Oct. 25, 2016 as U.S. Pat. No. 9,474,552 and titled "RATCHETING STRUT," the disclosures of which are incorporated herein by reference in their entireties.

RELATED ART

Field of the Invention

The present invention is directed to devices and methods utilized in fracture reduction and, more specifically, to devices and methods providing length adjustment during fracture fixation.

INTRODUCTION TO THE INVENTION

The present invention is directed to devices and methods utilized in fracture reduction and, more specifically, to devices and methods providing length adjustment during fracture fixation. The present invention may include modular (re)movable struts that can be interchanged depending upon the distance to be spanned (i.e., span fracture in a single long bone, or cross the knee joint). In one exemplary embodiment, a ratcheting strut is disclosed that provides for length adjustment during fracture fixation and reduction.

It is a first aspect of the present invention to provide a ratcheting strut comprising: (a) a ratchet box including a through passage; (b) a first tube sized to extend at least partially through the passage, the first tube including teeth that engage corresponding teeth associated with the ratchet box; (c) a second tube mounted to the ratchet box in parallel with the first tube, the second tube operatively coupled to a second fixation adapter; and, (d) a threaded rod operatively coupled to a nut and a first fixation adapter, the threaded rod repositionably mounted to the first tube, where the nut is operatively coupled and repositionable with respect to the first tube.

In a more detailed embodiment of the first aspect, the first tube, the second tube, and the threaded rod are coaxial, in yet another more detailed embodiment, the second tube includes a fixed length and is removably coupled to the ratchet box. In a further detailed embodiment, the second tube is removably mounted to the ratchet box, and the second fixation adapter is removably mounted to the second tube. In still a further detailed embodiment, the first fixation adapter includes at least one of a ball, a ball joint, a ball joint housing, a ball joint cap, a halo subassembly, and a clamp subassembly. In a more detailed embodiment, the ratchet box includes a first lever repositionable between an engaged position and a disengaged position, the first lever includes teeth, the teeth of the first lever engage the ratchet of the first tube in the engaged position, and the teeth of the first lever do not engage the teeth of the first tube in the disengaged position. In a more detailed embodiment, a plurality of the teeth of the first lever comprise ratchet teeth each including a profile including an inclined surface and a vertical surface, a plurality of the teeth of the first tube comprise ratchet teeth each including a profile including an inclined surface and a vertical surface, the inclined surfaces of the ratchet teeth of the first lever are substantially parallel to the inclined surfaces of the ratchet teeth of the first tube when in the engaged position, and the vertical surfaces of the ratchet teeth of the first lever are substantially parallel to the vertical surfaces of the ratchet teeth of the first tube when in the engaged position. In another more detailed embodiment, the ratchet box includes a first biased lever repositionable between an engaged position and a disengaged position, the first biased lever includes the teeth that are associated with the ratchet box, the lever is configured to be selectively locked in at least one of the engaged position and the disengaged position, the teeth of the first biased lever engage the teeth of the first tube in the engaged position, and the teeth of the first biased lever do not engage the teeth of the first tube in the disengaged position. In yet another more detailed embodiment, the ratchet box includes a first biased lever repositionable between an engaged position and a disengaged position, the first biased lever includes the teeth that are associated with the ratchet box, the engaged position may be at least one of an engaged locked position and an engaged neutral position, the lever is configured to be selectively secured in at least one of the engaged locked position, the engaged neutral position, and the disengaged position, the lever is repositionable in the engaged neutral position to allow repositioning of the first tube with respect to the ratchet box, the lever is not repositionable in the engaged locked position to disallow repositioning of the first tube with respect to the ratchet box, the teeth of the first biased lever engage the teeth of the first tube in the engaged locked position and the engaged neutral position, and the teeth of the first biased lever do not engage the teeth of the first tube in the disengaged position. In still another more detailed embodiment, the ratchet box includes a first lever repositionable between an engaged position and a disengaged position, the ratchet box also including a repositionable gear, the first lever includes the teeth that are associated with the ratchet box, wherein the teeth of the first lever are ratchet teeth, the teeth of the ratchet tube include a first row and a second row, wherein at least one the first row includes ratchet teeth, the ratchet teeth of the first lever engage at least one of the first row of the ratchet teeth of the first tube in the engaged position, the gear is configured to engage the second row of the teeth of the first tube, and the ratchet teeth of the first lever do not engage the first row of the ratchet teeth of the first tube in the disengaged position.

In yet another more detailed embodiment of the first aspect, the teeth of the first lever and the ratchet tube each include a profile including an inclined surface and a vertical surface, the inclined surfaces of the teeth are parallel to one another in the engaged position, and the vertical surfaces of the teeth are parallel to one another in the engaged position. In still another more detailed embodiment, the ratchet box includes a gear that includes the teeth that are associated with the ratchet box, the teeth of the gear configured to engage the teeth of the first tube, and the gear is configured to reposition the first tube upon rotation of the gear. In a further detailed embodiment, the gear is operatively coupled to a ratchet that allows repositioning of the first tube in a first direction and disallows repositioning of the first tube in a second direction that is opposite the first direction. In still a further detailed embodiment, the ratchet includes a first catch repositionable between a first position and a second position, the first position allows repositioning of the first tube in the first direction, the second position allows repositioning of the first tube in the second direction. In a more detailed embodiment, the first catch includes a repositionable lever having ratchet teeth, the first tube includes ratchet teeth, the ratchet teeth of the repositionable lever engage the ratchet teeth of the first tube in the first position, and the ratchet teeth of the repositionable lever disengage the ratchet teeth of the first tube in the second position. In a more detailed embodiment, the second tube is at least partially hollow and includes a cavity adapted to be partially occupied by the first tube, and the first tube is at least partially hollow and includes a cavity adapted to be partially occupied by the threaded rod. In another more detailed embodiment, the first tube, the second tube, and the threaded rod telescopically interact with one another. In yet another more detailed embodiment, the threaded rod is removably mounted to the second fixation adapter, and the fixation adapter includes at least one of a ball, a ball joint, a ball joint housing, a ball joint cap, a halo subassembly, and a clamp subassembly.

In a more detailed embodiment of the first aspect, the first tube is operatively coupled to a tube mount having a tube mount orifice, the tube mount is operatively coupled to the nut, the tube mount orifice is sized to allow throughput of the threaded rod and disallow throughput of the first tube, and threads of the threaded rod are configured to engage threads of the nut so that rotation of the nut results in longitudinal repositioning of the threaded rod with respect to the nut, the first tube, and the tube mount. In yet another more detailed embodiment, the nut is rotationally mounted to the tube mount, and a washer interposes the nut and the tube mount. In a further detailed embodiment, the washer includes a wave washer and a flat washer. In still a further detailed embodiment, a ratchet box includes a repositionable button, the repositionable button is operatively coupled to a ratchet arm, and the ratchet arm is configured to engage the first tube. In a more detailed embodiment, the repositionable button is repositionable among a first locked position and a neutral position, the first locked position inhibits the ratchet arm from disengaging a first set of teeth of the first tube and inhibits repositioning the first tube with respect to the ratchet arm, and the neutral position biases the ratchet arm into engagement with the first set of teeth of the first tube but allows repositioning of the first tube with respect to the ratchet arm in a first direction. In a more detailed embodiment, the repositionable button is repositionable among a second locked position, the second locked position allows the ratchet arm to disengage the first set of teeth of the first tube and allows repositioning of the first tube with respect to the ratchet arm in a second direction and the first direction, where the second direction is opposite the first direction.

It is a second aspect of the present invention to provide a bone fracture fixation device comprising a first tube being repositionable with respect to a second tube in predetermined longitudinal increments, wherein the first tube is associated with a gear configured to engage the second tube to reposition the first tube with respect to the second tube in a first direction or a second direction opposite the first direction, where at least one of the first tube and the second tube includes an extension operatively coupled thereto that is repositionable to increase an aggregate length of at least one of the first tube and the second tube, wherein the extension is repositionable in longitudinal increments smaller than the predetermined longitudinal increments.

In a more detailed embodiment of the second aspect, the longitudinal increments of the extension are infinitely small. In yet another more detailed embodiment, the first tube, the second tube, and the extension are coaxial with one another. In a further detailed embodiment, the first tube and the second tube each include a fixed length, and the first tube includes a hollow interior to accommodate at least a portion of the second tube. In still a further detailed embodiment, the invention includes a first lever configured to engage the second tube and repositionable between an engaged position and a disengaged position, the first lever includes ratchet teeth, the ratchet teeth of the first lever engage ratchet teeth of the second tube in the engaged position, and the ratchet teeth of the first lever do not engage the ratchet teeth of the second tube in the disengaged position. In a more detailed embodiment, the invention further includes a repositionable button operatively coupled to the first lever, the repositionable button repositionable among a locked open position, a locked closed position, and a neutral position, the locked open position locks the ratchet teeth of the first lever in the disengaged position and locks an overall position of the first lever, the locked closed position locks the ratchet teeth of the first lever in the engaged position and locks an overall position of the first lever, and the neutral position locks the ratchet teeth of the first lever in the engaged position but unlocks the overall position of the first lever. In a more detailed embodiment, the ratchet teeth of the first lever each include a profile including an inclined surface and a vertical surface, the ratchet teeth of the second tube each include a profile including an inclined surface and a vertical surface, the inclined surfaces of the ratchet teeth of the first lever are substantially parallel to the inclined surfaces of the ratchet teeth of the second tube when in the engaged position, and the vertical surfaces of the ratchet teeth of the first lever are substantially parallel to the vertical surfaces of the ratchet teeth of the second tube when in the engaged position. In another more detailed embodiment, the first tube is at least partially hollow and includes a cavity adapted to be partially occupied by the second tube, and the second tube is at least partially hollow and includes a cavity adapted to be partially occupied by the extension. In yet another more detailed embodiment, the first tube, the second tube, and the extension telescopically interact with one another. In still another more detailed embodiment, the extension is removably mounted to a first fixation adapter, and the first fixation adapter includes at least one of a ball joint, a ball joint housing, and a ball joint cap.

In yet another more detailed embodiment of the second aspect, the second tube is operatively coupled to a tube mount having a tube mount orifice, the extension is operatively coupled to a nut, the tube mount is operatively coupled to the nut, the tube mount orifice is sized to allow throughput of the extension and disallow throughput of the second tube, and threads of the extension are configured to engage threads of the nut so that rotation of the nut results in longitudinal repositioning of the extension with respect to the nut, the second tube, and the tube mount. In still another more detailed embodiment, the nut is rotationally mounted to the tube mount, and a washer interposes the nut and the tube mount, in a further detailed embodiment, the washer includes a wave washer and a flat washer.

It is a third aspect of the present invention to provide a method of using a fracture fixation device that includes opposing longitudinal tubes that are repositionable with respect to one another to increase or decrease a total distance between opposing ends of the longitudinal tubes, the method including repositioning a first of the longitudinal tubes with respect to a second of the longitudinal tubes in a first direction by using a gear, where a first series of teeth associated with the first longitudinal tube engages the gear, and where a first blocking actuator concurrently engages the first series of teeth, where opposite ends of the longitudinal tubes are each mounted to a fracture fixation adapter In a more detailed embodiment of the third aspect, the invention further includes the step of repositioning the first blocking actuator to discontinue engagement with the first series of teeth to allow repositioning of the first longitudinal tube with respect to the second longitudinal tube in a second direction, opposite the first direction. In yet another more detailed embodiment, the step of repositioning the first blocking actuator includes locking a repositionable button in a first position. In a further detailed embodiment, the invention further includes the step of inhibiting repositioning the first longitudinal tube with respect to the second longitudinal tube in the first direction and the second direction by locking the blocking actuator in a static position, wherein the step of locking the blocking actuator in the static position includes locking the repositionable button in a second position. In still a further detailed embodiment, the step of repositioning the first longitudinal tube with respect to the second longitudinal tube includes retaining the repositionable button in a neutral position that allows repositioning of the first blocking actuator as the first longitudinal tube is repositioned with respect to the second longitudinal tube. In a more detailed embodiment, the invention further includes the step of repositioning of a first extension mounted to at least one of the first longitudinal tube and the second longitudinal tube to increase an overall length of the fracture fixation device, where the first extension, the first longitudinal tube, and the second longitudinal tube are coaxial with respect to one another.

BRIEF DESCRIPTION THE DRAWINGS

FIG. 17 is a magnified view of the ratchet box and other components shown in FIG. 3.

FIG. 18 is an elevated perspective view of an assembled second exemplary ratcheting strut in accordance with the instant disclosure.

FIG. 37 is a cross-sectional view of the exemplary ratcheting strut of FIG. 35 taken vertically and along the longitudinal axis, without the halo and clamping subassemblies.

FIG. 38 is an elevated perspective view of the exemplary ratchet box shown in FIG. 35.

FIG. 42 is a proximal, profile view of the exemplary ratchet box shown in FIG. 35.

DETAILED DESCRIPTION

Figure 1:
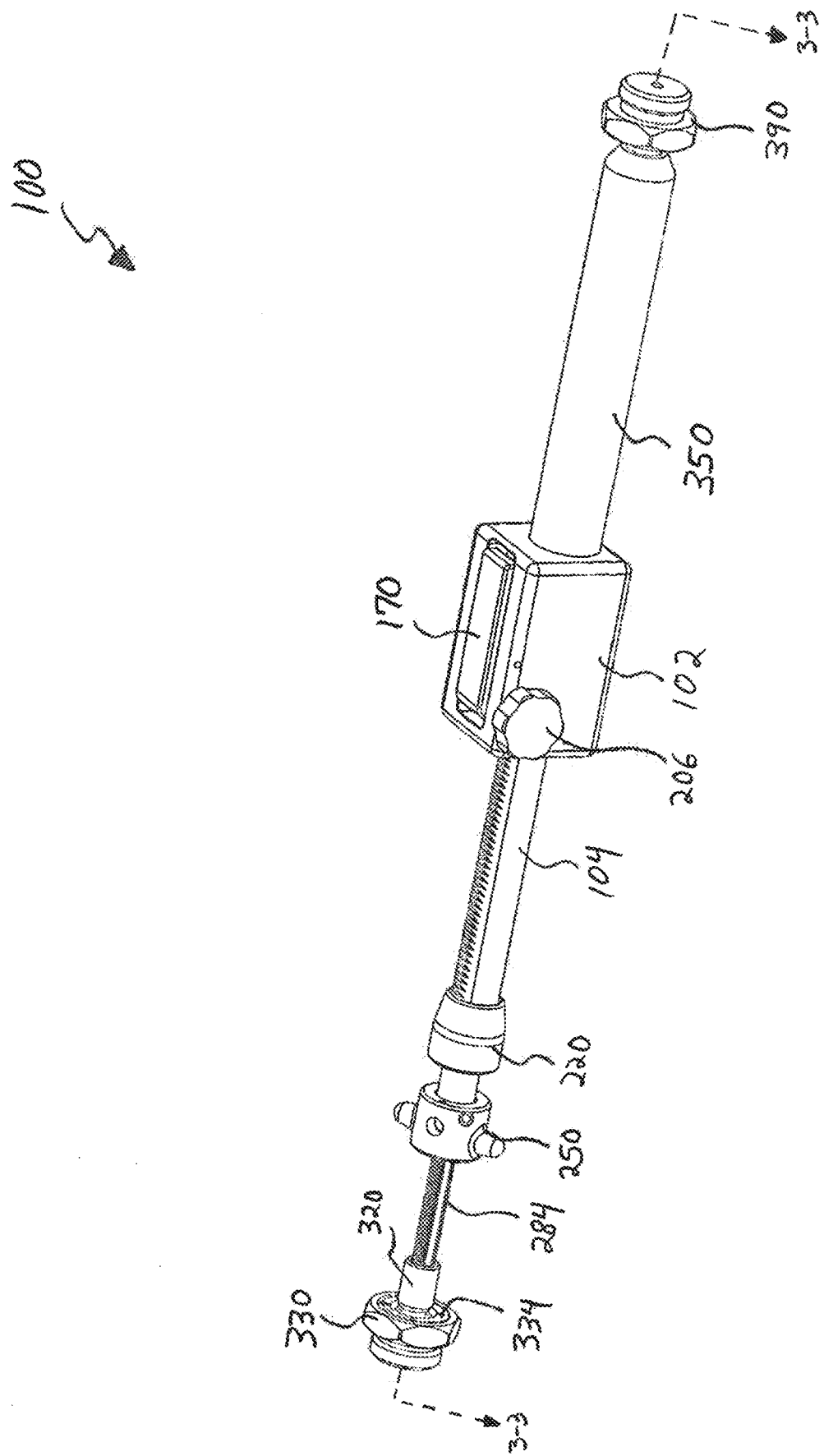
FIG. 1 is an elevated perspective view of an assembled first exemplary ratcheting strut in accordance with the instant disclosure.
Figure 2:
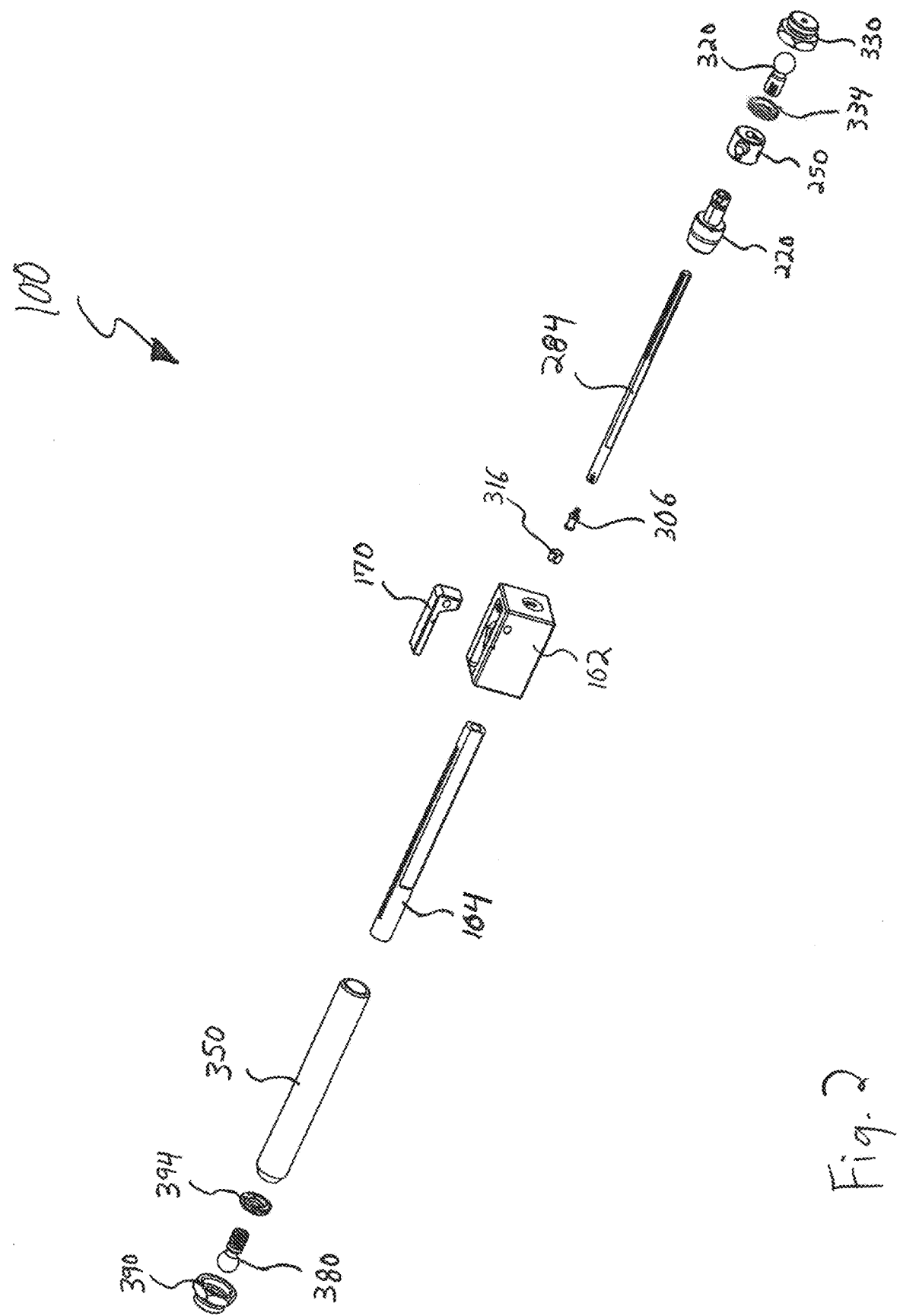
FIG. 2 is an exploded view of the first exemplary ratcheting strut of FIG. 1 without the thumb screw.
Figure 3:
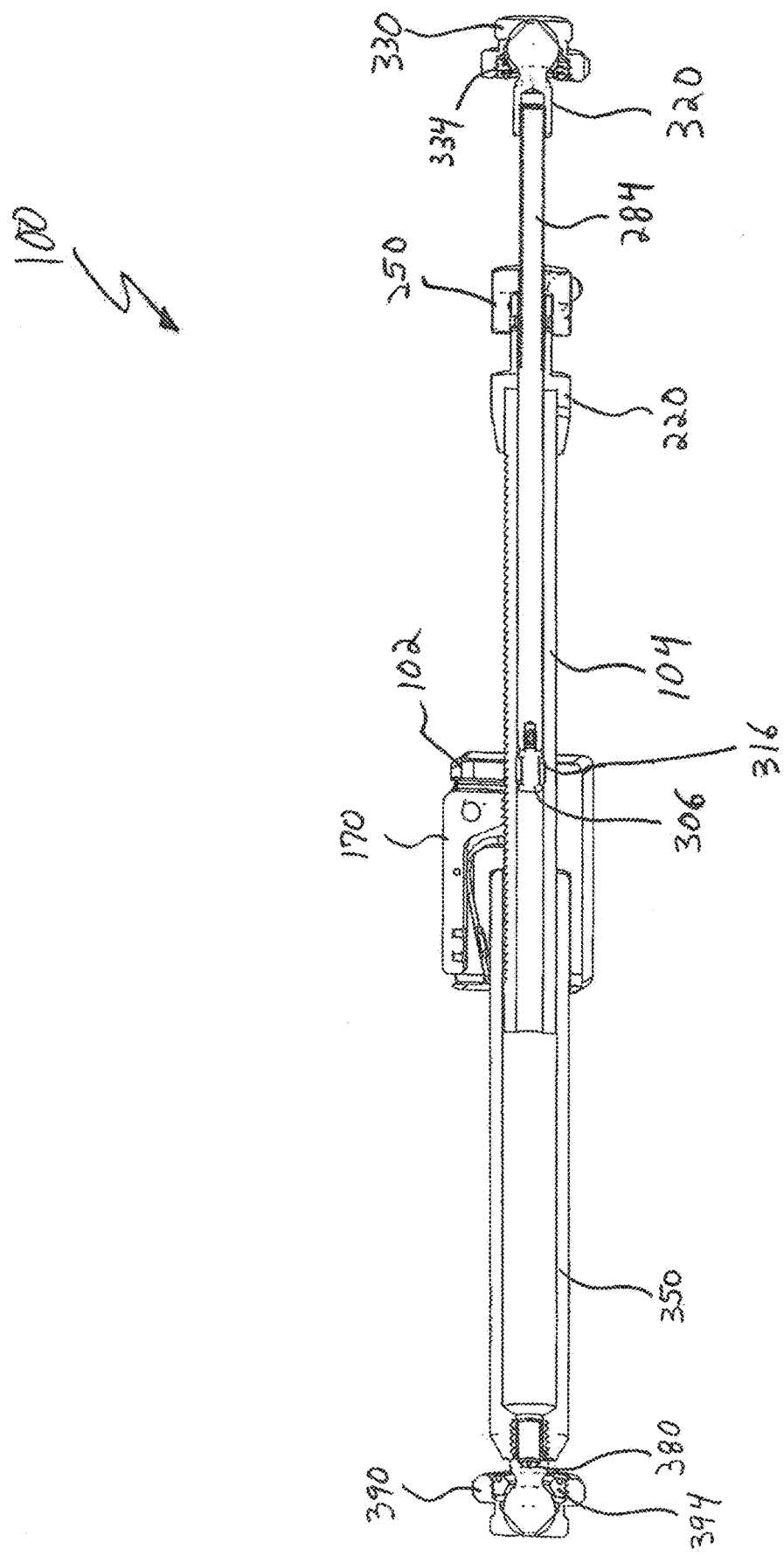
FIG. 3 is a cross-sectional view of the first exemplary ratcheting strut of FIG. 1 taken along line 3-3.
Figure 4:
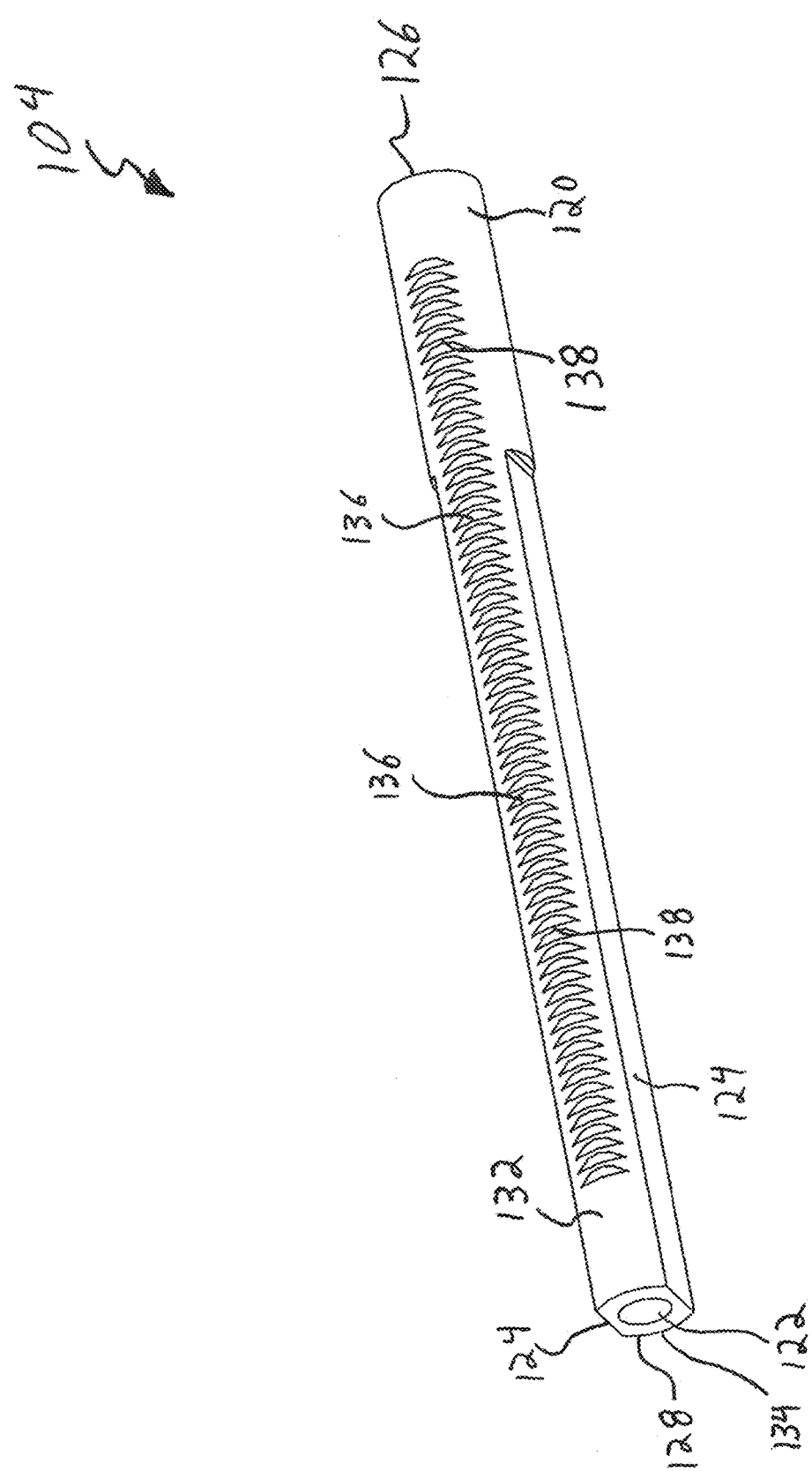
FIG. 4 is an elevated perspective view of the exemplary ratchet tube of FIG. 1.
Figure 5:
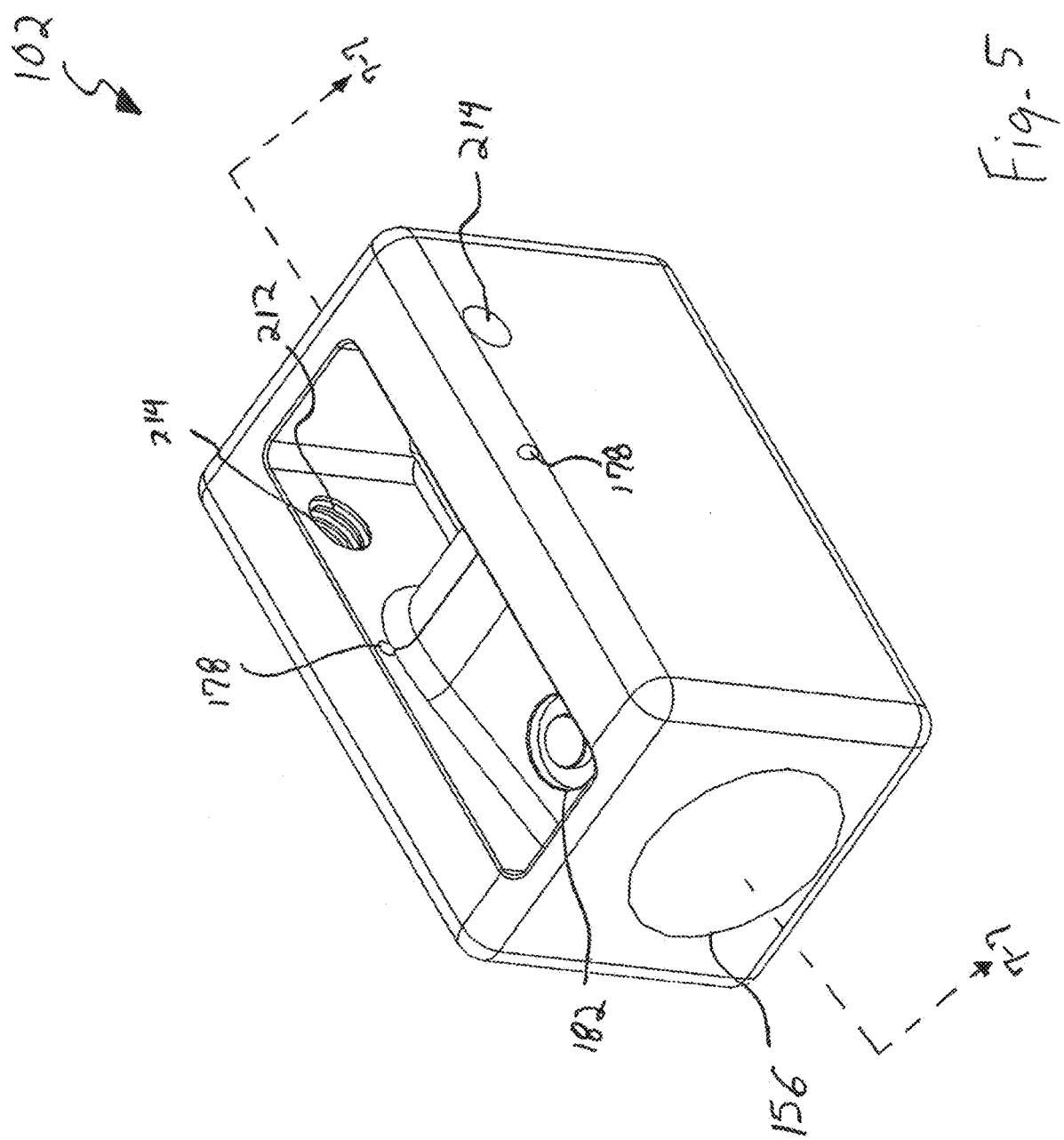
FIG. 5 is an elevated perspective view of the exemplary ratchet box of FIG. 1.
Figure 6:
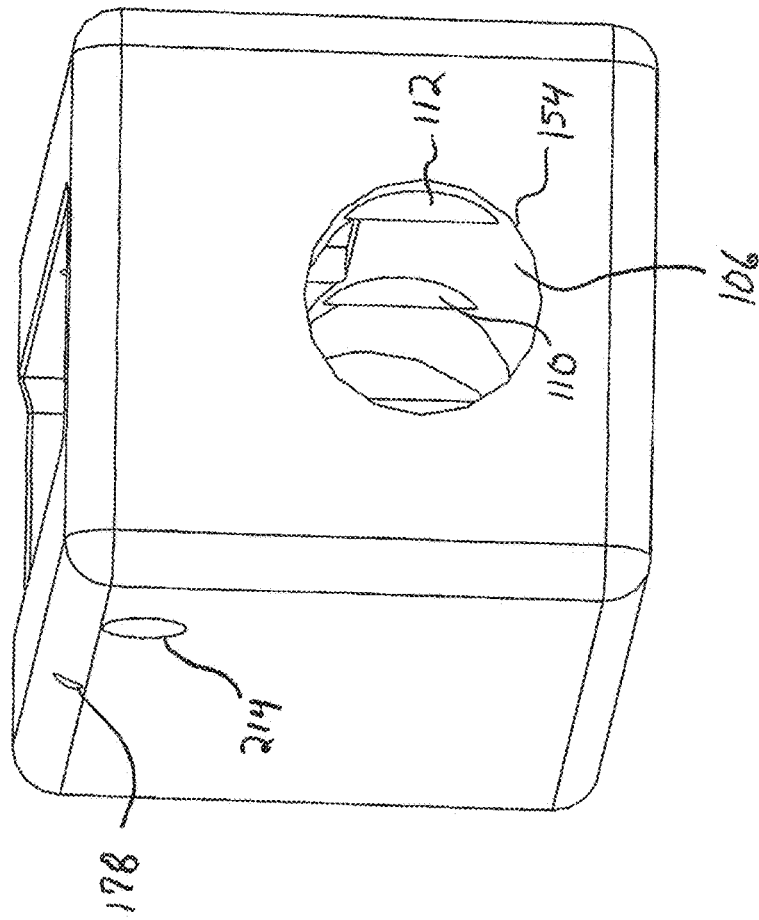
FIG. 6 is another elevated perspective view of the exemplary ratchet box of FIG.
Figure 7:
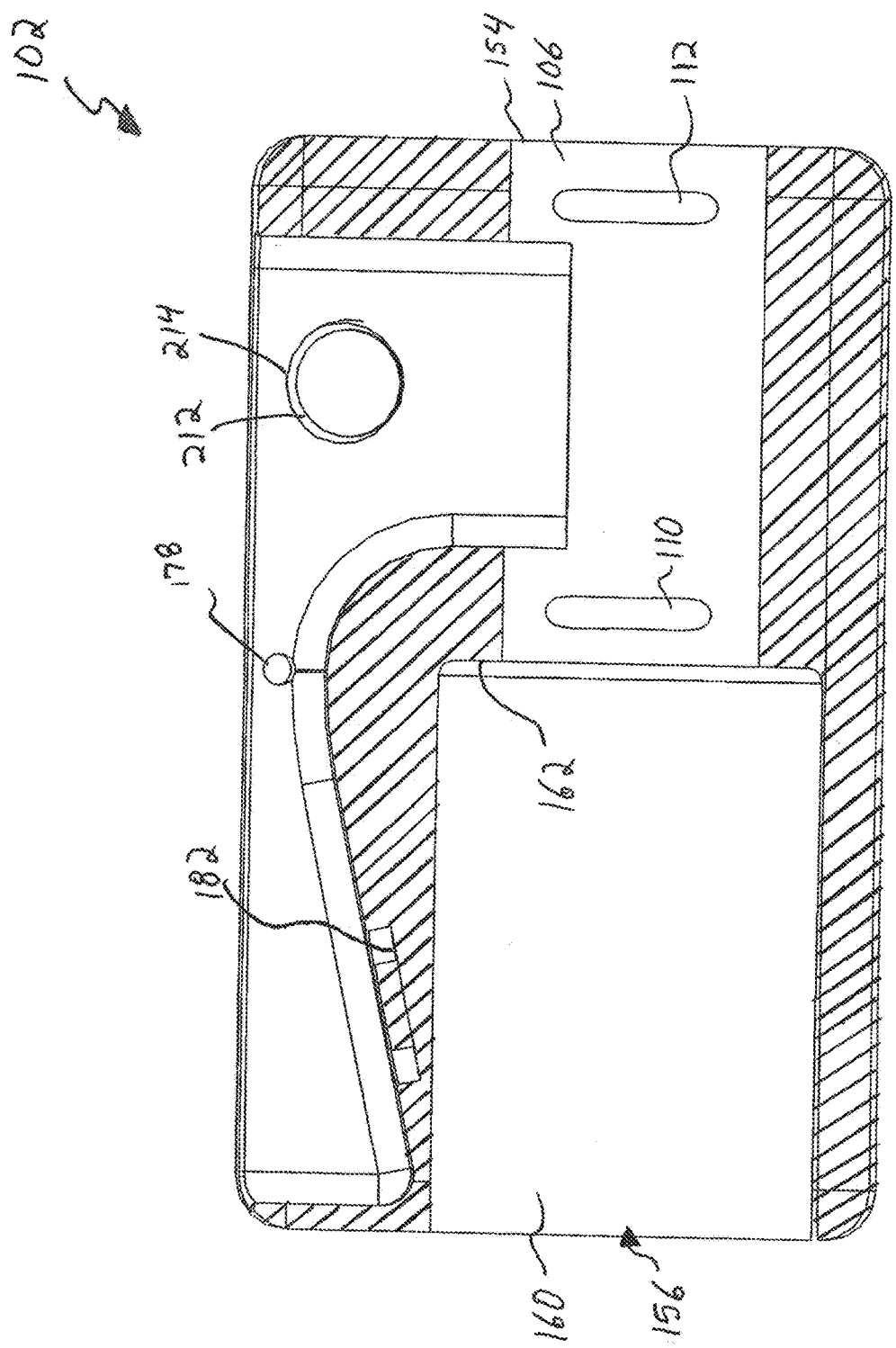
FIG. 7 is a cross-sectional view of the first exemplary ratcheting box of FIG. 5 taken along line 7-7.
Figure 8:
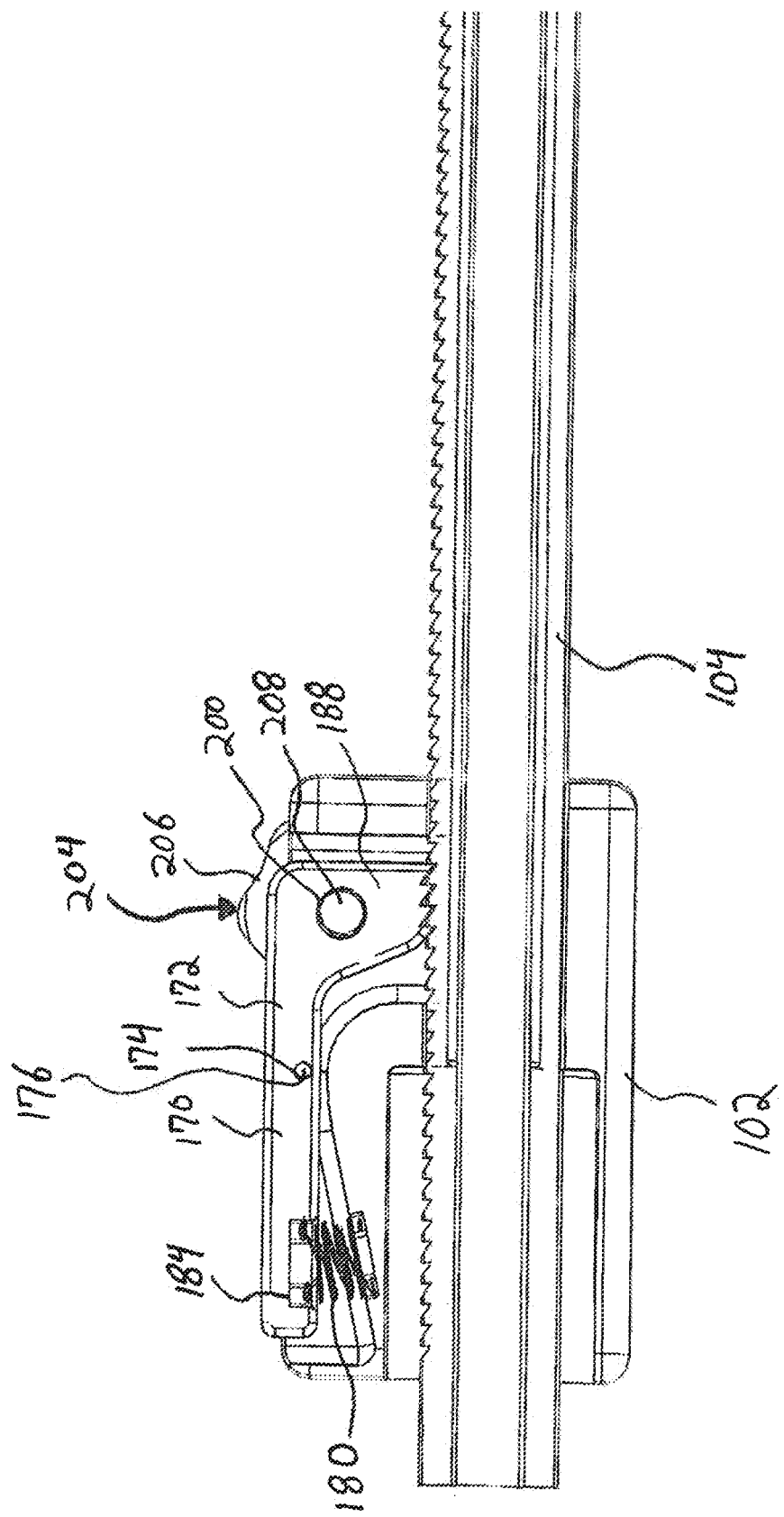
FIG. 8 is a magnified view of the ratchet box and internal components shown in FIG. 3.
Figure 9:
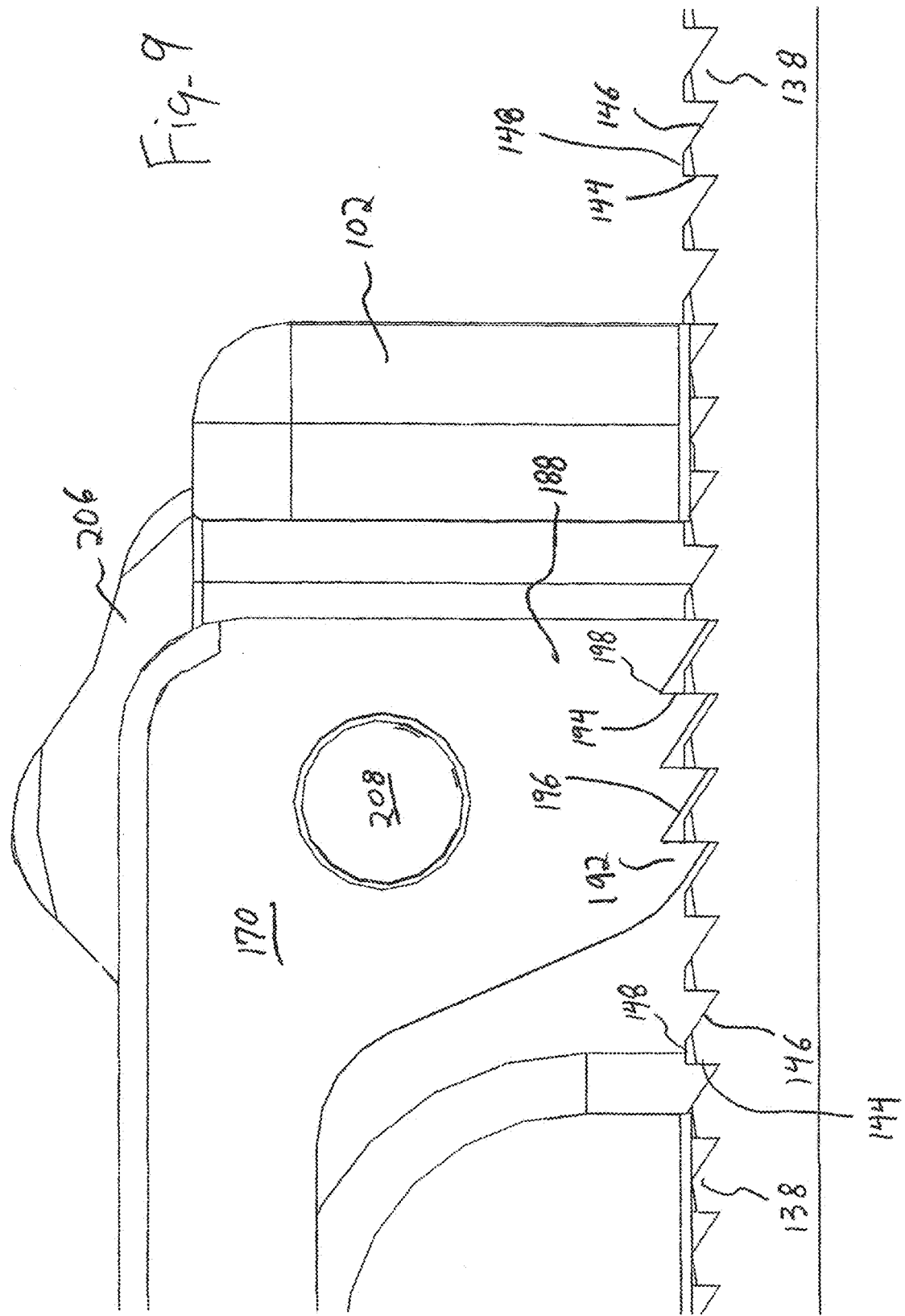
FIG. 9 is a magnified view of the ratchet box and internal components shown in FIG. 8.
Figure 10:
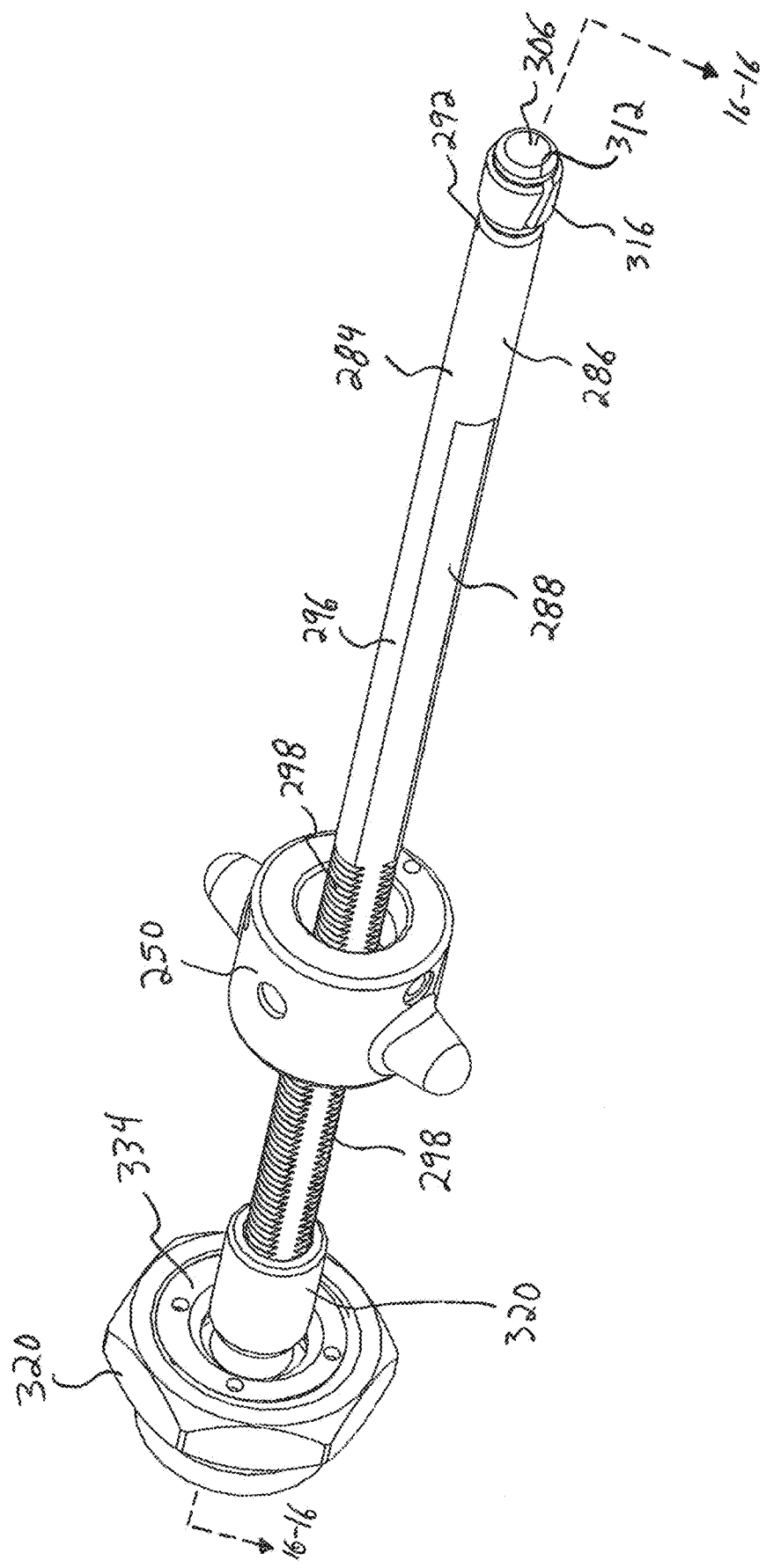
FIG. 10 is an elevated perspective view showing assembly of several of the components of FIG. 1.
Figure 11:
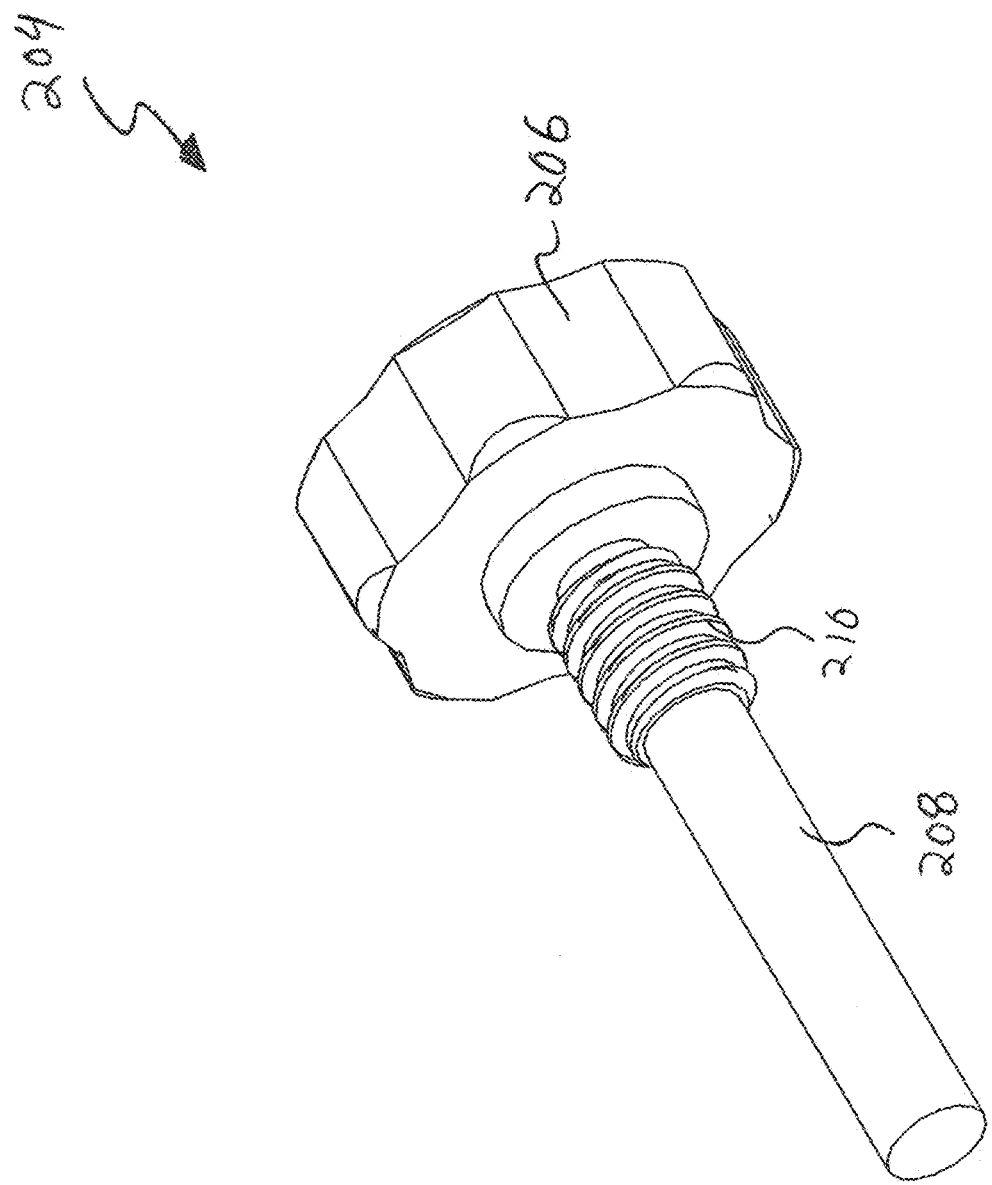
FIG. 11 is an elevated perspective view of the thumb screw in FIG. 1.
Figure 12:
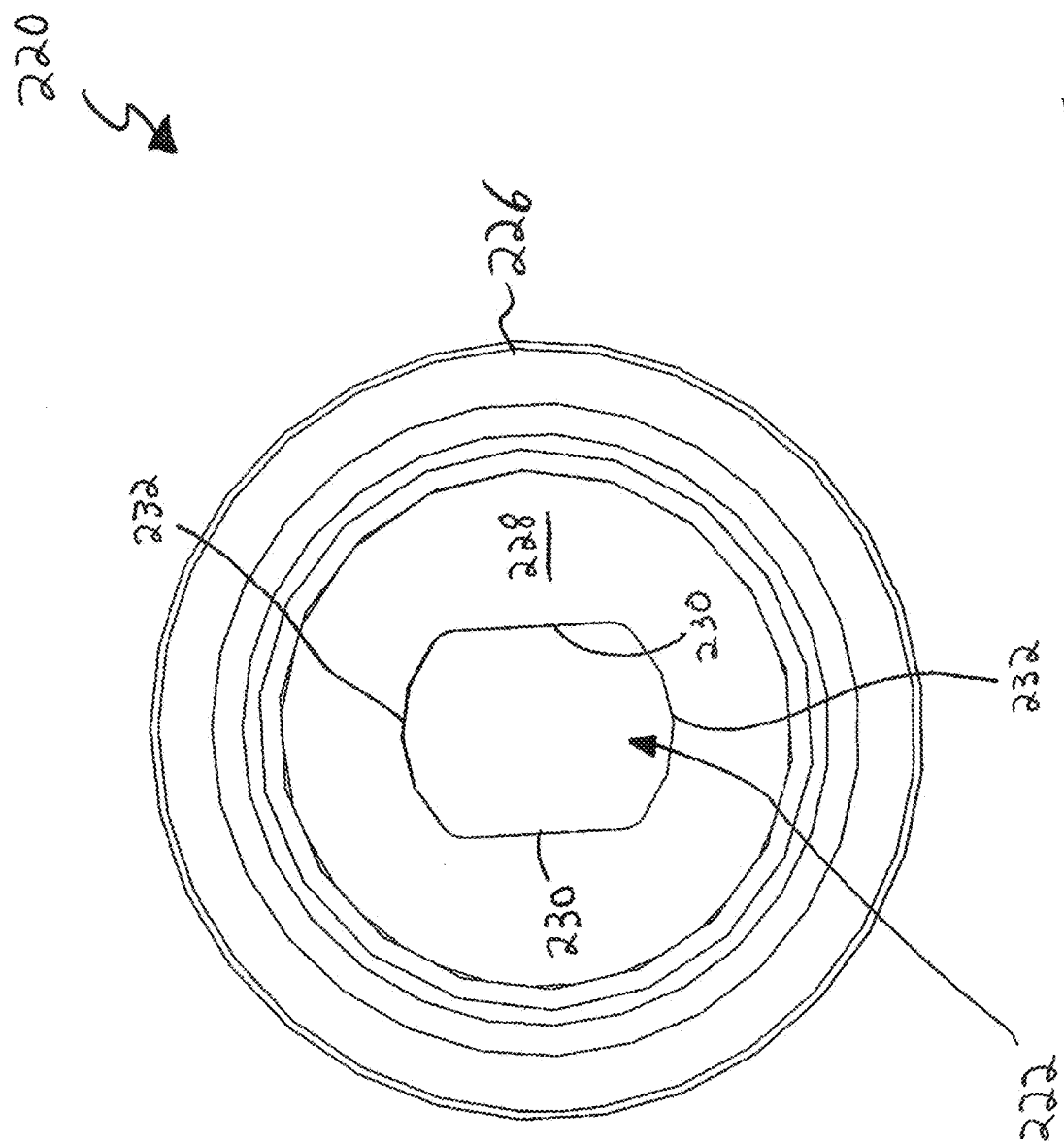
FIG. 12 is an end view of the tube mount of FIG. 1.
Figure 13:
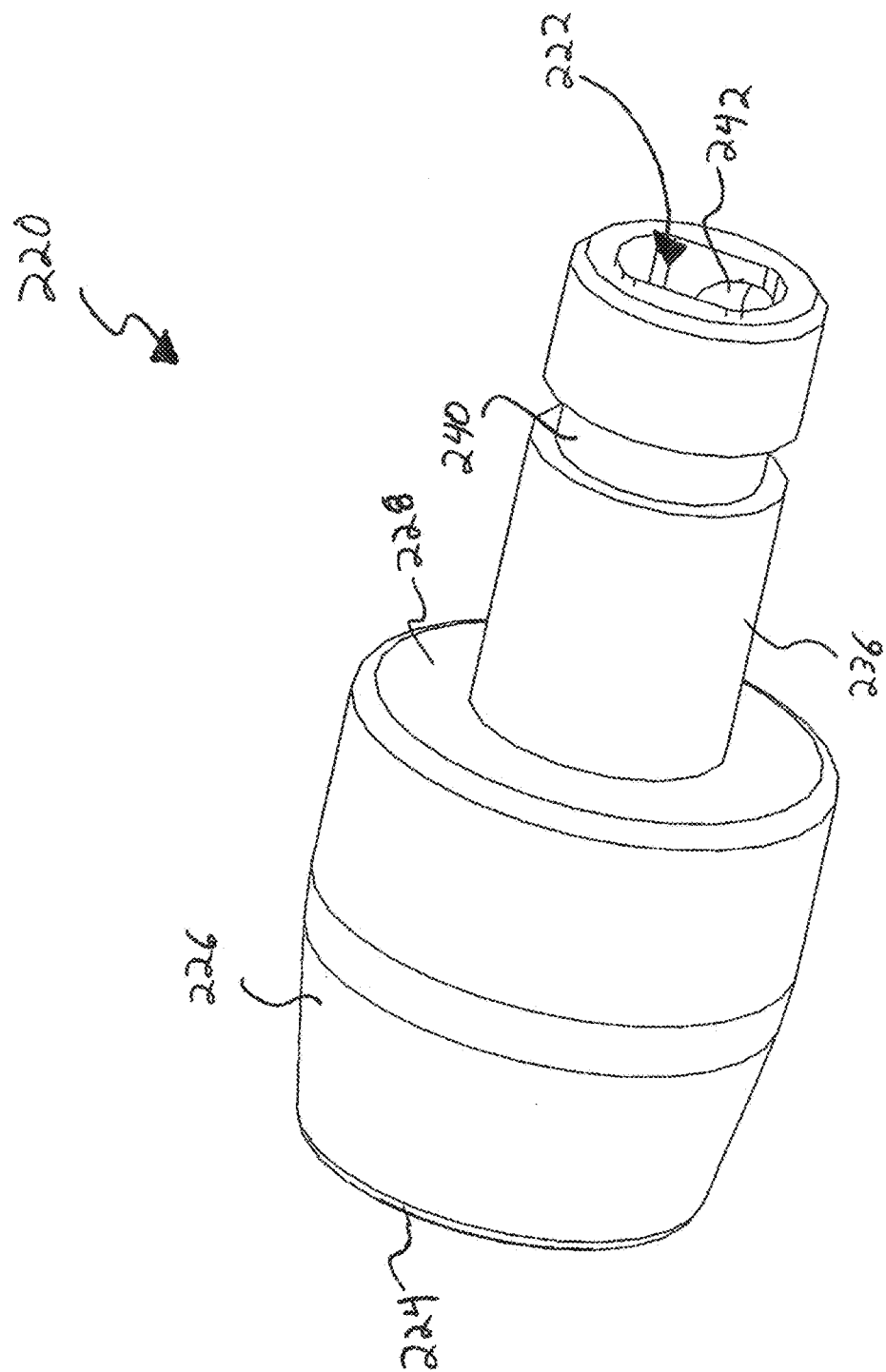
FIG. 13 is an elevated perspective view of the tube mount of FIG. 1.
Figure 14:
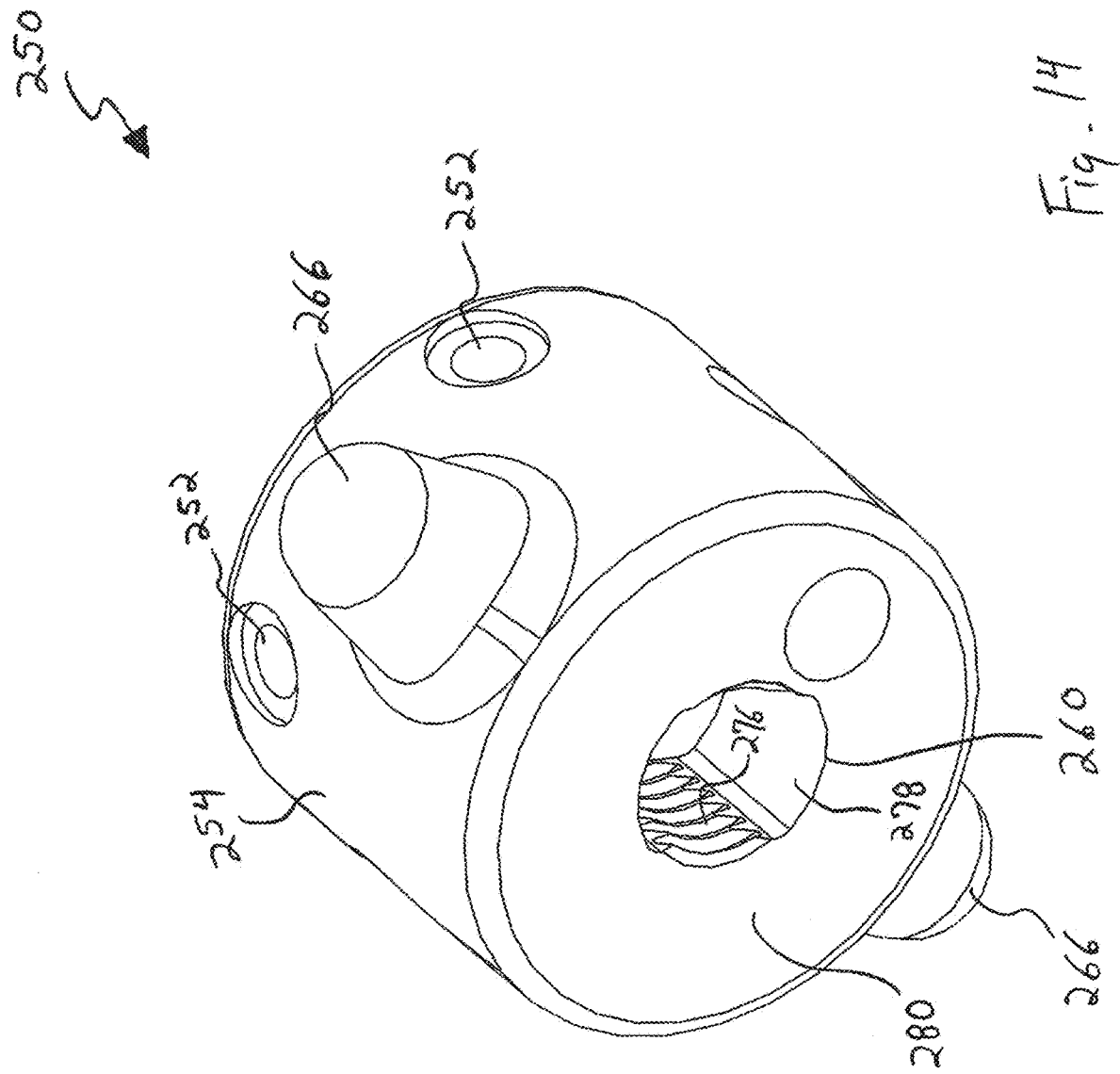
FIG. 14 is an elevated perspective view of the nut of FIG. 1.
Figure 15:
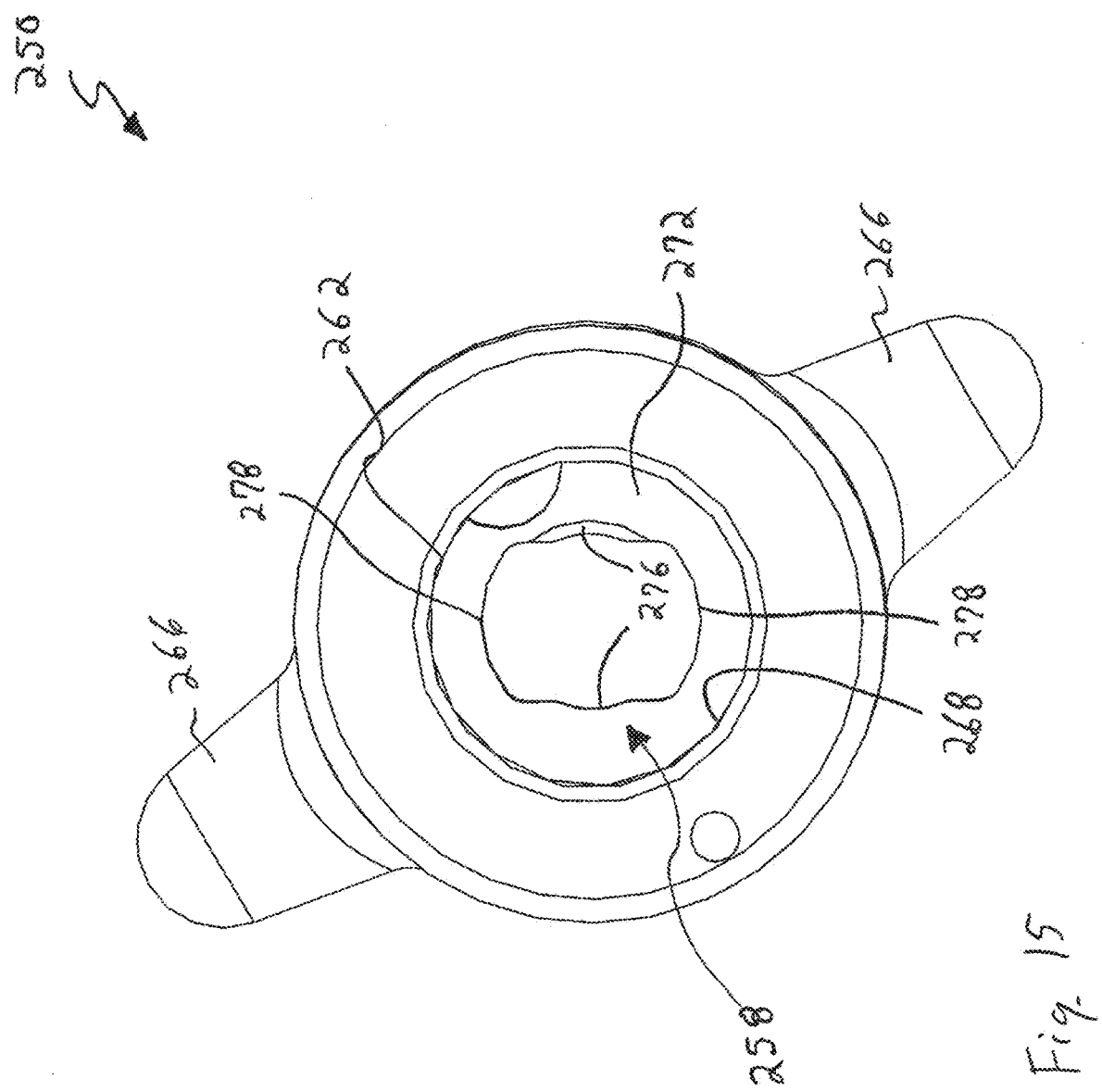
FIG. 15 is an end view of the nut of FIG. 1.

The exemplary embodiments of the present disclosure are described and illustrated below to encompass to devices and methods utilized in fracture reduction and, more specifically, to devices and methods providing length adjustment during fracture fixation. Of course, it will be apparent to those of ordinary skill in the art that the embodiments discussed below are exemplary in nature and may be reconfigured without departing from the scope and spirit of the present disclosure. However, for clarity and precision, the exemplary embodiments as discussed below may include optional steps, methods, and features that one of ordinary skill should recognize as not being a requisite to fall within the scope of the present disclosure.

Referencing FIGS. 1-17, a first exemplary ratcheting strut 100 comprises a ratchet box 102 having a longitudinal opening extending therethrough that accommodates throughput of a ratchet tube 104. In exemplary form, the longitudinal opening is partially defined by a first cylindrical interior wall 106 having a first diameter. A series of fins 110, 112 are mounted to the interior wall 106 and extend into the interior of the longitudinal opening, thereby decreasing the cross-sectional area of the opening. In particular, each fin 110, 112 extends perpendicularly from the interior wall and includes an arcuate edge that matches the arcuate contour of the interior wall 106. An innermost edge of each fin 110, 112 comprises a geometric chord, where the horizontal cross-section of the interior wall 106 is circular. In this exemplary embodiment, a first pair of fins 110 is diametrically positioned opposite one another to create a horizontal cross-section having a constant width between the opposed pair of fins. Likewise, a second pair of fins 112 is mounted identically to the interior wall 106 as the first pair of fins, but is longitudinally spaced from the first pair of fins. Working together, the interior wall 106 and fins 110, 112 allow longitudinal traversal of the ratchet tube 104, while inhibiting axial rotation of the ratchet tube.

In this exemplary embodiment, the ratchet tube 104 comprises a cylindrical ring body having a cylindrical exterior surface 120 axially outset from a cylindrical interior surface 122. In this manner, the interior of the ratchet tube 104 is hollow and has a constant vertical, circular cross-section along its longitudinal length. An exterior surface of the ratchet tube 104 includes the cylindrical exterior surface 120, as well as a pair of planar surfaces 124 extending longitudinally along a majority of the longitudinal length of the ratchet tube. In exemplary form, these planar surfaces 124 may be formed by planarizing opposing sides of the ring body (i.e., hollow cylindrical tube) to remove material from the outside of the ring body, thereby decreasing the wall thickness of the ring body, but not impacting the dimensions of the cylindrical interior surface 122. In exemplary form, the material removed from the ring body can be cross-sectionally represented as a first area outlined by a first chord extending between circumferential exterior points at zero degrees and ninety degrees and by the circumferential surface extending between the same points at zero degrees and ninety degrees. Similarly, the second area may be outlined by a second chord extending between one hundred eighty degrees and two hundred seventy degrees and by the circumferential surface extending between the same points at one hundred eighty degrees and two hundred seventy degrees. The planar surfaces 124, in exemplary form, do not extend along the entire longitudinal length of the ratchet tube 104, therefore a distal end 126 of the ratchet tube is cylindrical, while the opposing proximal end 128 of the ratchet tube is partially cylindrical. More specifically, a pair of arcuate surfaces 132, 134 extends between the planar surfaces 124 to partially define the exterior of the ratchet tube. Each arcuate surface 132, 134 is separated from the other cylindrical surface by approximately ninety rotational degrees, except for the distal end 126 where the cylindrical surfaces seamlessly intersect with the cylindrical exterior surface 120. The dorsal arcuate surface 132 also includes a series of angled depressions 136 that are longitudinally repeated and consistently spaced apart from one another to create a series of angled teeth 138 that are longitudinally inset from the distal and proximal ends 126, 128 of the ratchet tube 104. In exemplary form, each tooth 138 includes a vertical distal surface 144 and an inclined proximal surface 146 that intersects the distal surface to form a horizontal peak 148. As will be discussed in more detail hereafter, the inclined nature of the proximal surface 146 cooperates with a corresponding surface of a repositionable lever 170 to allow ratcheting action between the lever and the ratchet tube 104.

The shape of the ratchet tube 104 allows it to be inserted into the longitudinal opening of the ratchet box 102 so that the proximal end 124 of the ratchet tube 104 is inserted into a proximal opening 156 of the ratchet box 102 and extends through a distal opening 154 prior to insertion of the distal end 126 of the ratchet tube into the interior of the ratchet box. The distal opening 156 is defined by a second cylindrical interior wall 160 having a diameter larger than the first cylindrical interior wall 106. This second cylindrical interior wall 160 extends proximally until terminating at a distal flange 162 that extends between the cylindrical interior walls 106, 160. It should be noted that the cylindrical interior walls 106, 160 are coaxial with one another so that the distal flange 162 has a constant circular cross-section and axial depth. In this exemplary embodiment, the distal flange 162 is operative to inhibit throughput of objects having a diameter larger than the diameter of the first cylindrical interior wall 106. In addition, the fins 110, 112 located on the interior of the first cylindrical interior wall 106 change the longitudinal profile of the longitudinal opening and prohibit throughput of cylindrical objects having a diameter slightly less than the diameter of the first cylindrical interior wall. As mentioned previously, the distal end 126 of the ratchet tube 104 is cylindrical and exhibits a constant exterior diameter, whereas the proximal end 128 and a majority of the longitudinal length of the ratchet tube exhibits a cross-section that is circular with respect to the arcuate surfaces 132, 134, but is rectangular with respect to the planar surfaces 124. This dual shape (circular and rectangular) profile is also consistent with the dual shape profile on the interior of the cylindrical interior wall 106 taking into account the fins 110, 112. In exemplary form, the exterior diameter (between the arcuate surfaces 132, 134) of the ratchet tube 104 is slightly less than the internal diameter of the cylindrical interior wall 106. Likewise, the horizontal width between the opposed fins 110, 112 is slightly larger than the horizontal distance between the planar surfaces 124. As a result, the proximal end 128 of the ratchet tube 104 is able to be longitudinally repositioned along the entire length of the longitudinal opening of the ratchet box 102, whereas the distal end 126 of the ratchet tube is able to be longitudinally repositioned within only a portion of the longitudinal opening because the distal end cannot pass beyond the fins 110, 112. In this manner, when the proximal end 128 of the ratchet tube 104 is first inserted into the distal opening 156 of the ratchet box 102 and longitudinally repositioned proximally, eventually the distal end 126 of the ratchet tube (where the planar surfaces 124 terminate and the uniform circumferential surface begins) abuts the fins 110, which prohibit further proximal motion of the ratchet tube.

In order to fix the position of the ratchet tube 104 with respect to the ratchet box 102, the lever 170 is repositionably mounted to the ratchet box to selectively engage the ratchet tube. More specifically, the lever 170 comprises an L-shaped beam 172 having a cylindrical pivot orifice 174 that accepts a dowel 176 concurrently seated within a cylindrical dowel orifice 178 in order to mount the lever 170 to the ratchet box 102. In exemplary form, the dowel 176 is cylindrical and has an external diameter that is slightly larger than the internal diameter of the cylindrical dowel orifice 178, thus securing the dowel in position via a friction fit. In contrast, the diameter of the cylindrical pivot orifice 174 is slightly larger than the external diameter of the dowel 176, thereby allowing pivoting motion of the lever 170 around the dowel.

In this exemplary embodiment, the lever 170 is biased by a spring 180 to engage the ratchet tube 104. More specifically, the coil spring 180 is seated within a spring receiver 182 of the ratchet box 102. The spring receiver 182 comprises a ring-shaped depression that circumscribes a cylindrical projection that is adapted to be partially inserted into one end of the coil spring 180. Similarly, the underside of the lever 170 also includes a spring receiver 184 that likewise comprises a ring-shaped depression that circumscribes a cylindrical projection adapted to be partially inserted into the other end of the coil spring 180. The bias of the coil spring 180 is selected or set so that when no affirmative pressure is applied by a user to the lever 170, a head 188 of the lever contacts the ratchet tube 104. In exemplary form, the head 188 of the lever 170 includes a series of angled teeth 192 that are each formed by the interaction of a vertical proximal surface 194 and an inclined distal surface 196 that intersects the proximal surface to form a peak 198. In this fashion, the angled teeth 192 of the lever 170 are inclined to match the incline of the angled teeth 138 of the ratchet tube 104. As a result, when no affirmative pressure is applied by a user to the lever 170, the ratchet tube 104 may be repositioned proximally so that the inclined surfaces 146, 196 ride upon one another (and overcome the spring 180 bias to raise the lever 170) successively, thereby allowing the peaks 148, 198 to pass one another. In contrast, when no affirmative pressure is applied by a user to the lever 170, the ratchet tube 104 may not be repositioned distally because the vertical surfaces 144, 194 contact one another and do not allow distal motion because the lever remains in the line of travel of the ratchet tube. Accordingly, in order to reposition the ratchet tube 104 distally, a user needs to apply affirmative pressure to the lever 170 and overcome the spring 180 bias, thereby removing the lever from the line of travel of the ratchet tube. When the appropriate distal travel is reached, the user simply discontinues affirmative pressure to the lever 170, thereby allowing the spring 180 bias to dominate and cause the lever to contact the ratchet tube 104 so that the vertical surfaces 144, 194 contact one another and do not allow distal motion.

The lever 170 may also be locked in position so that the angled teeth 192 engage the angled teeth 138 of the ratchet tube 104. In order to lock the lever 170 in the position shown in FIG. 3, the lever includes a lock orifice 200 that is sized to receive a portion of a thumb screw 204. The thumb screw 204 includes a knob 206 mounted to a perpendicularly extending, linear projection 208 having threads 210 adapted to engage threads 212 on the inside of a thumb screw orifice 214 extending through the ratchet box 102. When the projection 208 of the thumb screw 204 is inserted through the thumb screw orifice 214 and lock orifice 200, the lever 170 is not pivotally repositionable so that the teeth 192 of the lever are out of the line of travel of the teeth 138 of the ratchet tube 104. Consequently, to pivot the lever 170 so that the teeth 192 of the lever 170 are out of the line of travel of the teeth 138 of the ratchet tube 104, the thumb screw 204 needs to be positioned so that the projection 208 is no longer received within the lock orifice 200. After the thumb screw 204 is positioned so that the projection 208 is no longer received within the lock orifice 200, the lever 170 may be repositioned by application of affirmative pressure to overcome the bias of the spring 180, thereby pivoting the lever so that the teeth 192 of the lever are out of the line of travel of the teeth 138 of the ratchet tube 104.

When the ratchet tube 104 is repositioned with respect to the ratchet box 102, other components mounted to the ratchet tube are also repositioned. In this exemplary embodiment, a tube mount 220 is coupled to the proximal end 128 of the ratchet tube via a friction fit. It should be understood, however, that other means of attachment may be used such as, without limitation, adhesives, set screws, and welds. In this manner, longitudinal motion of the ratchet tube 104 causes longitudinal motion of the tube mount 220 and vice versa. The tube mount 220 includes a through opening 222 that accommodates longitudinal movement of the ratchet tube 104 independent of movement of the tube mount. A distal end 224 of the tube mount includes a cylindrical collar 226 that circumscribes the proximal end 128 of the ratchet tube 104. On the interior of this collar 226 is a flange 228 that provides an abutment surface against which the exposed proximal end 128 of the ratchet tube contacts when fully seated within the collar. The flange 228 also operates to change the profile of the through opening 222 from circular along the collar 226, to a narrower hybrid profile. This hybrid profile is defined by a pair of parallel, planar surfaces 230 bridged by a pair of arcuate surfaces 232 that extend longitudinally along a sleeve 236 integrally formed with the flange 228 and collar 226. An exterior surface of the sleeve 236 is cylindrical and smooth, but for a circumferential trench 240 and a radial through opening 242, where the radial through opening extends into the through opening 222 but the circumferential trench does not. The trench 240 is adapted to partially receive a set screw mounted to a nut 250 that is mounted to and rotationally repositionable with respect to the tube mount 220.

In exemplary form, the nut 250 circumscribes a portion of the sleeve 236 and is rotationally repositionable with respect to the sleeve. The nut also includes one or more set screw orifices 252 open to the cylindrical exterior surface 254 that extend into a hollow interior 258, which includes proximal and distal openings 260, 262. The exterior surface 254 also includes a pair of rounded projections 266 that are utilized to grasp the nut 250 and facilitate rotation of the nut with respect to the sleeve 236. In this exemplary embodiment, the distal opening 262 allows access to a cylindrical cavity defined by a circumferential interior wall 268. At the proximal end of this interior wall 268 is a flange 272 that provides an abutment surface against which the exposed proximal end of the sleeve 236 contacts when fully seated within the nut 250. The flange 272 also operates to change the profile of the hollow interior 258 from circular along the interior wall 268, to a narrower hybrid profile. This hybrid profile is defined by a pair of parallel surfaces 276 tapped to create threads and bridged by a pair of arcuate surfaces 278 that extend longitudinally until reaching a proximal end 280 of the nut 250. The parallel, tapped surfaces 276 are adapted to be engaged by a threaded post 284 that extends through the nut 250, the tube mount 220, and partially through an interior of the ratchet tube 104.

By way of example, the threaded post 284 comprises a cylinder having a cylindrical exterior surface 286, as well as a pair of planar surfaces 288 extending longitudinally along a majority of the longitudinal length of the threaded post. In exemplary form, these planar surfaces 288 may be formed by planarizing opposing sides of the cylinder to remove material from the exterior, thereby decreasing the thickness of the cylinder at certain circumferential locations. In exemplary form, the material removed from the cylinder can be cross-sectionally represented as a first area outlined by a first chord extending between circumferential exterior points at zero degrees and ninety degrees and by the circumferential surface extending between the same points at zero degrees and ninety degrees. Similarly, the second area may be outlined by a second chord extending between one hundred eighty degrees and two hundred seventy degrees and by the circumferential surface extending between the same points at one hundred eighty degrees and two hundred seventy degrees. The planar surfaces 288, in exemplary form, do not extend along the entire longitudinal length of the threaded post 284 so that a distal end 292 of the threaded post retains a cylindrical shape, while the opposing proximal end 294 of the threaded post is partially cylindrical. More specifically, a pair of cylindrical surfaces 296 extends between the planar surfaces 288 to partially define the exterior of the ratchet tube. Each cylindrical surface 296 is separated from the other cylindrical surface by approximately ninety rotational degrees, except for the distal end where the cylindrical surfaces seamlessly intersect with the cylindrical exterior surface 286. Both cylindrical surfaces 296 are tapped along a predetermined length that extends to the proximal end 294 to provide a series of repeating, partial threads 298. It is these partial threads 298 that are adapted to engage the tapped surfaces 276 of the nut 250 so that rotational repositioning of the nut results in longitudinal repositioning of the threaded post 284. More specifically, clockwise rotation of the nut 250 may reposition the threaded post 284 longitudinally in a distal direction, while counter-clockwise rotation of the nut 250 may reposition the threaded post 284 longitudinally in a proximal direction, or vice versa.

The distal end 292 of the threaded post 284 includes a cylindrical cavity that is tapped to provide internal threads 300. These threads 300 are adapted to be engaged by the threads 304 of a post cap 306. The post cap 306 includes a proximal cylindrical end. 308 having threads 304 in order to mount the post cap to the threaded solid post 284. A solid distal end 312 of the post cap 306, integrally formed with the proximal end 308, is also cylindrical and includes a larger diameter than the proximal end. This larger diameter is slightly less than the diameter of the cylindrical interior surface 122 of the ratchet tube 104, thereby allowing the post cap to slide longitudinally within the interior of the ratchet tube. The distal end 312 also includes a circumferential trench 314 inset from the tip that is sized to accommodate a discontinuous friction sleeve 316. The discontinuous friction sleeve 316 is seated within the trench 314 and partially compressed by the cylindrical interior surface 122 of the ratchet tube 104. In a static environment, the outer diameter of the friction sleeve 316 is slightly larger than the diameter of the interior surface 122 of the ratchet tube 104. But when the friction sleeve 316 is seated within the trench 314 and inserted into the ratchet tube 104, the friction sleeve is circumferentially compressed to have an external diameter roughly equal to the diameter interior surface 122 of the ratchet tube. In this manner, the friction sleeve 316 creates frictional resistance against longitudinal repositioning of the sleeve with respect to the ratchet tube 104, which also creates resistance against longitudinal repositioning of the post cap 306 and threaded post 284 with respect to the ratchet tube. But this frictional resistance is not so great as to inhibit longitudinal motion of the sleeve 316, the post cap 306, and threaded post 284 when the nut 250 is rotated.

The proximal end 294 of the threaded post 284 is mounted to a ball joint 320 having a spherical ball end 322 integrally formed with a hollow cylinder 324. The hollow cylinder is threaded and these threads 328 are adapted to engage the partial threads 298 of the threaded post 284 in order to mount the threaded post to the ball joint 320.

The spherical ball end 322 of the ball joint 320 is rotationally and pivotally repositionable with respect to a socket cooperatively formed by a ball joint housing 330 and a ball joint cap 334. In exemplary form, the ball joint housing 330 comprises a casing that partially encapsulates the spherical ball end 322 of the ball joint 320. On the interior of this casing is a semispherical depression that provides a bearing surface against which the spherical ball end rotates and pivots. The ball joint housing 330 also includes a circular ring 336 integrally formed with the casing and having a diameter greater than the diameter of the spherical ball end. In order to retain the spherical ball end 322 within the ball joint housing 330, as well as selectively removing the spherical ball end from within the ball joint housing, the circular ring includes threads 340 that are adapted to engage threads 342 of the ball joint cap 334 to secure the ball joint cap to the ball joint housing via a friction fit.

Figure 16:
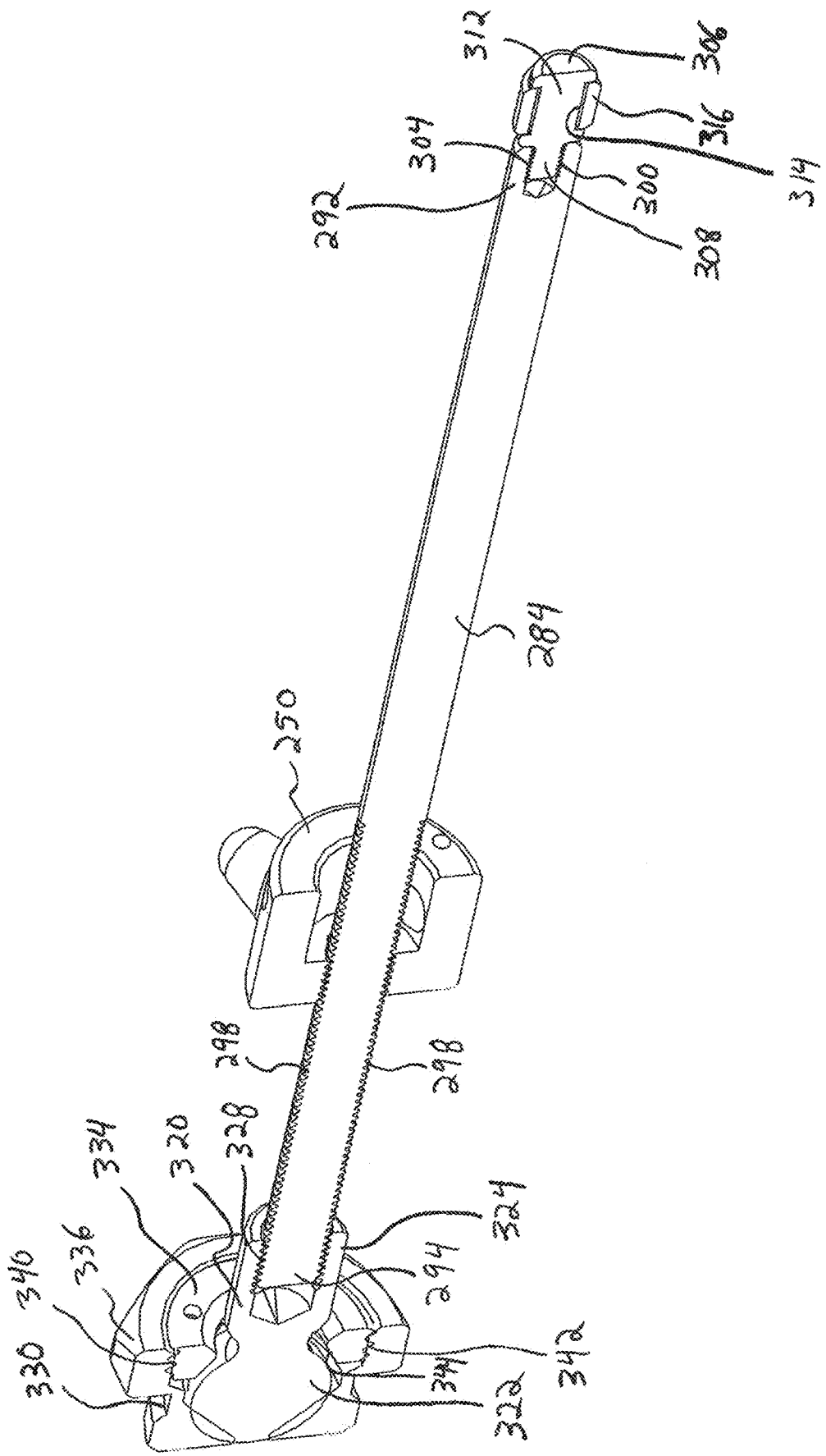
FIG. 16 is a cross-sectional view of the components of FIG. 10 taken along line 16-16.
Figure 117:
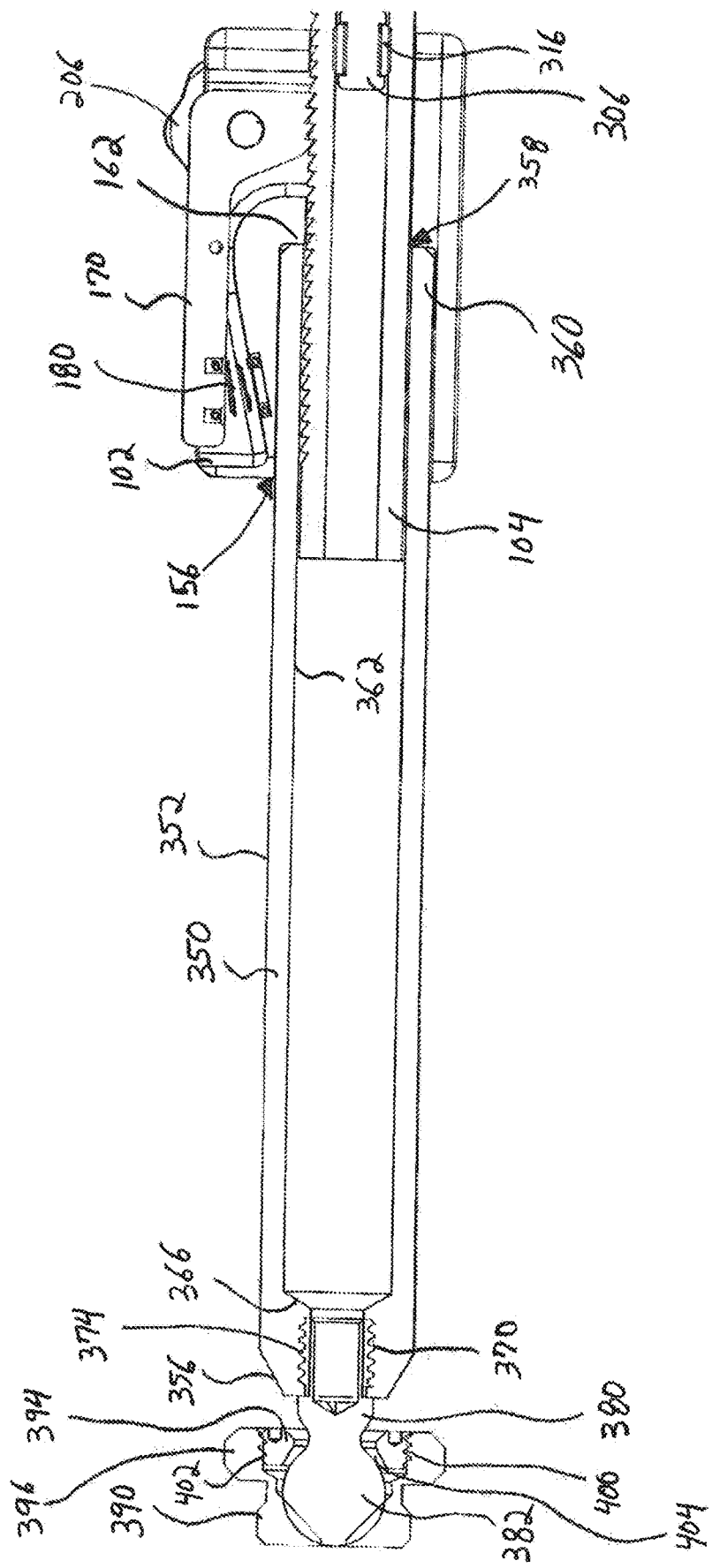
Figure 19:
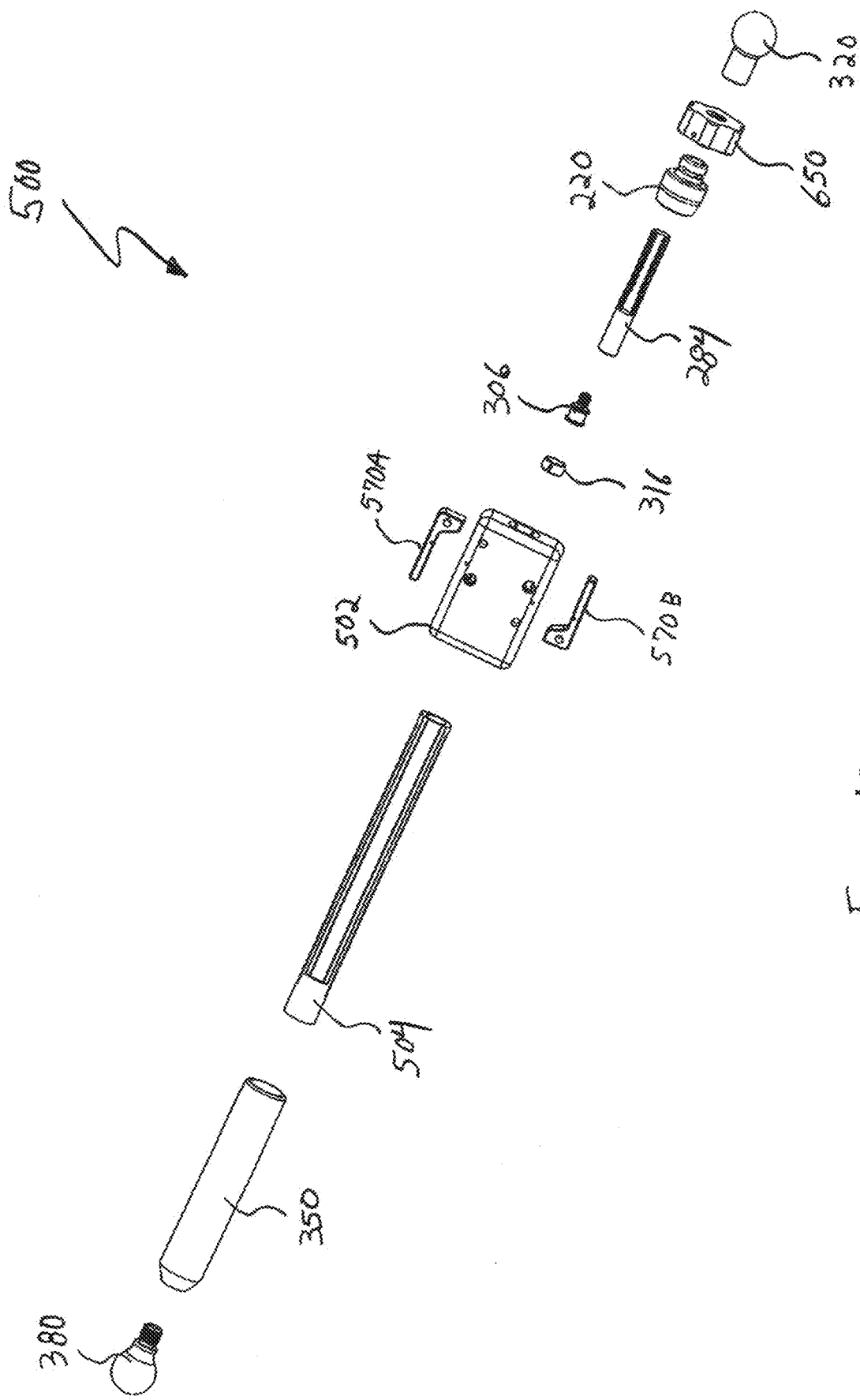
FIG. 19 is an exploded view of the second exemplary ratcheting strut of FIG. 18.
Figure 20:
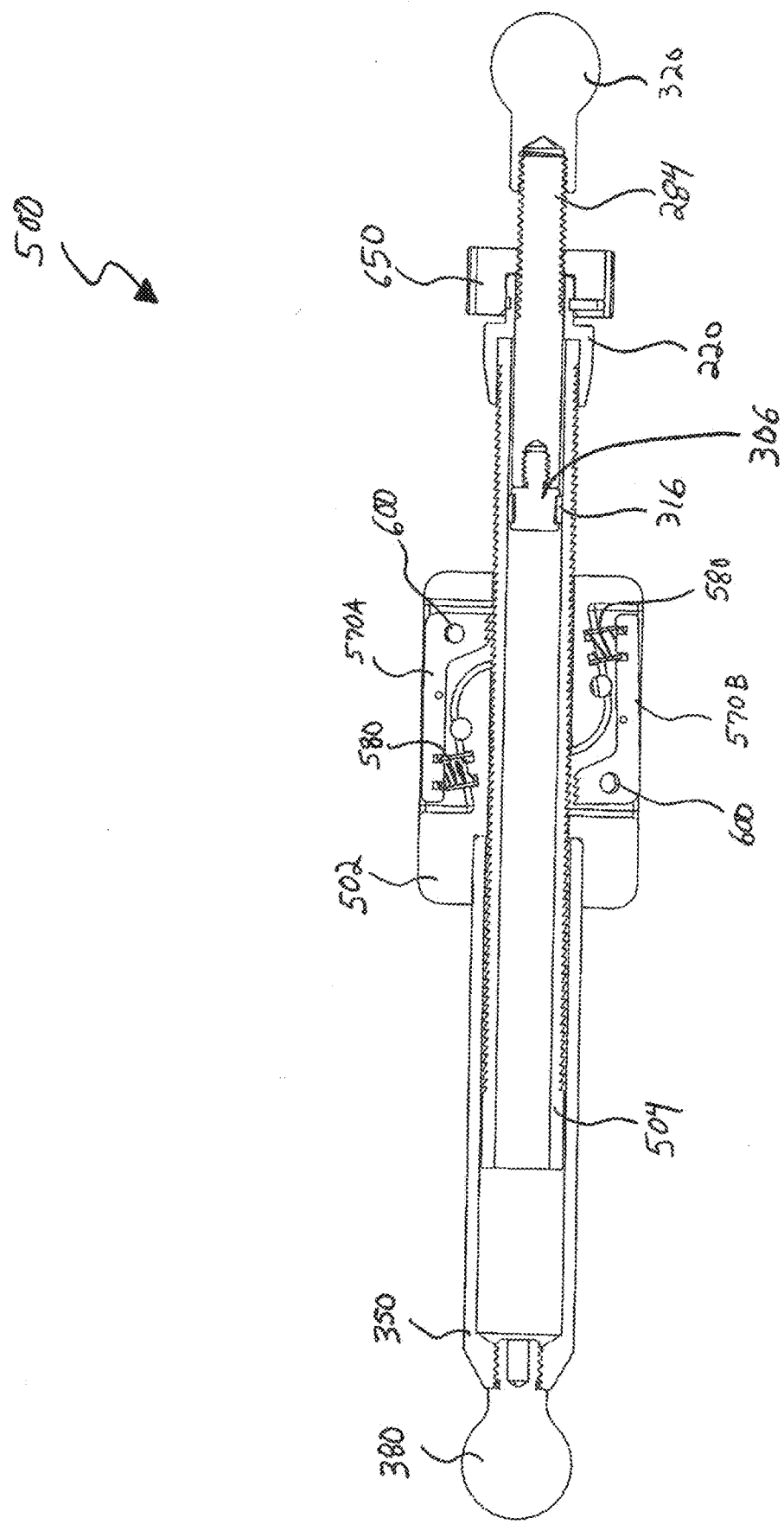
FIG. 20 is a cross-sectional view of the second exemplary ratcheting strut of FIG. 18 taken along line 20-20.
Figure 21:
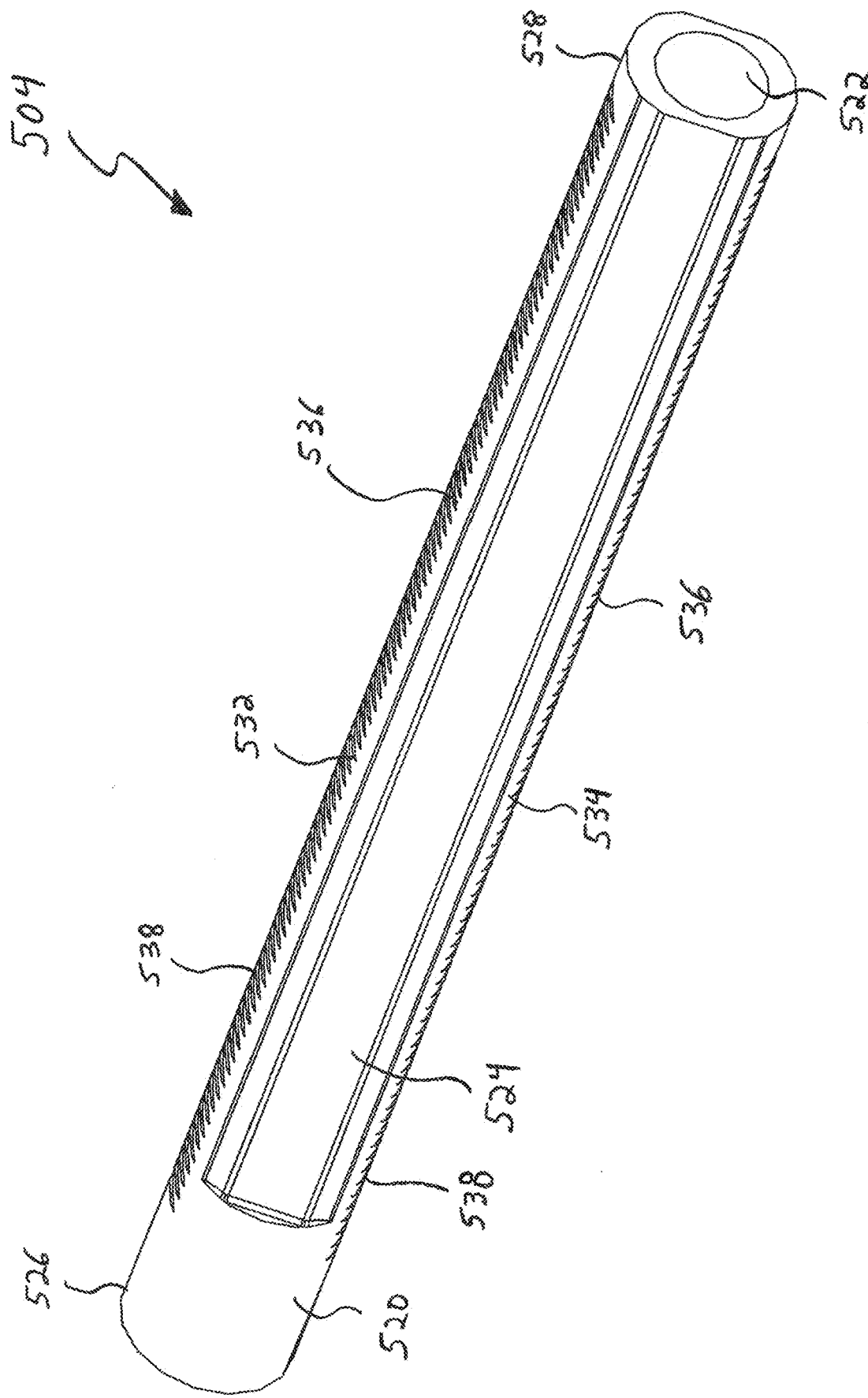
FIG. 21 is an elevated perspective view of the ratchet tube of FIG. 18.
Figure 22:
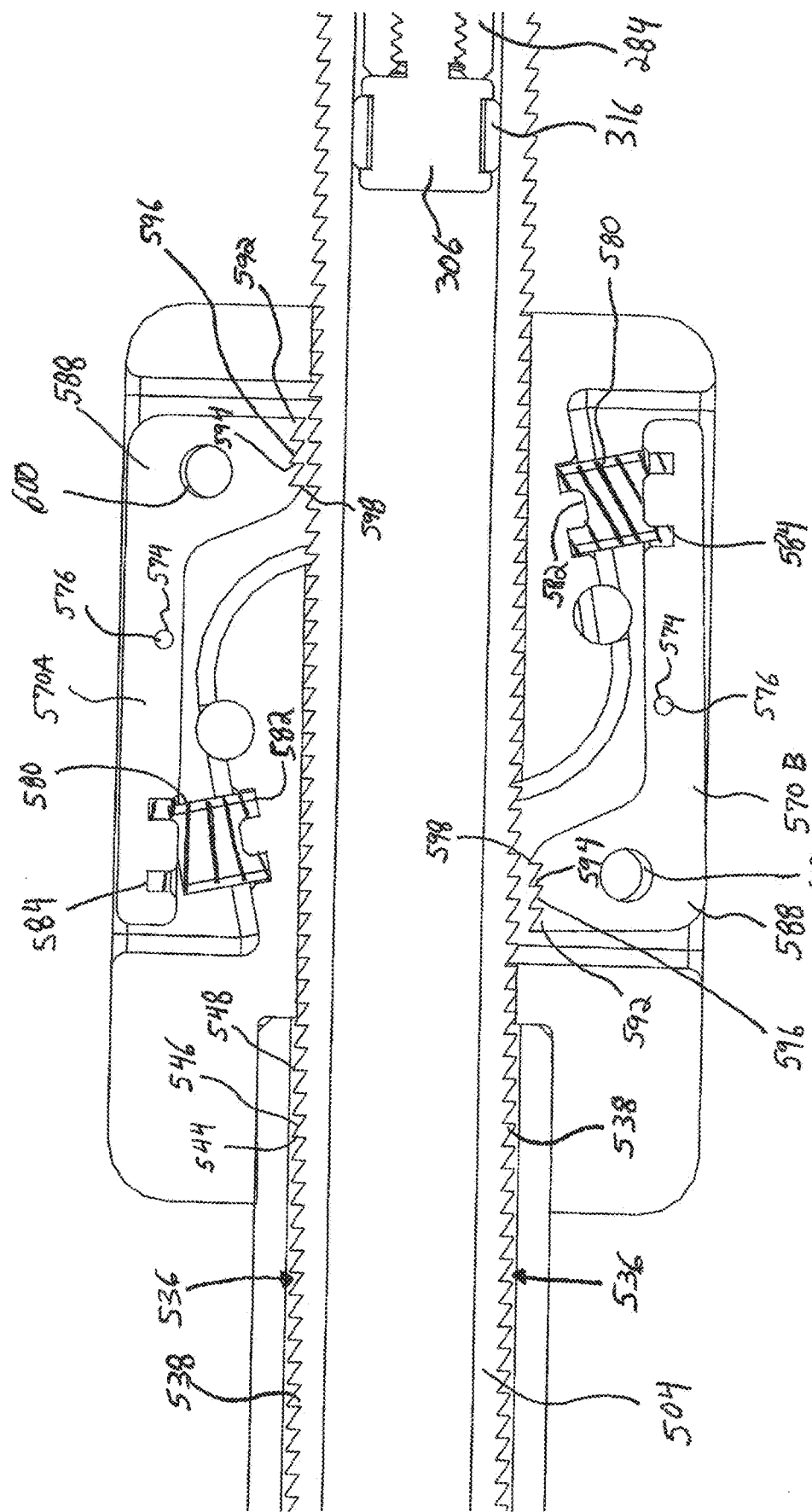
FIG. 22 is a magnified view of the ratchet box and internal components shown in FIG. 20.
Figure 23:
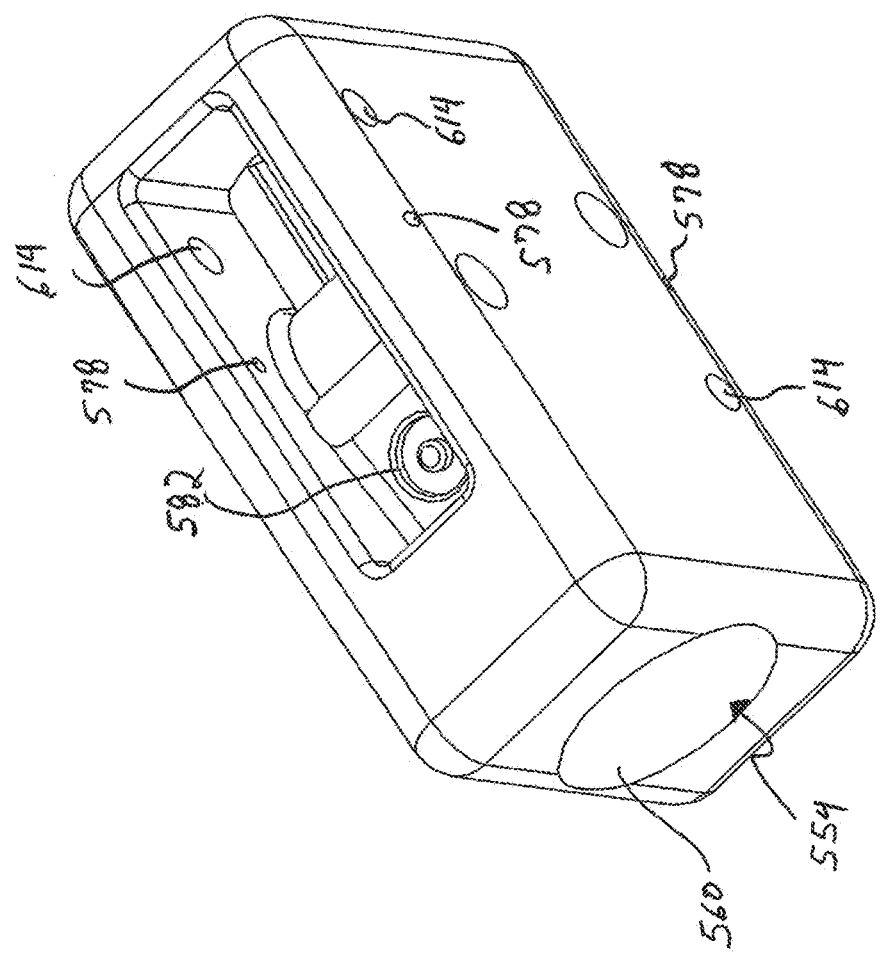
FIG. 23 is an elevated perspective view of the ratchet box of FIG. 18.
Figure 24:
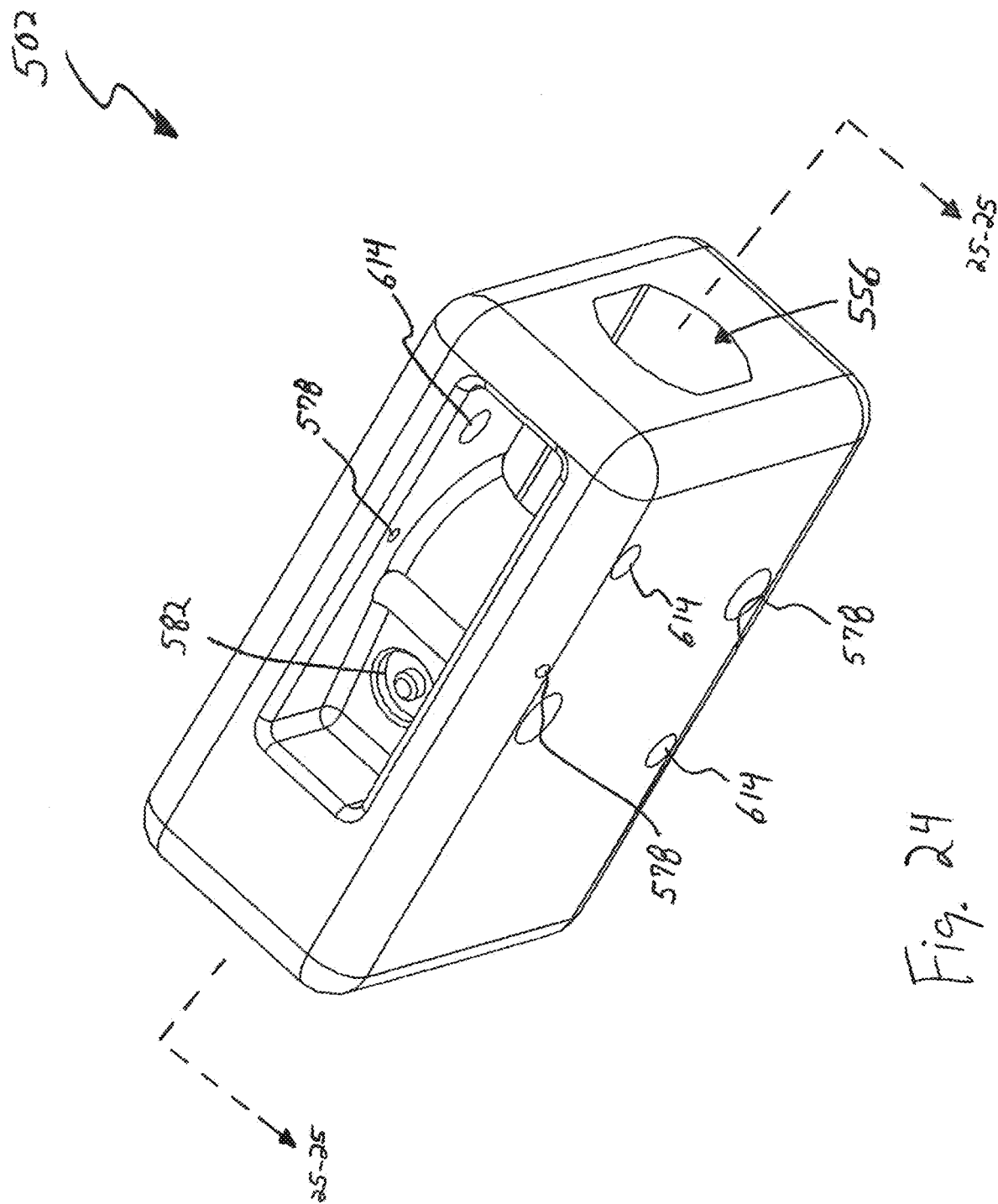
FIG. 24 is another elevated perspective view of the ratchet box of FIG. 18.
Figure 25:
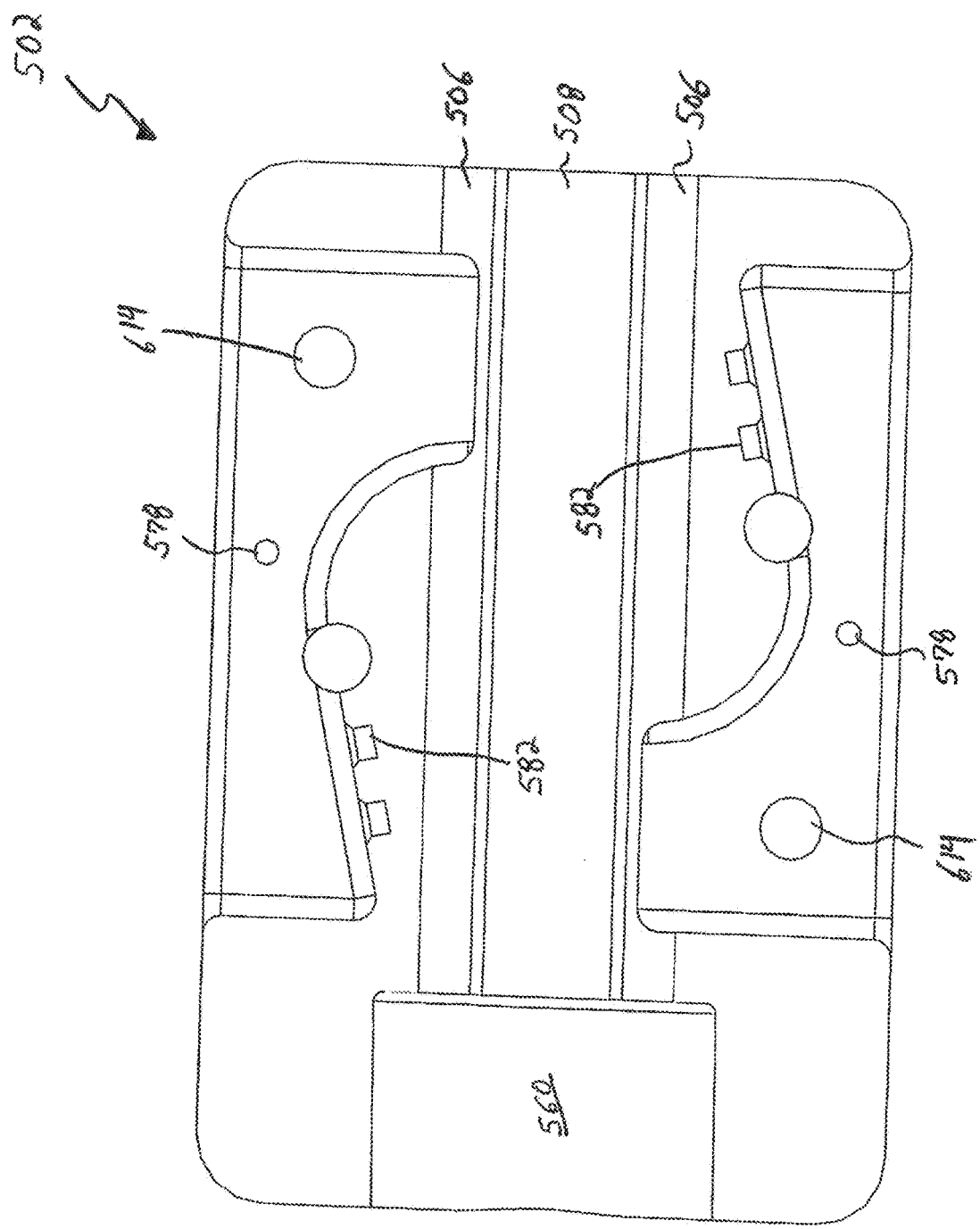
FIG. 25 is a cross-sectional view of the ratchet box of FIG. 20 taken along line 25-25.
Figure 26:
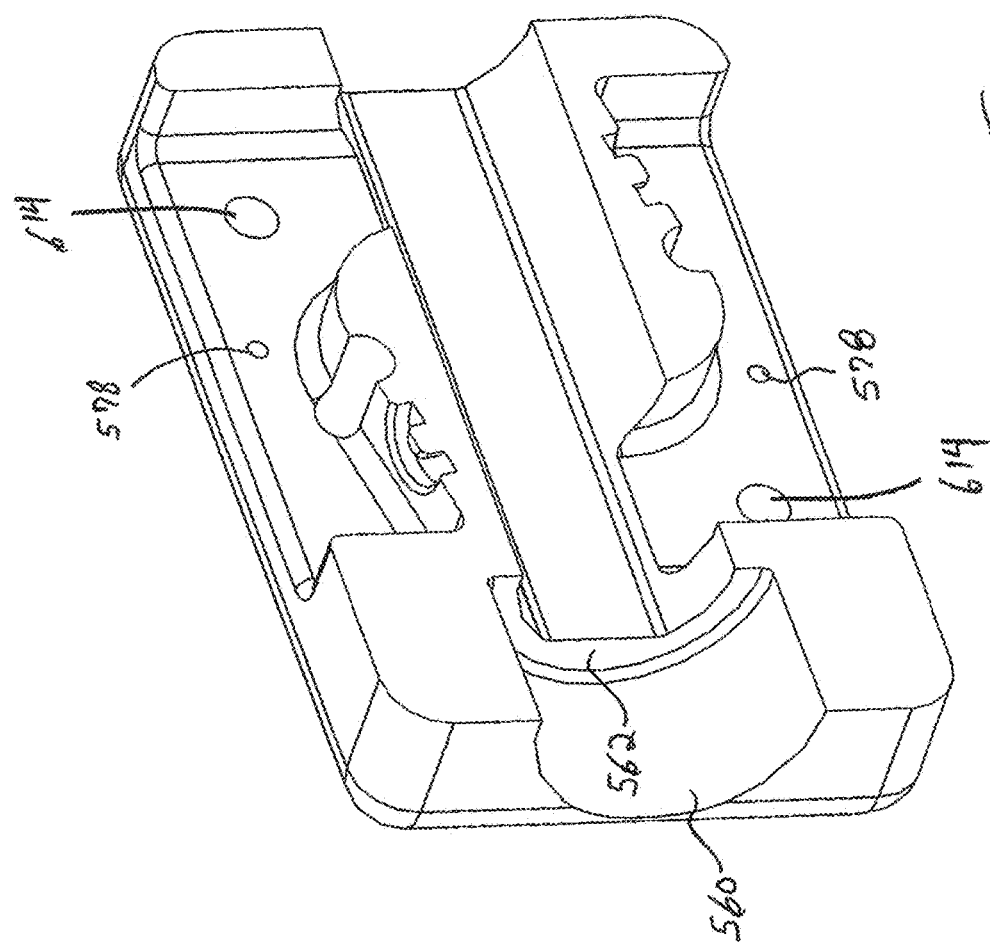
FIG. 26 is an elevated perspective view of the cross-section of FIG. 25.
Figure 27:
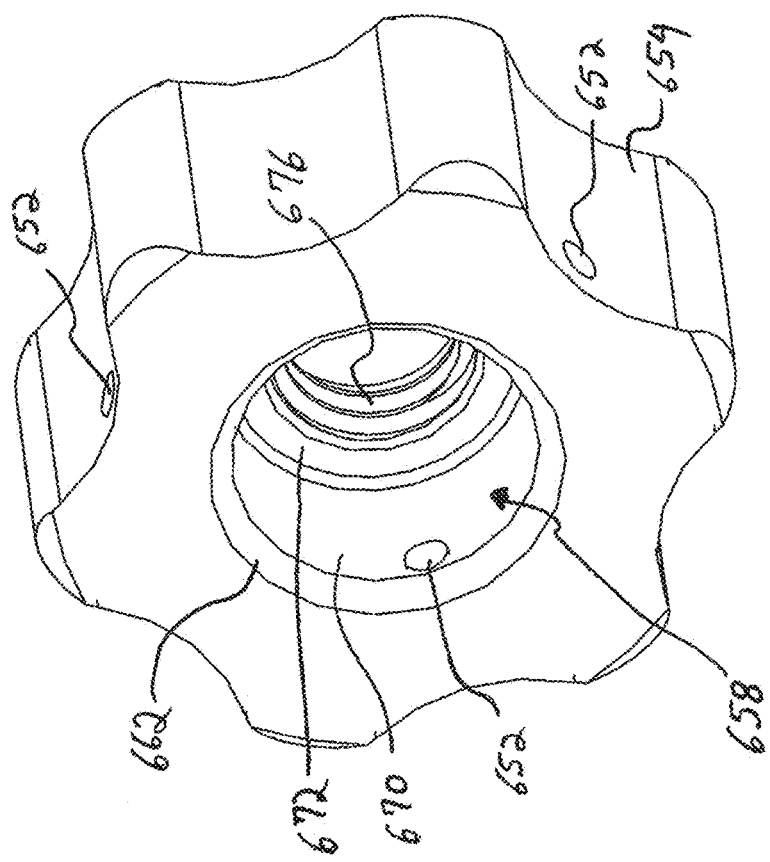
FIG. 27 is an elevated perspective view of the nut of FIG. 18.
Figure 28:
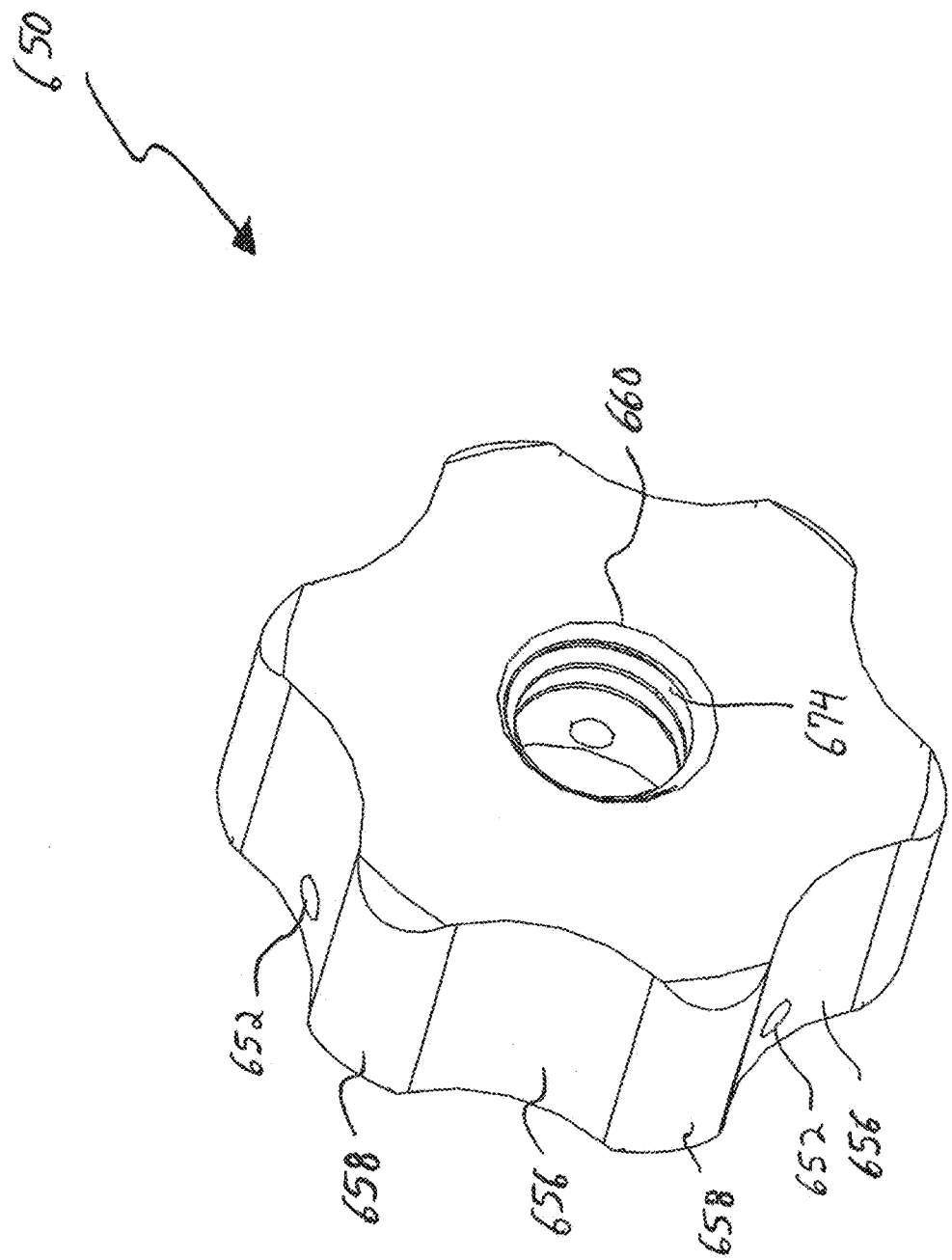
FIG. 28 is another elevated perspective view of the nut of FIG. 18.
Figure 29:
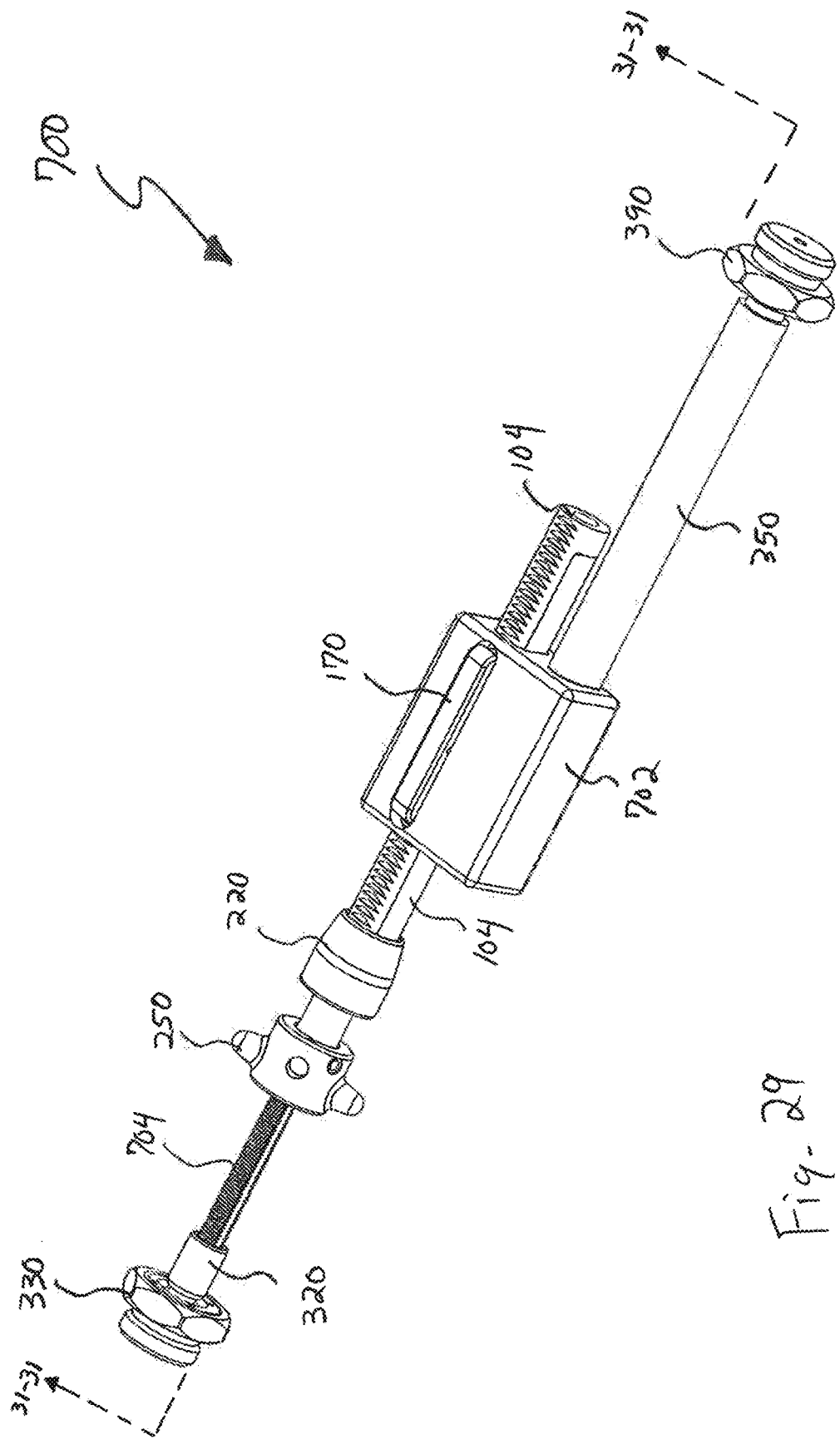
FIG. 29 is an elevated perspective view of an assembled third exemplary ratcheting strut in accordance with the instant disclosure.
Figure 30:
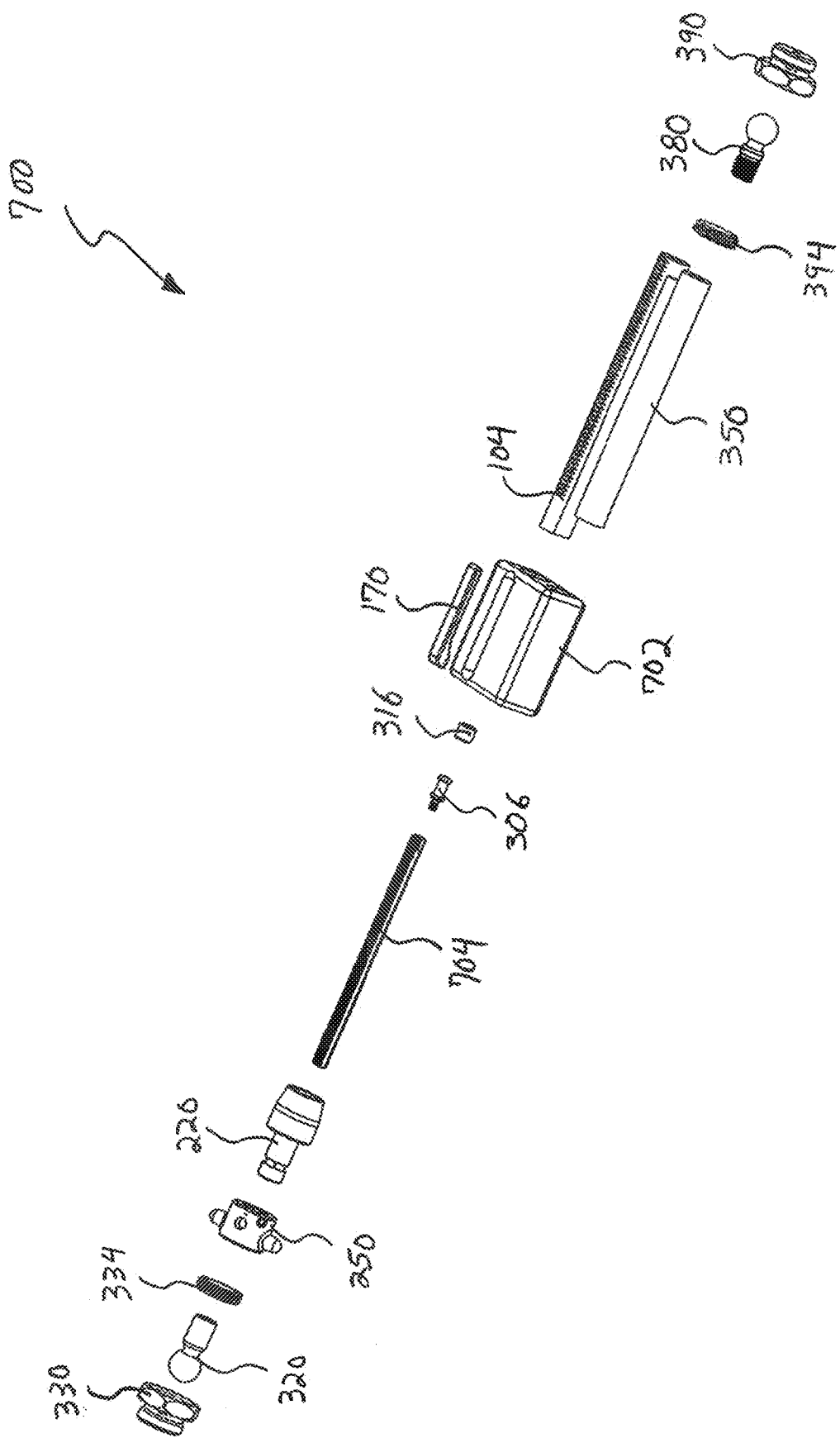
FIG. 30 is an exploded view of the third exemplary ratcheting strut of FIG. 29.
Figure 31:
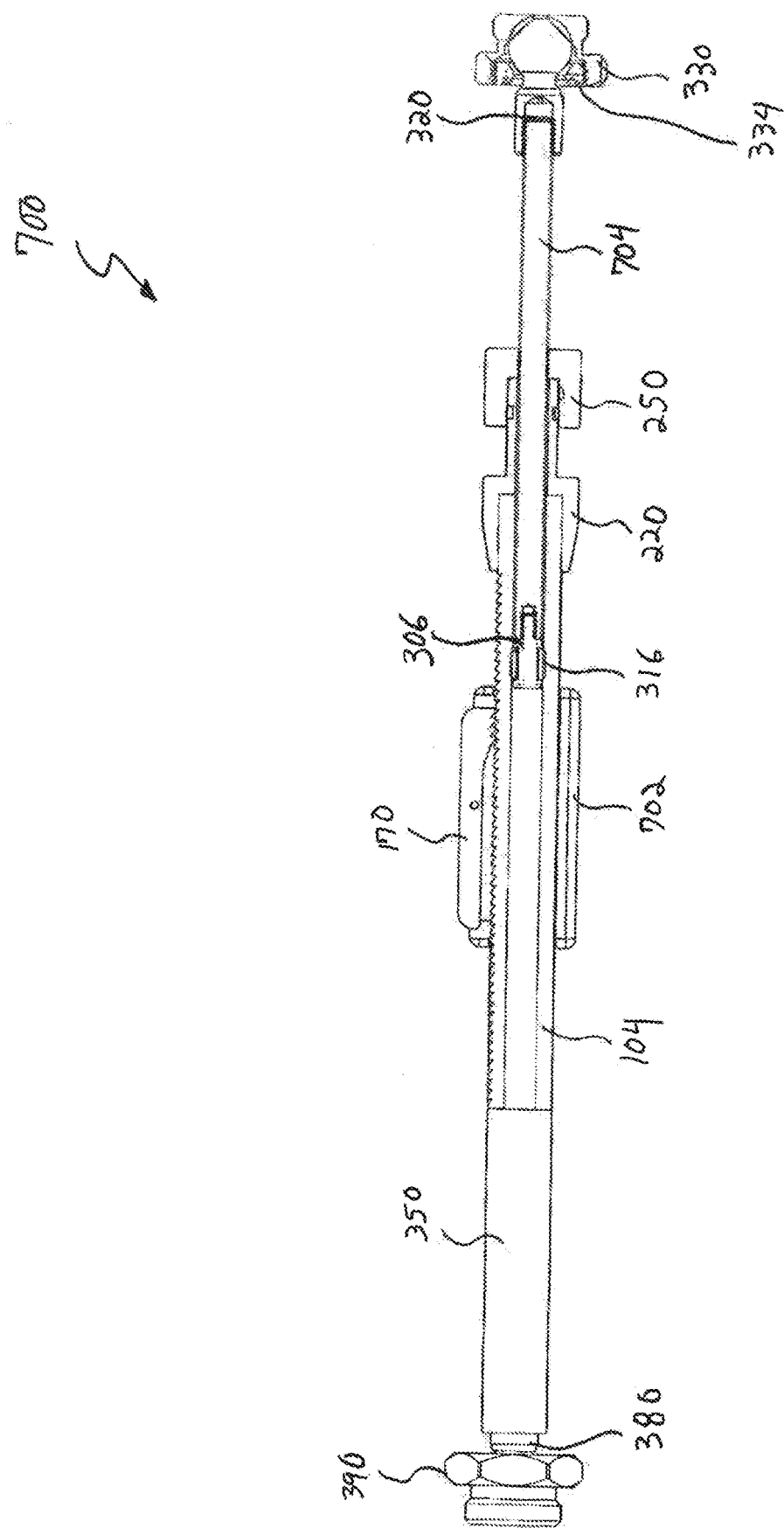
FIG. 31 is a cross-sectional view of the third exemplary ratcheting strut of FIG. 29 taken along line 31-31.
Figure 32:
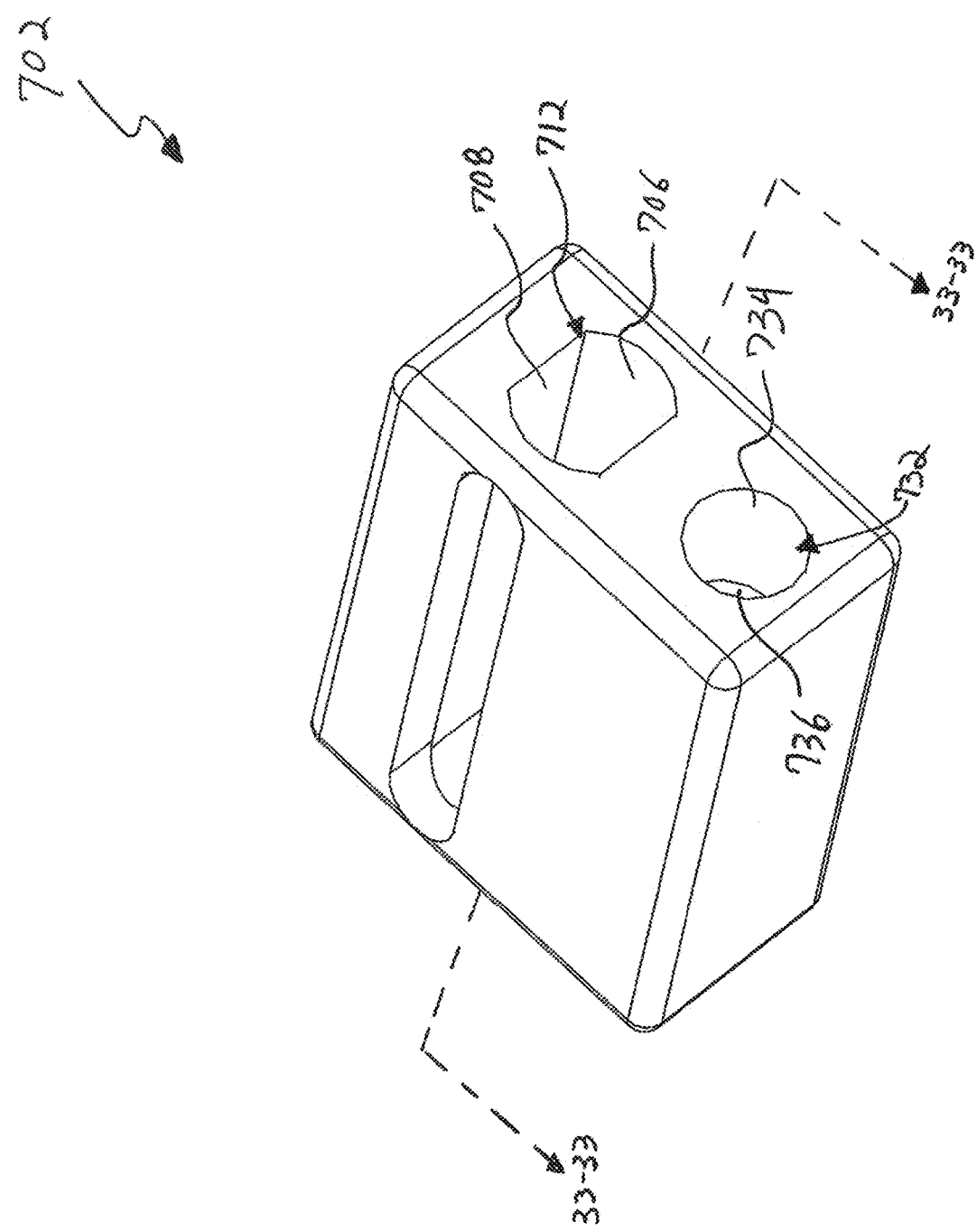
FIG. 32 is an elevated perspective view of the ratchet box of FIG. 29.
Figure 33:
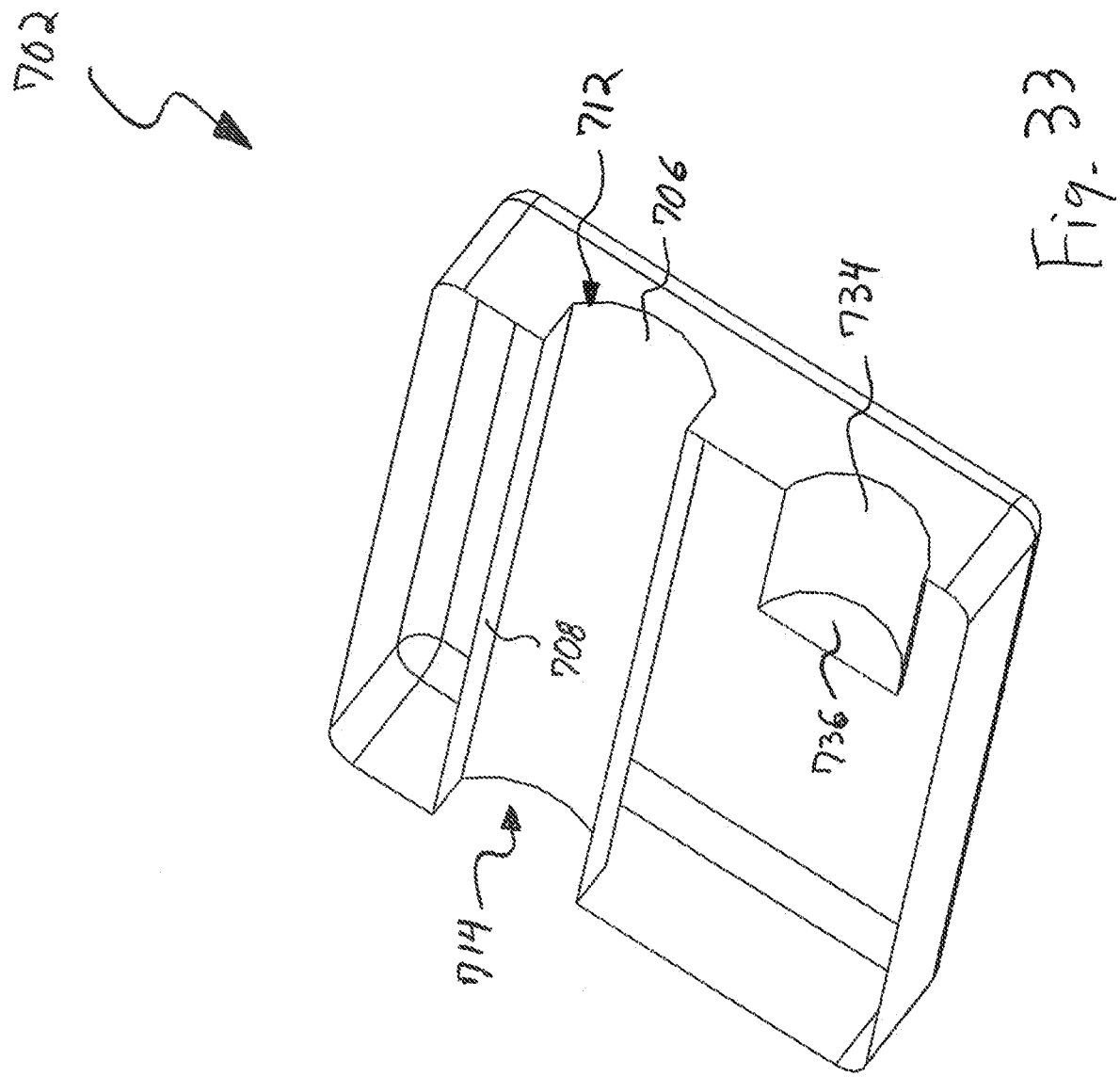
FIG. 33 is a cross-sectional view of the ratchet box of FIG. 32 taken along line 33-33.
Figure 34:
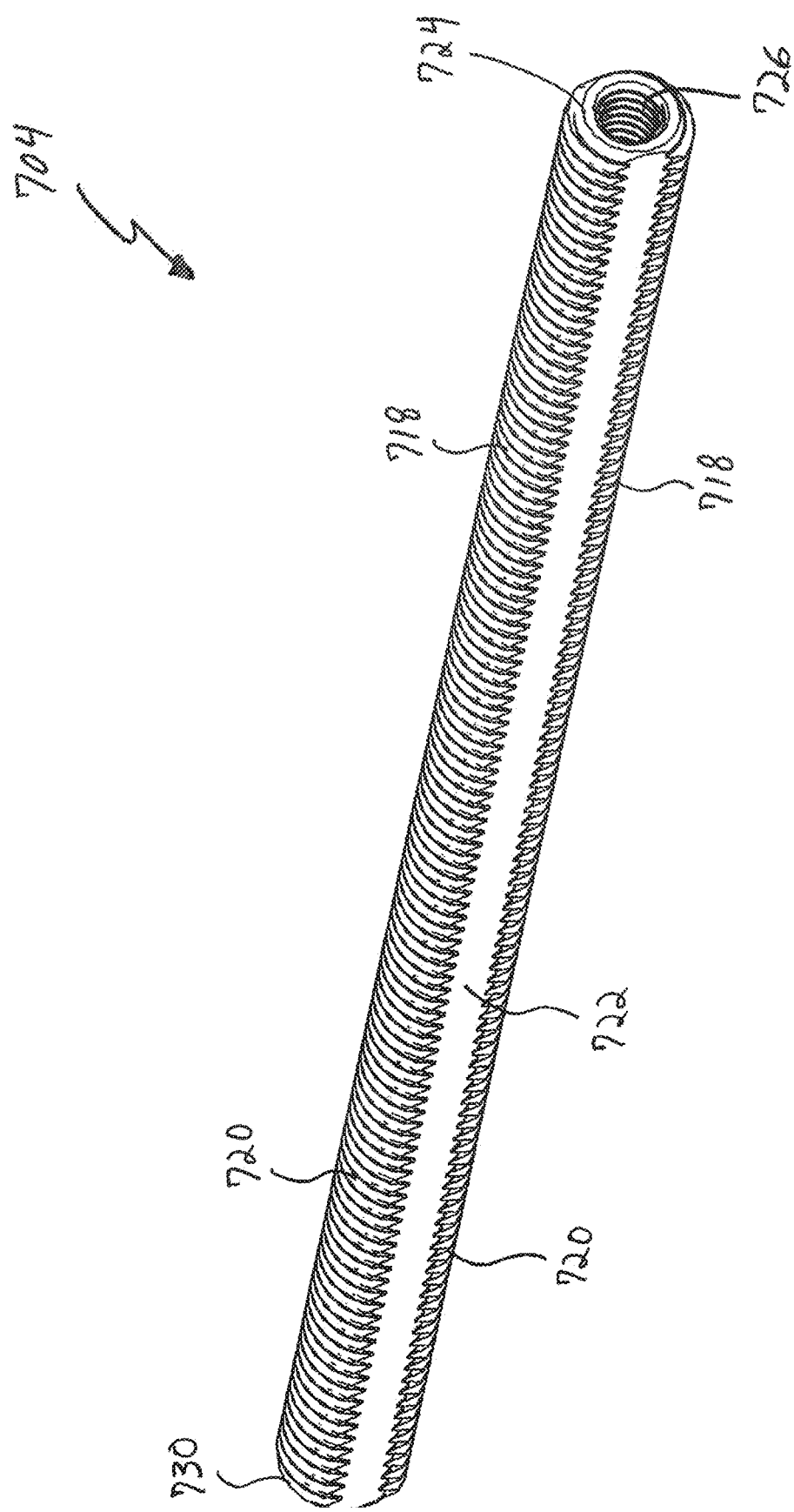
FIG. 34 is an elevated perspective view of the threaded post of FIG. 29.
Figure 35:
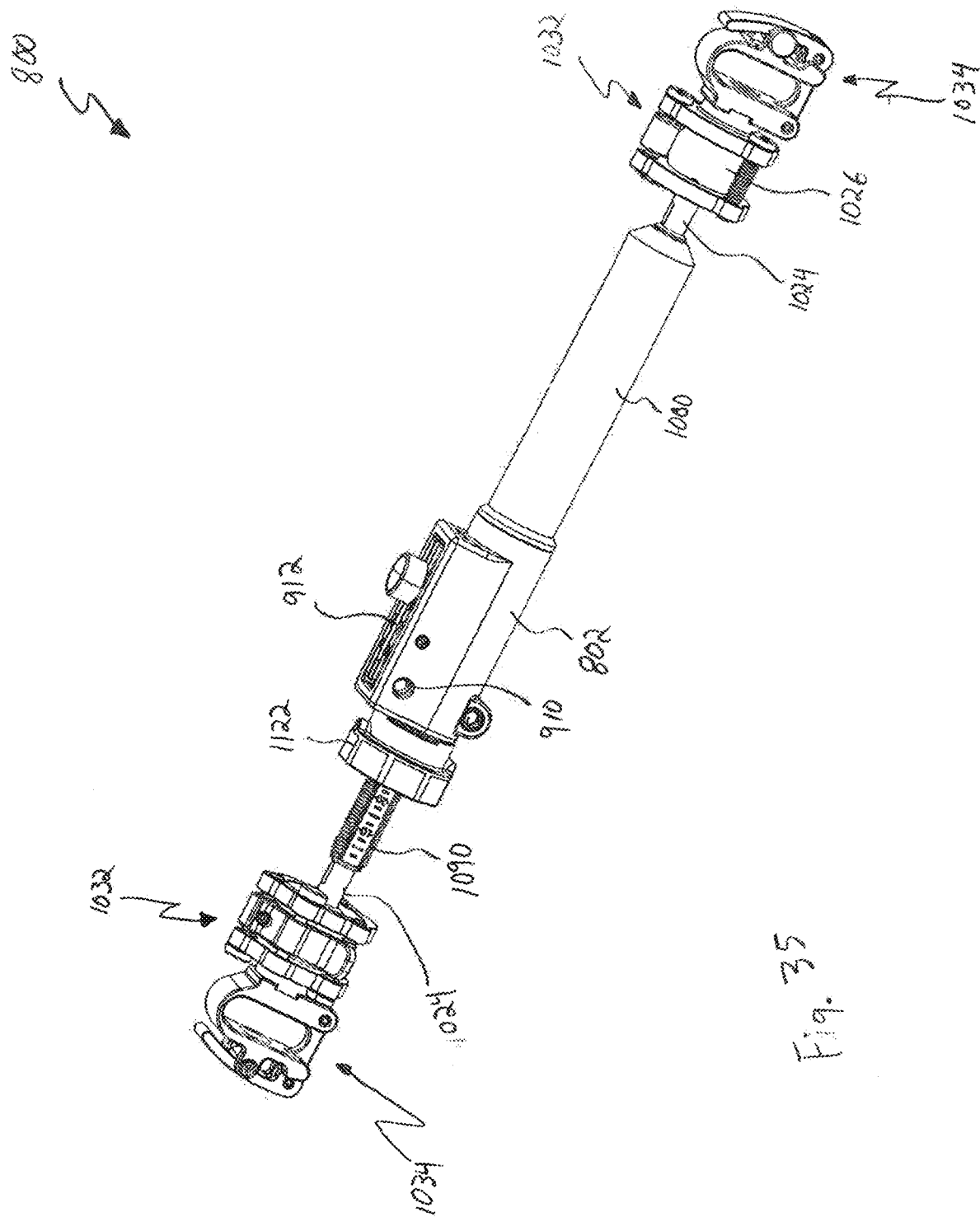
FIG. 35 is an elevated perspective view of a fourth exemplary ratcheting strut in accordance with the instant disclosure.
Figure 36E:
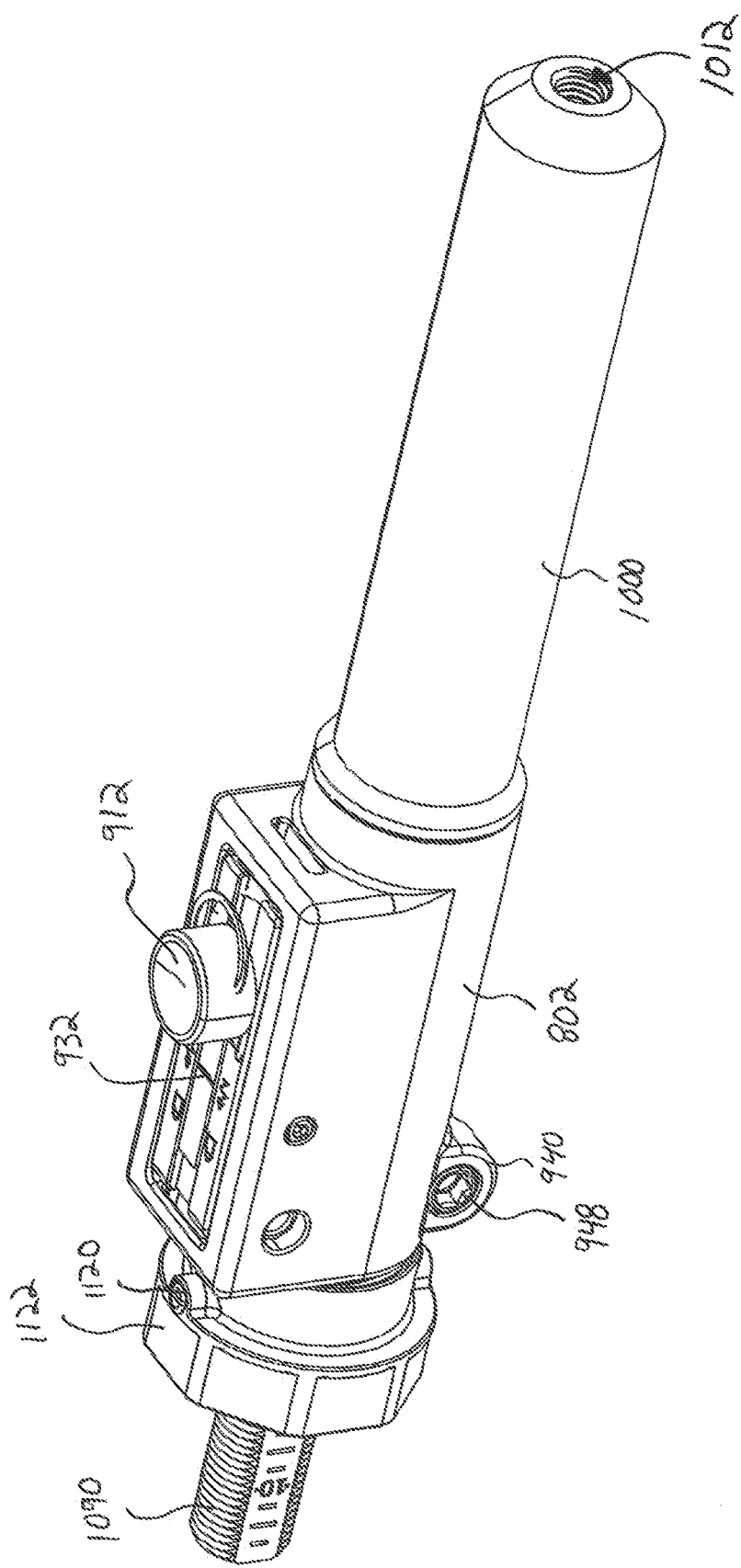
FIG. 36 is an elevated perspective view of a subset of components comprising part of the exemplary ratcheting strut of FIG. 35.
Figure 39:
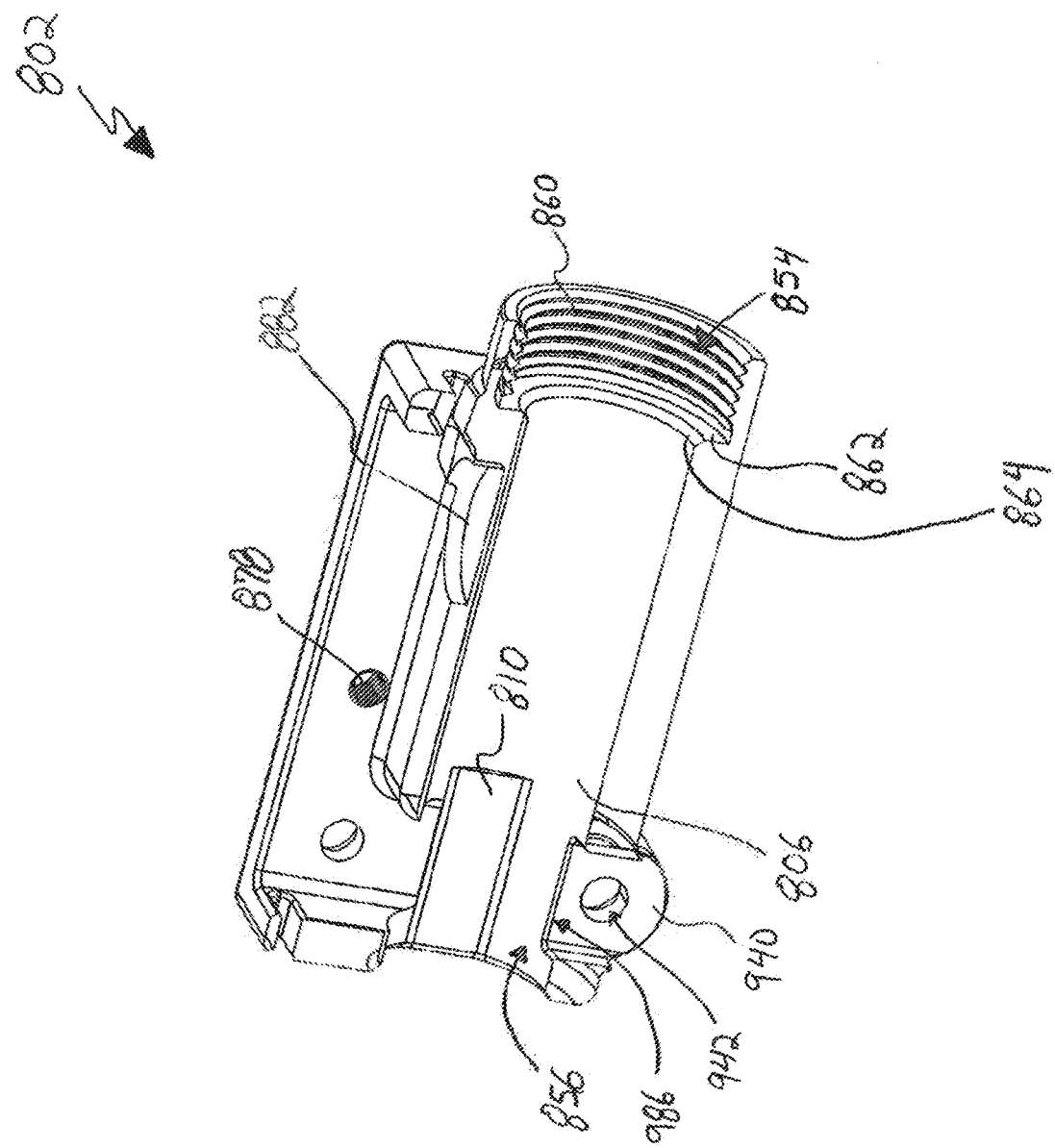
FIG. 39 is a cross-sectional view of the exemplary ratchet box of FIG. 38 taken vertically and along the longitudinal axis.

As shown in FIG. 16, the ball joint cap 334 is ring-shaped and includes a central opening defined by an arcuate circumferential surface 344. This arcuate circumferential surface 344 cooperates with the semispherical depression of the ball joint housing 330 to create the spherical socket within which the spherical ball end 322 is able to rotate and pivot. In this exemplary embodiment, the diameter of the central opening of the ball joint cap 334 is less than the diameter of the spherical ball end 322 within the ball joint housing 330 so that once the ball joint cap and ball joint housing are mounted to one another with the spherical ball end 322 located therein, removal of the spherical ball end is not possible without discontinuing the ball joint cap from being mounted to ball joint housing.

Referring back to FIGS. 5-7, as discussed previously, the distal end of the ratchet box 102 includes a distal opening 156 defined by the second cylindrical interior wall 160, which ends proximally when it meets the distal flange 162. The distal opening is sized to accommodate throughput of the ratchet tube 104 as well as partial insertion of another tube 350. This second tube 350 is longitudinally cylindrical and includes a smooth exterior circumferential surface 352 that has a relatively constant diameter along the vast majority of the length of the second tube, but for the distal end 356. An interior of the second tube 350 is hollow and includes an opening 358 at a proximal end 360 of the second tube. This opening 358 provides access to a cylindrical cavity partially defined by interior circumferential wall 362 having a diameter large enough to accommodate the ratchet tube 104. In exemplary form, the proximal end 360 of the second tube 350 is inserted through the distal opening 156 of the ratchet box 102 and longitudinally repositioned until the proximal end 360 contacts the distal flange 162 on the inside of the ratchet box. It should be noted that the internal diameter of the second cylindrical interior wall 160 of the ratchet box 102 is slightly less than the external diameter of the second tube 350, thereby securing the second tube to the ratchet box via a friction fit.

The longitudinal profile of the second tube 350 is substantially constant until it changes when approximately reaching the distal end 356. Proximate the distal end 356, the interior circumferential wall 362 terminates at an internal, ring-shaped flange 366 operative to change the cross-section of the cavity. In particular, the flange 360 includes a central opening that feeds into a cylindrical cavity having a diameter less than that of the interior circumferential wall 362. This smaller diameter cylindrical cavity is partially defined by a threaded circumferential surface 370 that is adapted to engage a threaded circumferential surface 374 of a second ball joint 380. In contrast to the first ball joint 320 (see FIG. 2) that includes a female connection comprising a hollow cylinder having an internal circumferential surface 328 that is threaded, this second ball joint 380 include a male connection comprising an external circumferential surface 374 threaded to fit within and engage the threaded circumferential surface 370 of the smaller diameter cylindrical cavity of the second tube 350.

The second ball joint 380 comprises a spherical ball end 382 integrally formed with the male connection. This spherical ball end 382 of the ball joint 380 is rotationally and pivotally repositionable with respect to a socket cooperatively formed by a ball joint housing 390 and a ball joint cap 394. In exemplary form, the ball joint housing 390 comprises a casing that partially encapsulates the spherical ball end 382 of the ball joint 380. On the interior of this casing is a semispherical depression that provides a bearing surface against which the spherical ball end 382 rotates and pivots. The ball joint housing 390 also includes a circular ring 396 integrally formed with the casing and having a diameter greater than the diameter of the spherical ball end 382. In order to retain the spherical ball end 382 within the ball joint housing 390, as well as selectively removing the spherical ball end from within the ball joint housing, the circular ring includes threads 400 that are adapted to engage threads 402 of the ball joint cap 394 to secure the ball joint cap to the ball joint housing.

As shown in FIG. 17, the ball joint cap 394 is ring-shaped and includes a central opening defined by an arcuate circumferential surface 404. This arcuate circumferential surface 404 cooperates with the semispherical depression of the ball joint housing 390 to create the spherical socket within which the spherical ball end 382 is able to rotate and pivot. In this exemplary embodiment, the diameter of the central opening of the ball joint cap 394 is less than the diameter of the spherical ball end 382 within the ball joint housing 390 so that once the ball joint cap and ball joint housing are mounted to one another with the spherical ball end 382 located therein, removal of the spherical ball end is not possible without discontinuing the ball joint cap from being mounted to ball joint housing.

Referencing FIGS. 18-28, a second exemplary ratcheting strut 500 makes use of several component parts of the first exemplary ratcheting strut 100. For example, the second ratcheting strut 500 uses the same tube mount 220, the threaded post 284, the post cap 306, the friction sleeve 316, the ball joint 320, the second tube 350, and the ball joint 380. Accordingly, a detailed description of these components has been omitted as part of discussing the second exemplary ratcheting strut 500 to omit redundancy, thereby furthering brevity.

This second exemplary ratcheting strut 500 includes a ratchet box. 502 having a longitudinal opening extending therethrough that accommodates throughput of a ratchet tube 504. In exemplary form, the longitudinal opening is partially defined by a pair of arcuate interior walls 506 (partial cylindrical) circumferentially interposed a pair of planar walls 508. The planar walls 508 are parallel to one another and spaced apart from one another a first predetermined distance that is less than a distance (in effect, the diameter of a cylinder the arcuate walls would be a part of) the arcuate walls 506 are spaced apart from one another. In this fashion, the planar walls 508 operate to narrow the vertical cross-section in comparison to a hollow cylindrical cavity. Working together, the arcuate walls 506 and the planar walls 508 allow longitudinal traversal of the ratchet tube 504, while inhibiting axial rotation of the ratchet tube.

In this exemplary embodiment, the ratchet tube 504 comprises a cylindrical ring body having a cylindrical exterior surface 520 axially outset from a cylindrical interior surface 522. In this manner, the interior of the ratchet tube 504 is hollow and has a constant vertical, circular cross-section along its longitudinal length. An exterior surface of the ratchet tube 504 includes the cylindrical exterior surface 520, as well as a pair of planar surfaces 524 extending longitudinally along a majority of the longitudinal length of the ratchet tube. In exemplary form, these planar surfaces 524 may be formed by planarizing opposing sides of the ring body (i.e., hollow cylindrical tube) to remove material from the outside of the ring body, thereby decreasing the wall thickness of the ring body, but not impacting the dimensions of the cylindrical interior surface 522. In exemplary form, the material removed from the ring body can be cross-sectionally represented as a first area outlined by a first chord extending between circumferential exterior points at zero degrees and ninety degrees and by the circumferential surface extending between the same points at zero degrees and ninety degrees. Similarly, the second area may be outlined by a second chord extending between one hundred eighty degrees and two hundred seventy degrees and by the circumferential surface extending between the same points at one hundred eighty degrees and two hundred seventy degrees. The planar surfaces 524, in exemplary form, do not extend along the entire longitudinal length of the ratchet tube 504 so that a distal end 526 of the ratchet tube is cylindrical, while the opposing proximal end 528 of the ratchet tube is partially cylindrical. More specifically, a pair of arcuate surfaces 532, 534 extends between the planar surfaces 524 to partially define the exterior of the ratchet tube. Each arcuate surface 532, 534 is separated from the other cylindrical surface by approximately ninety rotational degrees, except for the distal end where the arcuate surfaces seamlessly intersect with the cylindrical exterior surface 520. Both the dorsal and ventral arcuate surfaces 532 include a series of angled depressions 536 that are longitudinally repeated and consistently spaced apart from one another, thereby resulting in a series of angled teeth 538 that are longitudinally inset from the distal and proximal ends 526, 528 of the ratchet tube 504. In exemplary form, each tooth 538 includes a vertical surface 544 and an inclined surface 546 that intersects the vertical surface to form a horizontal peak 548. As will be discussed in more detail hereafter, the angled nature of the inclined surfaces 546 cooperate with corresponding surfaces of a pair of repositionable levers 570A, 570B to allow ratcheting action between the levers and the ratchet tube 504.

The shape of the ratchet tube 504 allows it to be inserted into the longitudinal opening of the ratchet box 502 so that the proximal end 528 of the ratchet tube is inserted into a distal opening 554 of the ratchet box 502 and extends through a proximal opening 556 prior to insertion of the distal end 526 into the interior of the ratchet box. The distal opening 554 is defined by a cylindrical interior wall 560 having a diameter larger than the arcuate interior walls 506. This cylindrical interior wall 560 extends proximally until terminating at a distal flange 562 that extends between the cylindrical interior wall and the arcuate interior walls 506. It should be noted that the cylindrical interior wall 560 and the arcuate interior walls 506 are coaxial with one another.

In this exemplary embodiment, the distal flange 560 is operative to inhibit throughput of objects having a cross-sectional distance larger than the distance between the planar walls 508. As mentioned previously, the distal end 526 of the ratchet tube 504 is cylindrical and exhibits a constant exterior diameter, whereas the proximal end 528 and a majority of the longitudinal length of the ratchet tube exhibits a cross-section that is partially circular with respect to the arcuate surfaces 532, 534, but is partially rectangular with respect to the planar surfaces 524. This dual shape (circular and rectangular) profile is also consistent with the dual shape profile on the interior walls 506, 508 of the ratchet box 102. In exemplary form, the exterior diameter (between the arcuate surfaces 532, 534) of the ratchet tube 504 is slightly less than the internal diameter of the arcuate interior walls 506. Likewise, the horizontal width between the planar surfaces 508 is slightly larger than the horizontal distance between the planar surfaces 524. As a result, the proximal end 528 of the ratchet tube 504 is able to be longitudinally repositioned along the entire length of the longitudinal opening of the ratchet box 502, whereas the distal end 526 of the ratchet tube is able to be longitudinally repositioned within only a portion of the longitudinal opening because the distal end cannot pass beyond the distal flange 562. In this manner, when the proximal end 528 of the ratchet tube 504 is first inserted into the distal opening 554 of the ratchet box 502 and longitudinally repositioned proximally, eventually the distal end 526 of the ratchet tube (where the planar surfaces 524 terminate and the uniform circumferential surface begins) abuts the distal flange 562, which prohibit further proximal motion of the ratchet tube.

In order to fix the position of the ratchet tube 504 with respect to the ratchet box 502, two levers 570A, 570B are repositionably mounted to the ratchet box to selectively engage the ratchet tube. More specifically, each lever 570A, 570B comprises an L-shaped beam 572 having a cylindrical pivot orifice 574 that accepts a dowel 576 concurrently seated within a respective cylindrical dowel orifice 578 in order to mount the ratchet box 502 to the lever. In exemplary form, each dowel 576 is cylindrical and has an external diameter that is slightly larger than the internal diameter of the corresponding cylindrical dowel orifice 578, thus securing the dowel in position via a friction fit. In contrast, the diameter of the corresponding cylindrical pivot orifice 574 is slightly larger than the external diameter of the respective dowel 576, thereby allowing pivoting motion of the lever 570A, 570B around the dowel.

In this exemplary embodiment, each lever 570A, 570B is biased by a spring 580 to engage the ratchet tube 504. More specifically, the coil spring 580 is seated within a respective spring receiver 582 of the ratchet box 502. Each spring receiver 582 comprises a ring-shaped depression that circumscribes a cylindrical projection that is adapted to be partially inserted into one end of the coil spring 580. Similarly, the underside of the lever 570S, 570B also includes a spring receiver 584 that likewise comprises a ring-shaped depression that circumscribes a cylindrical projection adapted to be partially inserted into the other end of the coil spring 580. The bias of the coil spring 580 is selected or set so that when no affirmative pressure is applied by a user to the lever 570A, 570B, a head 588 of the lever contacts the ratchet tube 504. In exemplary form, the head 588 of each lever 570A, 570B includes a series of angled teeth 592 that are each formed by the interaction of a vertical surface 594 and an inclined surface 596 that intersects the proximal surface to form a horizontal peak 598. In this fashion, the angled teeth 592 of each lever 570A, 570B are inclined to match the incline of the angled teeth 538 of the ratchet tube 504 nearest to each lever. As a result, when no affirmative pressure is applied by a user to the lever 570A, the ratchet tube 504 may not be repositioned proximally because the other lever 570B inhibits travel as the vertical surfaces 594 of the lever 570B teeth 592 contact the vertical surfaces 544 of the ratchet tube 504 lower teeth 538. Likewise, when no affirmative pressure is applied by a user to the lever 570B, the ratchet tube 504 may not be repositioned distally because the other lever 570A inhibits travel as the vertical surfaces 594 of the lever 570A teeth 592 contact the vertical surfaces 544 of the ratchet tube 504 upper teeth 538. As a result, in order to reposition the ratchet tube 504 proximally, a user needs to apply an affirmative pressure to the lever 570B to overcome the spring bias of the spring 580 and vertically separate the vertical surfaces 594 of the lever 570B teeth 592 with the vertical surfaces 544 of the ratchet tube 504 lower teeth 538. It does not matter that the other lever 570A continues to engage the ratchet tube 504 because the inclined surfaces 596 of the teeth 592 of the other lever 570A are engaging the inclined surfaces 546 of the upper teeth 538, thereby allowing the inclined surfaces 546, 596 to slide against one another so that the ratchet tube 504 may be repositioned proximally. When the appropriate proximal travel is reached, the user simply discontinues affirmative pressure to the lever 570B, thereby allowing the spring 580 bias to dominate and cause the lever 570B to contact the ratchet tube 504 so that the vertical surfaces 144, 194 contact one another and do not allow proximal motion. Conversely, in order to reposition the ratchet tube 504 distally, a user needs to apply an affirmative pressure to the lever 570A to overcome the spring bias of the spring 580 and vertically separate the vertical surfaces 594 of the lever 570A teeth 592 with the vertical surfaces 544 of the ratchet tube 504 upper teeth 538. It does not matter that the other lever 570B continues to engage the ratchet tube 504 because the inclined surfaces 596 of the teeth 592 of the other lever 570B are engaging the inclined surfaces 546 of the lower teeth 538, thereby allowing the inclined surfaces 546, 596 to slide against one another so that the ratchet tube 504 may be repositioned distally. When the appropriate distal travel is reached, the user simply discontinues affirmative pressure to the lever 570A, thereby allowing the spring 580 bias to dominate and cause the lever 570A to contact the ratchet tube 504 so that the vertical surfaces 144, 194 contact one another and do not allow distal motion.

Each lever 570A, 570B may also be locked in position so that the teeth 592 engage the angled teeth 538 of the ratchet tube 504. In order to lock either lever 570A, 570B in an engaged position with the ratchet tube 504, the lever includes a lock orifice 600 that is sized to receive a portion of a thumb screw 204. The thumb screw 204 includes a knob 206 mounted to a perpendicularly extending, linear projection 208 having threads 210 adapted to engage threads (not shown) on the inside of a thumb screw orifice 614 extending through the ratchet box 102. When the projection 208 of the thumb screw 204 is inserted through the thumb screw orifice 614 and lock orifice 600 for a respective lever, the lever 570A, 570B is not pivotally repositionable so that the teeth 592 of the lever are out of the line of travel of the teeth 538 of the ratchet tube 504. Consequently, to pivot either lever 570A, 570B so that the teeth 592 of the lever are out of the line of travel of the teeth 538 of the ratchet gibe 504, the thumb screw 204 needs to be positioned so that the projection 208 is no longer received within the lock orifice 600. After the thumb screw 204 is positioned so that the projection 208 is no longer received within the lock orifice 600, the lever 570A, 570B may be repositioned by application of affirmative pressure to overcome the bias of the spring 580, thereby pivoting the lever so that the teeth 592 of the lever are out of the line of travel of the teeth 538 of the ratchet tube 504.

When the ratchet tube 504 is repositioned with respect to the ratchet box 502, other components mounted to the ratchet tube are also repositioned. In this exemplary embodiment, a tube mount 220 is coupled to the proximal end 528 of the ratchet tube via a friction fit. A nut 650 is mounted to the tube mount 220 and is rotationally repositionable with respect thereto. The nut 650 includes one or more through set screw orifices 652 that extend from an exterior surface 654 into a hollow interior 658, which includes proximal and distal openings 660, 662. The exterior surface 654 comprises a hexagonal pattern of six alternating arcuate troughs 656 and six arcuate projections 658 that provide grip for a user to grasp the nut 650 and facilitate rotation of the nut with respect to the sleeve 236 of the tube mount 220. In this exemplary embodiment, the distal opening 662 allows access to a cylindrical cavity defined by a circumferential interior wall 670. At the proximal end of this interior wall 678 is a flange 672 that provides an abutment surface against which the exposed proximal end of the sleeve 236 contacts when fully seated within the nut 650. The flange 672 also operates to decrease the diameter of the hollow interior 658 and abuts a cylindrical interior surface 674 having threads 676 adapted to be engaged by the threads 298 of the threaded post 284 that extends through the nut 650, the tube mount 220, and partially through an interior of the ratchet tube 504. It is these partial threads 298 that are adapted to engage the threads 676 of the nut 650 so that rotational repositioning of the nut results in longitudinal repositioning of the threaded post 284. More specifically, clockwise rotation of the nut 650 may reposition the threaded post 284 longitudinally in a distal direction, while clockwise rotation of the nut 650 may reposition the threaded post 284 longitudinally in a proximal direction, or vice versa.

As with the first exemplary ratcheting strut 100, this second exemplary ratcheting strut 500 includes a ball joint 320 mounted to the threaded post 284. Similarly, this second exemplary ratcheting strut 500 also includes a second tube 350 mounted to the ratchet box 502 and a ball joint 380 mounted to the second tube. For purposes of illustration only with respect to this second exemplary ratcheting strut 500, the ball joint housing and ball joint cap for each ball joint 320, 380 have been omitted. Nevertheless, it is to be understood that the second exemplary ratcheting strut 500 includes a ball joint housing and a ball joint cap for each ball joint 320, 380.

Referencing FIGS. 29-34, a third exemplary ratcheting strut 700 makes use of several component parts of the first exemplary ratcheting strut 100. For example, the third ratcheting strut 700 uses the same ratchet tube 104, repositionable lever 170, tube mount 220, nut 250, post cap 306, friction sleeve 316, ball joint 320, ball joint housings 330, 390, ball joint caps 334, 394, second tube 350, and ball joint 380. Accordingly, a detailed description of these components has been omitted as part of discussing the third exemplary ratcheting strut 700 to omit redundancy, thereby furthering brevity. Essentially, the third exemplary ratcheting strut 700 differs from the first exemplary ratcheting strut 100 by the ratchet box 702 and threaded post 704.

This third exemplary ratcheting strut 700 includes a ratchet box 702 having a longitudinal opening extending therethrough that accommodates throughput of a ratchet tube 104. In exemplary form, the longitudinal opening is partially defined by a pair of arcuate interior walls 706 (partial cylindrical) circumferentially interposed a pair of planar walls 708. The planar walls 708 are parallel to one another and spaced apart from one another a first predetermined distance that is less than a distance (in effect, the diameter of a cylinder the arcuate walls would be a part of) the arcuate walls 706 are spaced apart from one another. In this fashion, the planar walls 708 operate to narrow the vertical cross-section in comparison to a hollow cylindrical cavity. Working together, the arcuate walls 706 and the planar walls 708 allow longitudinal traversal of the ratchet tube 104, while inhibiting axial rotation of the ratchet tube.

The shape of the ratchet tube 104 allows it to be inserted into the longitudinal opening of the ratchet box 702 so that the proximal end 128 of the ratchet tube is inserted into a distal opening 712 of the ratchet box 702 and extends through a proximal opening 714 prior to insertion of the distal end 126 into the interior of the ratchet box.

In this exemplary embodiment, the dimensions of the distal and proximal openings 712, 714 are operative to inhibit complete throughput of objects having a cross-sectional distance larger than the distance between the planar walls 708. Because the distal end 126 of the ratchet tube 104 is cylindrical and exhibits a constant exterior diameter, whereas the proximal end 128 and a majority of the longitudinal length of the ratchet tube exhibits a cross-section that is partially circular with respect to the arcuate surfaces 132, 134, but is partially rectangular with respect to the planar surfaces 124. This dual shape (circular and rectangular) profile is also consistent with the dual shape profile on the interior walls 706, 708 of the ratchet box 702. In exemplary form, the exterior diameter (between the arcuate surfaces 132, 134) of the ratchet tube 104 is slightly less than the internal diameter of the arcuate interior walls 706. Likewise, the horizontal width between the planar surfaces 708 is slightly larger than the horizontal distance between the planar surfaces 124. As a result, the proximal end 128 of the ratchet tube 104 is able to be longitudinally repositioned along the entire length of the longitudinal opening of the ratchet box 702, whereas the distal end 126 of the ratchet tube is able to be longitudinally repositioned within only a portion of the longitudinal opening because the distal end cannot pass into the interior of the ratchet box. In this manner, when the proximal end 128 of the ratchet tube 104 is first inserted into the distal opening 712 of the ratchet box 702 and longitudinally repositioned proximally, eventually the distal end 126 of the ratchet tube (where the planar surfaces 124 terminate and the uniform circumferential surface begins) abuts the outside of the ratchet box, which prohibits further proximal motion of the ratchet tube.

In order to fix the position of the ratchet tube 104 with respect to the ratchet box 702, a lever 170 is repositionably mounted to the ratchet box to selectively engage the ratchet tube. Reference is had to the previous discussion of how the ratchet tube 104 and 170 interact to allow or retard repositioning of the ratchet tube.

When the ratchet tube 104 is repositioned with respect to the ratchet box 702, other components mounted to the ratchet tube are also repositioned. In this exemplary embodiment, a tube mount 220 is coupled to the proximal end 128 of the ratchet tube via a friction fit. A nut 250 is mounted to the tube mount 220 and is rotationally repositionable with respect thereto. The nut 250 includes threads 276 that engage threads 718 of the threaded post 704 while the threaded post extends through the nut, the tube mount 220, and partially through an interior of the ratchet tube 104. It is these threads 718 that are adapted to engage the threads 276 of the nut 250 so that rotational repositioning of the nut results in longitudinal repositioning of the threaded post 704.

In exemplary form, the threaded post 704 comprises a hybrid exterior surface comprising a pair of arcuate surfaces 720 that are interposed by a pair of planar surfaces 722 extending longitudinally along the longitudinal length of the threaded post. In exemplary form, these planar surfaces 722 may be formed by planarizing opposing sides of a cylinder to remove material from the exterior, thereby decreasing the thickness of the cylinder at certain circumferential locations. In exemplary form, the material removed from the cylinder can be cross-sectionally represented as a first area outlined by a first chord extending between circumferential exterior points at zero degrees and ninety degrees and by the circumferential surface extending between the same points at zero degrees and ninety degrees. Similarly, the second area may be outlined by a second chord extending between one hundred eighty degrees and two hundred seventy degrees and by the circumferential surface extending between the same points at one hundred eighty degrees and two hundred seventy degrees. Both arcuate surfaces 720 are tapped to provide a series of repeating threads 718. It is these threads 718 that are adapted to engage the tapped surfaces 276 of the nut 250 so that rotational repositioning of the nut results in longitudinal repositioning of the threaded post 704. More specifically, clockwise rotation of the nut 250 may reposition the threaded post 704 longitudinally in a distal direction, while clockwise rotation of the nut 250 may reposition the threaded post 704 longitudinally in a proximal direction, or vice versa.

A distal end 724 of the threaded post 704 includes a cylindrical cavity that is tapped to provide internal threads 726. These threads 726 are adapted to be engaged by the threads 304 of the post cap 306, which is mounted to the friction sleeve 316. As discussed previously, the diameter of the cylindrical interior surface 122 of the ratchet tube 104 is slightly less than the exterior diameter of the friction sleeve 316, thereby allowing the post cap and friction sleeve to slide longitudinally within the interior of the ratchet tube, but with a predetermined resistance. But this frictional resistance is not so great as to inhibit longitudinal motion of the sleeve 316, the post cap 306, and threaded post 704 when the nut 250 is rotated.

A proximal end 730 of the threaded post 704 is mounted to a ball joint 320 having a spherical ball end 322 integrally formed with a hollow cylinder 324. The hollow cylinder is threaded and these threads 328 are adapted to engage the threads 718 of the threaded post 704 in order to mount the threaded post to the ball joint 320 via a friction fit. Similar to the first exemplary ratcheting strut 100, this third ratcheting strut also includes a ball joint housing 330 and a ball joint cap 334.

Referring back to FIGS. 32 and 33, the ratchet box 702 includes a cylindrical cavity 732 that extends in parallel to, but is offset from, the longitudinal opening. This cylindrical cavity is adapted to receive a portion of the second tube 250 and is bounded by a cylindrical interior wall 734 that abuts a circular, planar wall 736. In exemplary form, the diameter of the cylindrical interior wall 734 is slightly less than the exterior diameter of the second tube 250, thereby mounting the ratchet box 702 to the second tube once an end of the second tube is inserted deep enough to abut the planar wall.

As with the first exemplary ratcheting strut 100, the second tube 250 of the third exemplary ratcheting strut 700 is mounted to a ball joint 380 that includes a male connection comprising an external circumferential surface 374 threaded to fit within and engage the threaded circumferential surface 370 of the smaller diameter cylindrical cavity of the second tube 350. Likewise, this third ratcheting strut 700 also includes a ball joint housing 330 and a ball joint cap 334.

Unlike the previous two exemplary ratcheting struts 100, 500 that included ratcheting structures that were coaxial with the second tube 350, this third exemplary ratcheting strut 700 has the ratcheting structures axially offset, but in parallel with, the second tube. This offset orientation has the advantages of allowing more adjustable length, allowing use of solid bodies, easier manufacture, and increased strength.

Referring to FIGS. 34-54, a fourth exemplary ratcheting strut 800 comprises a ratchet box 802 having a longitudinal opening extending therethrough that accommodates throughput of a ratchet tube 804. In exemplary form, the longitudinal opening is partially defined by a first cylindrical interior wall 806 having a first diameter. A series of plateaus 810, 812 extend from the interior wall 806 and into the interior of the longitudinal opening, thereby decreasing the cross-sectional area of the opening. In particular, each plateau 810, 812 extends perpendicularly from the interior wall and opposite one another. Each plateau 810, 812 includes an arcuate edge that matches the arcuate contour of the interior wall 806 and an innermost edge comprising a geometric chord, where the horizontal cross-section of the interior wall 806 would otherwise be circular. In this exemplary embodiment, the plateaus 810, 812 are diametrically positioned opposite one another to create a horizontal cross-section having a constant width therebetween. Working together, the interior wall 806 and plateaus 810, 812 allow longitudinal traversal of the ratchet tube 804, while inhibiting axial rotation of the ratchet tube.

Figure 40:
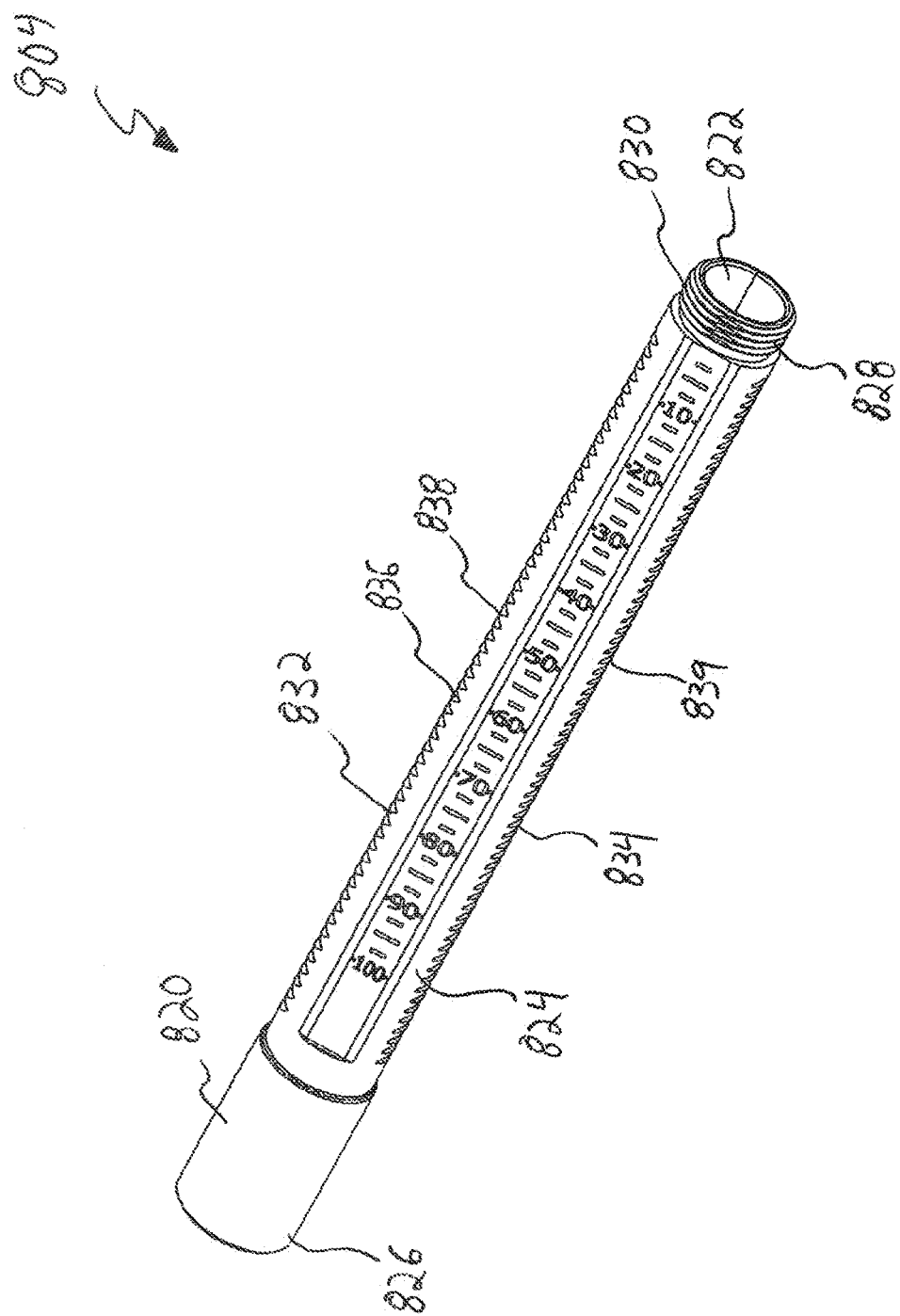
FIG. 40 is an elevated perspective view of an exemplary ratchet tube as utilized in the exemplary ratcheting strut of FIG. 35.
Figure 41:
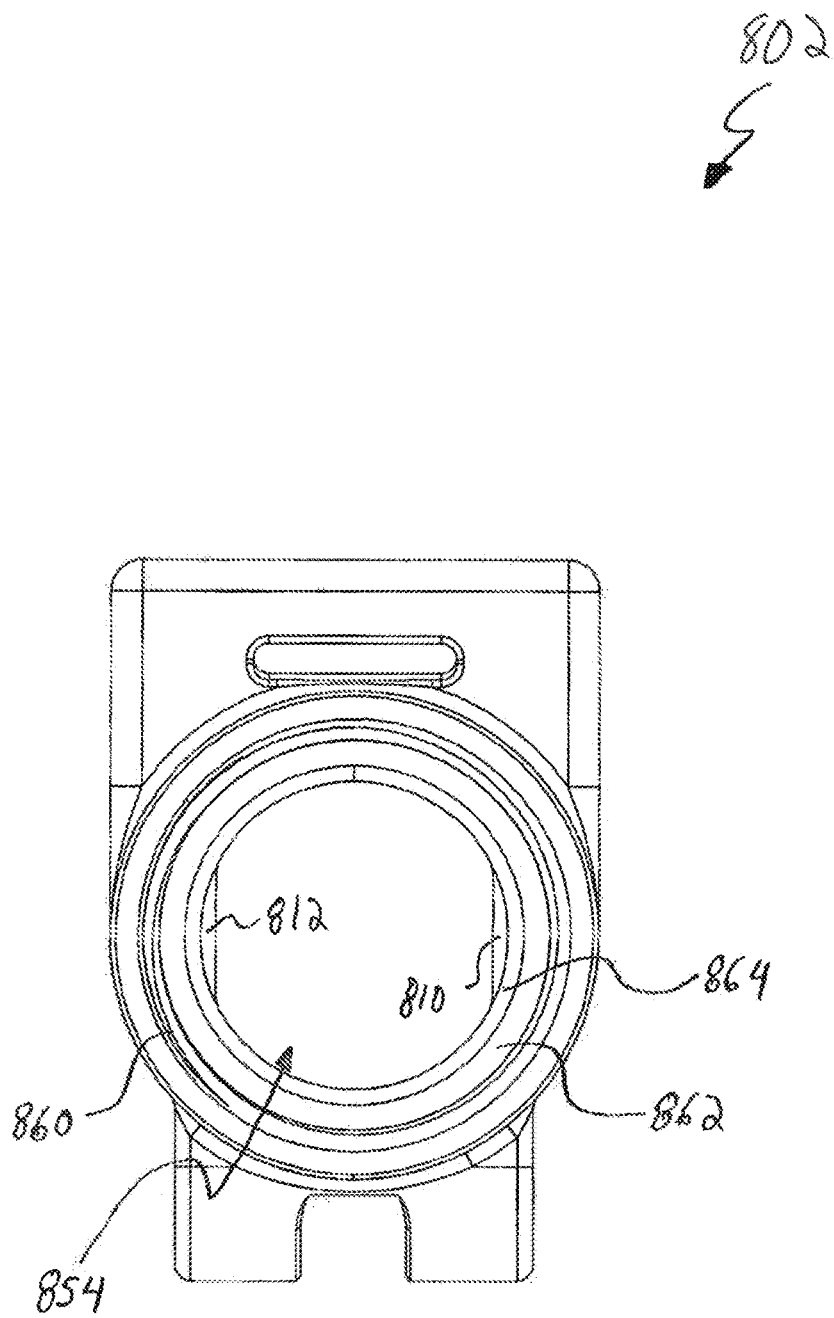
FIG. 41 is a distal, profile view of the exemplary ratchet box shown in FIG. 35.
Figure 43:
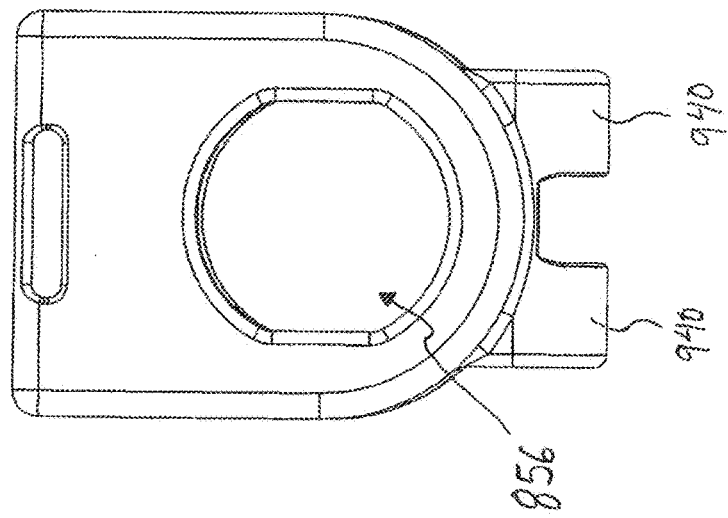
FIG. 43 is a cross-sectional view of the exemplary ratchet box and its components with respect to the exemplary ratchet tube taken vertically and along the longitudinal axis.
Figure 43:
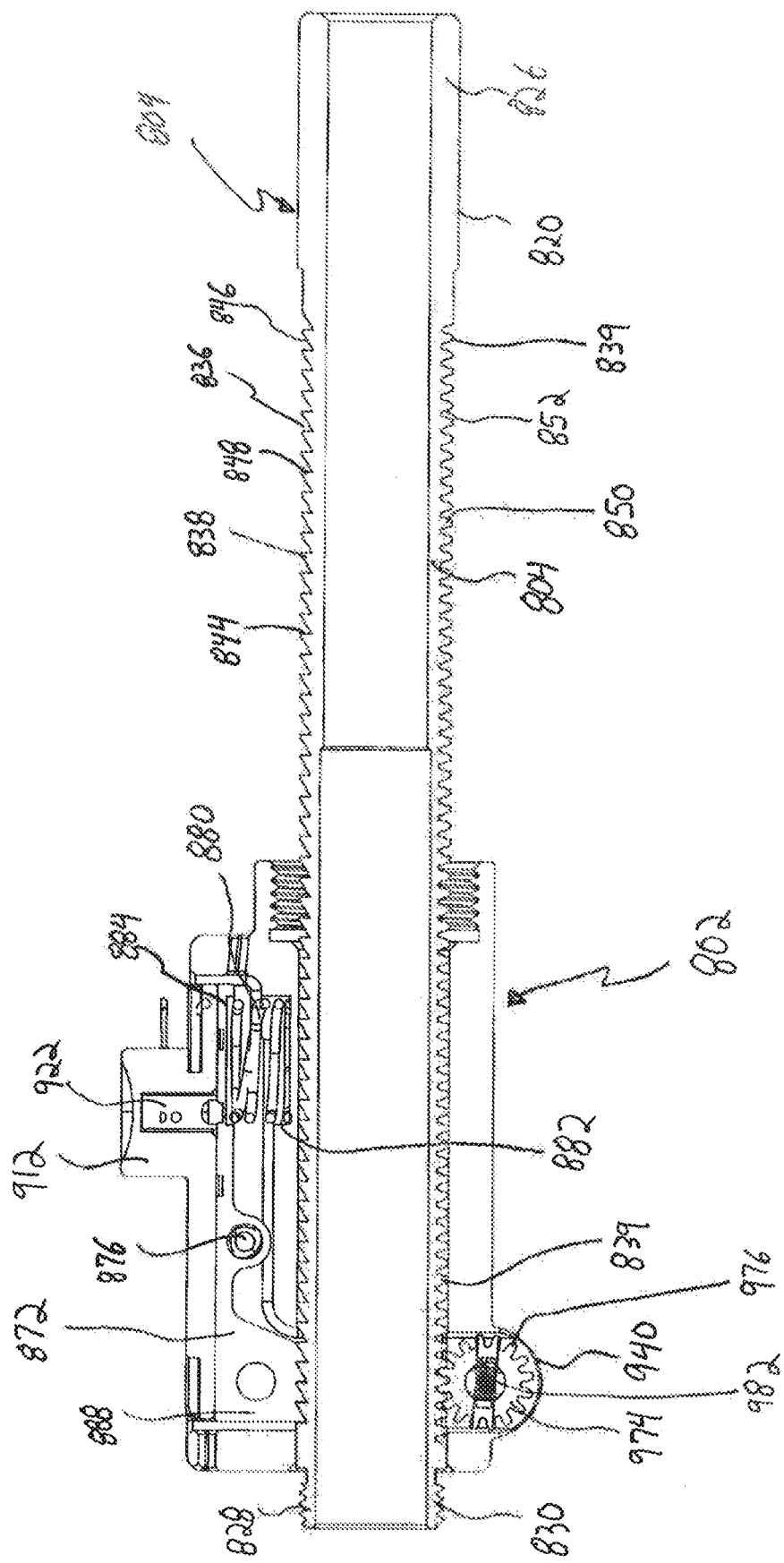
Figure 44:
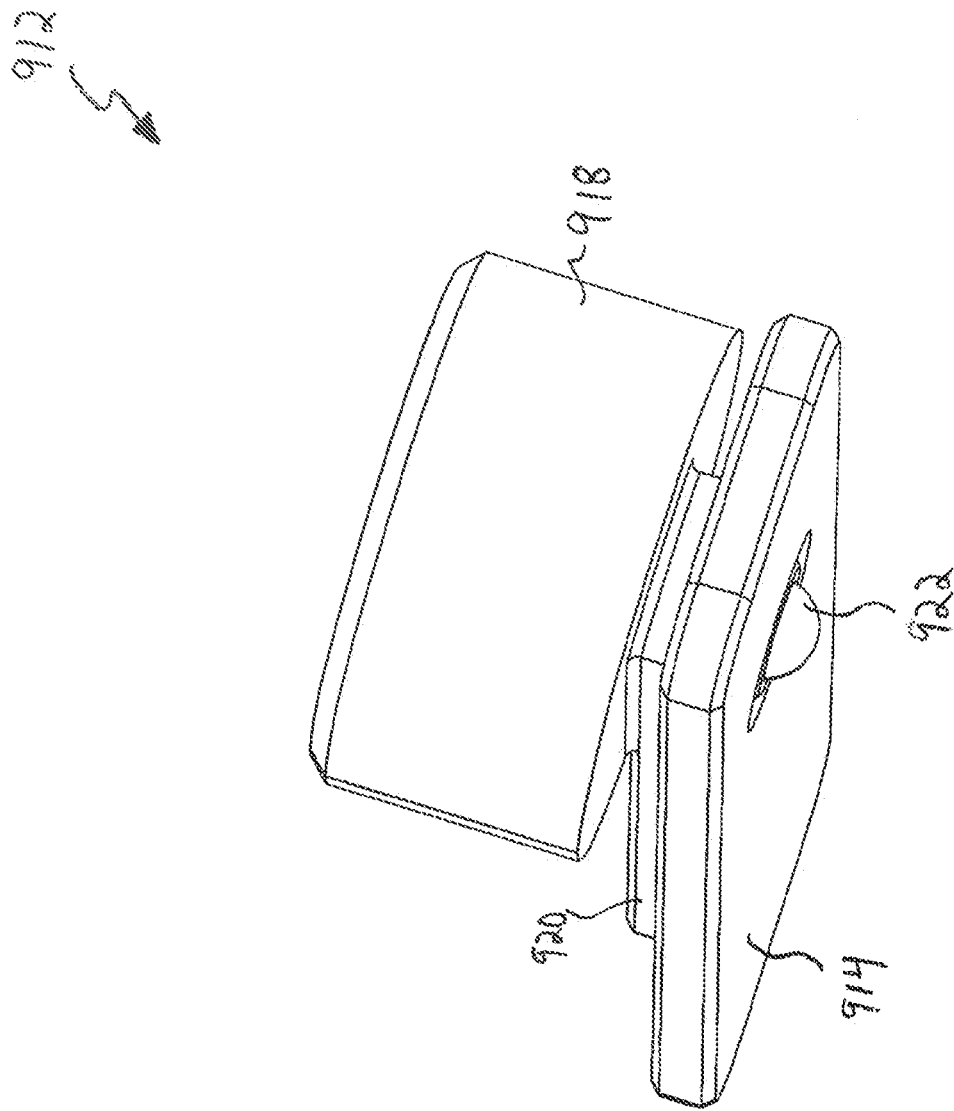
FIG. 44 is an underneath perspective view of the exemplary button shown in FIG. 35.
Figure 45:
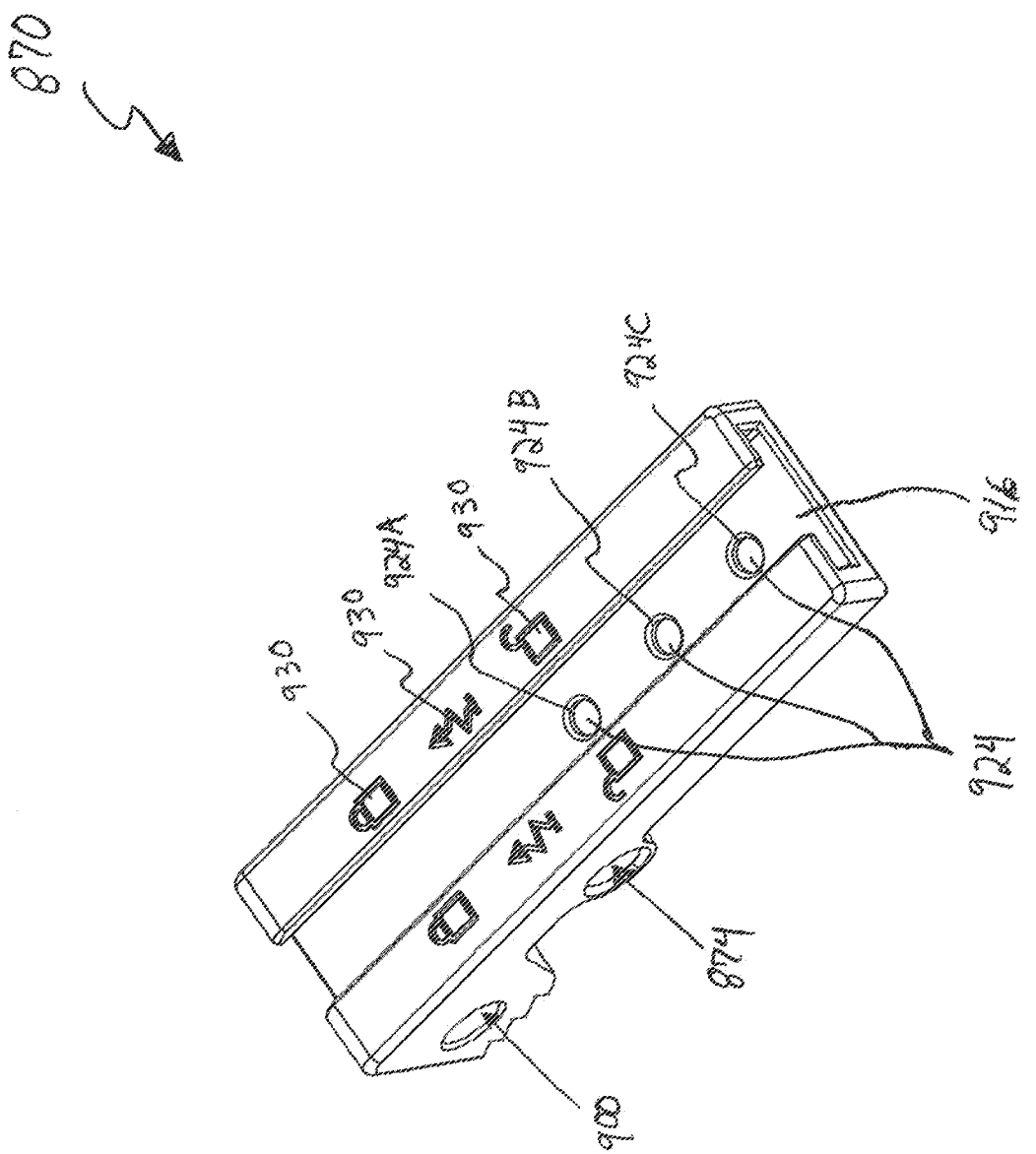
FIG. 45 is an elevated perspective view of the exemplary lever shown in FIG. 35.
Figure 46:
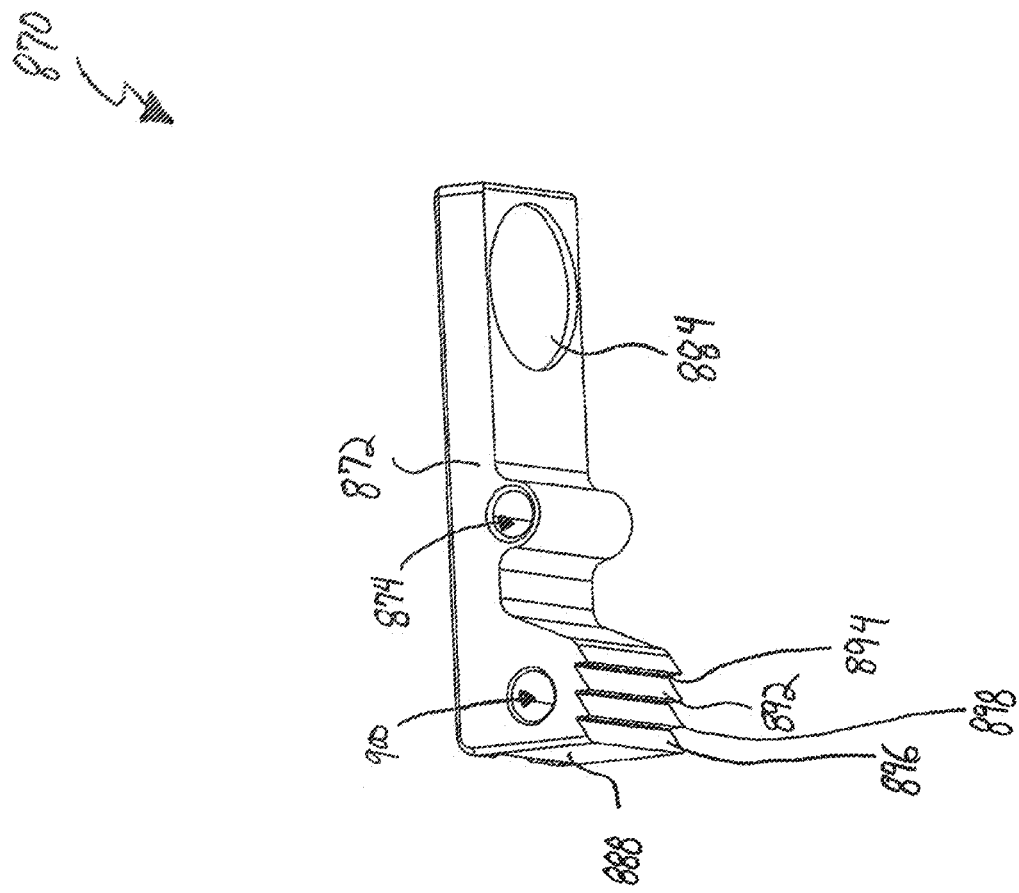
FIG. 46 is an underneath perspective view of the exemplary lever shown in FIG. 35.
Figure 47:
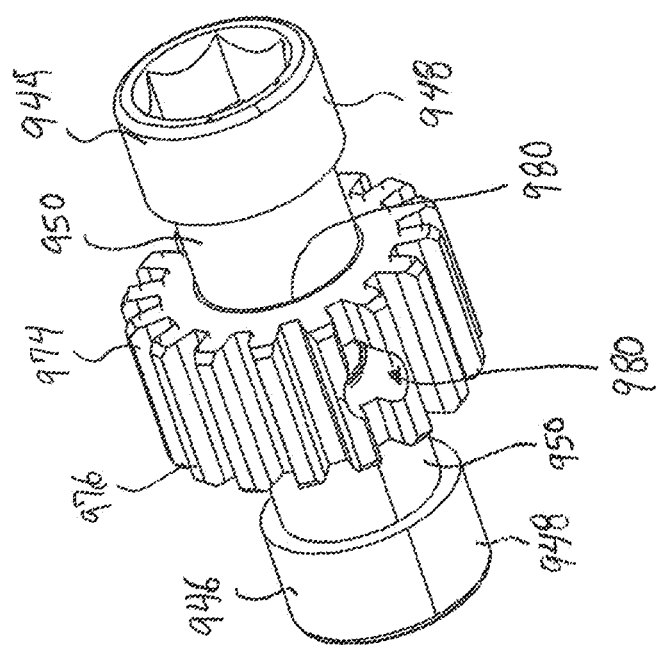
FIG. 47 is an elevated perspective view of a gear and gear shaft shown in FIG. 35
Figure 48:
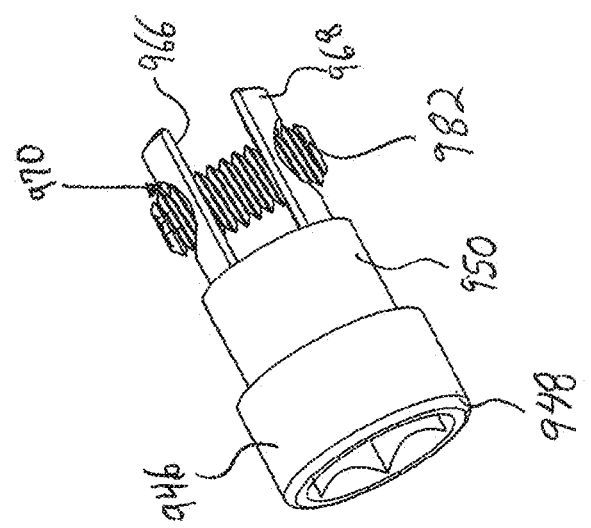
FIG. 48 is a complimentary half of the gear shaft of FIG. 47.
Figure 49:
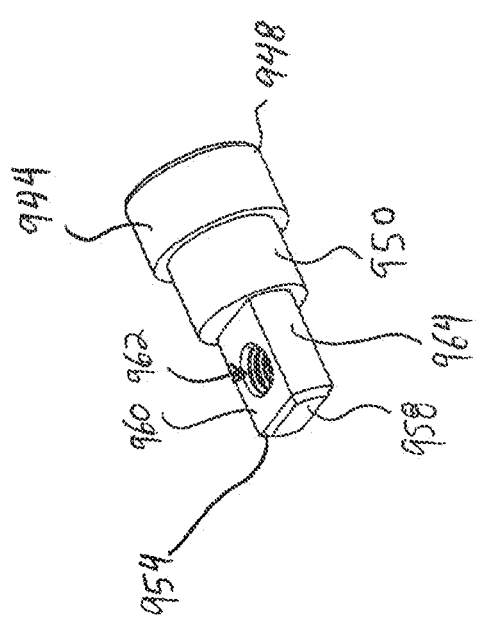
FIG. 49 is the other complimentary half of the gear shaft of FIG. 47.

As shown in FIG. 40, the ratchet tube 804 comprises a cylindrical ring body having a cylindrical exterior surface 820 axially outset from a cylindrical interior surface 822. In this manner, the interior of the ratchet tube 804 is hollow and has a vertical, circular cross-section along its longitudinal length. An exterior surface of the ratchet tube 804 includes the cylindrical exterior surface 820, as well as a pair of planar surfaces 824 extending longitudinally along a majority of the longitudinal length of the ratchet tube. In exemplary form, these planar surfaces 824 may be formed by planarizing opposing sides of the ring body (i.e., hollow cylindrical tube) to remove material from the outside of the ring body, thereby decreasing the wall thickness of the ring body, but not impacting the dimensions of the cylindrical interior surface 822. In addition, one or both planar surfaces 824 may include numerical or other indicia indicative of increments of longitudinal length. In this exemplary embodiment, the indicia include a series of numerals in increments of ten and vertical marks therebetween designating millimeter increments. In exemplary form, the material removed from the ring body can be cross-sectionally represented as a first area outlined by a first chord extending between circumferential exterior points at zero degrees and ninety degrees and by the circumferential surface extending between the same points at zero degrees and ninety degrees. Similarly, the second area may be outlined by a second chord extending between one hundred eighty degrees and two hundred seventy degrees and by the circumferential surface extending between the same points at one hundred eighty degrees and two hundred seventy degrees. The planar surfaces 824, in exemplary form, do not extend along the entire longitudinal length of the ratchet tube 804, therefore a distal end 826 of the ratchet tube is cylindrical, while the opposing proximal end 828 of the ratchet tube is also cylindrical and includes helical threads 830. Accordingly, the planar surfaces 824 interpose the opposing ends 826, 828. In addition, a pair of arcuate surfaces 832, 834 extends between the planar surfaces 824 to partially define the exterior of the ratchet tube in between the ends 826, 828. Each arcuate surface 832, 834 is separated from the other cylindrical surface by approximately ninety rotational degrees. Both arcuate surfaces 832, 834 include a series of depressions 836 that are longitudinally repeated and consistently spaced apart from one another to create a series of teeth 838 that are longitudinally inset from the distal and proximal ends 826, 828 of the ratchet tube 804. In exemplary form, each tooth 838 on the top arcuate surface 832 includes a vertical distal surface 844 and an inclined proximal surface 846 that intersects the distal surface to form a horizontal peak 848. As will be discussed in more detail hereafter, the inclined nature of the proximal surface 846 cooperates with a corresponding surface of a repositionable lever 870 to allow ratcheting action between the lever and the ratchet tube 804. In contrast, each tooth 839 on the bottom arcuate surface 834 includes alternating inclined proximal surfaces 850 and declined distal surfaces 852 to create a series of V-shaped teeth with V-shaped cavities therebetween.

Referring to FIGS. 37-43, the shape of the ratchet tube 804 allows it to be inserted into the longitudinal opening of the ratchet box 802 so that the proximal end 828 of the ratchet tube 804 is inserted through a distal opening 854 of the ratchet box 802 and also through a proximal opening 856 and extends through of the ratchet box. The distal opening 854 is defined by a second interior wall 860 having a diameter larger than the first cylindrical interior wall 806. This second interior wall 860 includes helical threads that extend proximally until terminating at a perpendicular distal flange 862 that transitions into a frustoconical flange 864. It should be noted that the interior walls 806, 860 and flanges 862, 864 are coaxial with one another. In this exemplary embodiment, the distal flange 862 is operative to inhibit throughput of objects having a diameter larger than the diameter of the first cylindrical interior wall 806. In addition, the plateaus 810, 812 located on the interior of the first cylindrical interior wall 806 change the longitudinal profile of the longitudinal opening and prohibit throughput of cylindrical objects having a diameter slightly less than the diameter of the first cylindrical interior wall. As mentioned previously, the distal end 826 of the ratchet tube 804 is cylindrical and exhibits a constant exterior diameter, whereas the proximal end 828 and a majority of the longitudinal length of the ratchet tube exhibits a cross-section that is circular with respect to the arcuate surfaces 832, 834, but is rectangular with respect to the planar surfaces 824 and a portion of the threads 830. This dual profile (circular and rectangular) is also consistent with the dual profile on the interior of the cylindrical interior wall 806 taking into account the plateaus 810, 812. In exemplary form, the exterior diameter (between the arcuate surfaces 832, 834) of the ratchet tube 804 is slightly less than the internal diameter of the cylindrical interior wall 806. Likewise, the horizontal width between the opposed plateaus 810, 812 is slightly larger than the horizontal distance between the planar surfaces 824. As a result, the proximal end 828 of the ratchet tube 804 is able to be longitudinally repositioned along the entire length of the longitudinal opening of the ratchet box 802, whereas the distal end 826 of the ratchet tube is not able to be longitudinally repositioned through the proximal opening 856, but is able to be repositioned through the distal opening 854, because the distal end cannot pass beyond the plateaus 810, 812. In this manner, when the proximal end 828 of the ratchet tube 804 is first inserted into the distal opening 854 of the ratchet box 802 and longitudinally repositioned proximally, eventually the distal end 826 of the ratchet tube (where the planar surfaces 824 terminate and the uniform circumferential surface 820 begins) abuts the plateaus 810, 812, which prohibit further proximal motion of the ratchet tube with respect to the ratchet box.

In order to fix the position of the ratchet tube 804 with respect to the ratchet box 802, a lever 870 is repositionably mounted to the ratchet box to selectively engage the ratchet tube. More specifically, the lever 870 comprises an L-shaped beam 872 having a cylindrical pivot orifice 874 that accepts a pivot screw 876 concurrently seated within a threaded wall 878 delineating a through orifice in order to pivotally mount the lever 870 to the ratchet box 802. In exemplary form, the screw 876 is cylindrical, threaded, and has an external diameter that is sized to threadably engage the threaded wall 878, thus securing the screw in position via a friction fit. In contrast, the diameter of the cylindrical pivot orifice 874 is slightly larger than the external diameter of the screw 876, thereby allowing pivoting motion of the lever 870 around the screw.

In this exemplary embodiment, the lever 870 is biased by a spring 880 to engage the ratchet tube 804. More specifically, the coil spring 880 is seated within a spring receiver 882 of the ratchet box 802. The spring receiver 882 comprises a cylindrical depression that circumscribes at least a portion of the coil spring 880. Similarly, the underside of the lever 870 also includes a spring receiver 884 that likewise comprises a cylindrical depression that circumscribes at least a portion of the coil spring 180 opposition the portion received within the spring receiver 882 of the ratchet box 802. The bias of the coil spring 880 is selected or set so that when no affirmative pressure is applied by a user to the lever 870, a head 888 of the lever contacts the ratchet tube 804. In exemplary form, the head 888 of the lever 870 includes a series of angled teeth 892 that are each formed by the interaction of a vertical distal surface 894 and an inclined proximal surface 896 that intersects the proximal surface to form a peak 898. In this fashion, the angled teeth 892 of the lever 870 are inclined to match the incline of the angled teeth 838 of the ratchet tube 804. As a result, when no affirmative pressure is applied by a user to the lever 870, the ratchet tube 804 may be repositioned proximally so that the inclined surfaces 846, 896 ride upon one another (and overcome the spring 880 bias to raise the lever 870) successively, thereby allowing the peaks 848, 898 to pass one another. In contrast, when no affirmative pressure is applied by a user to the lever 870, the ratchet tube 804 may not be repositioned distally because the vertical surfaces 844, 894 contact one another and do not allow distal motion because the lever remains in the line of travel of the ratchet tube. Accordingly, in order to reposition the ratchet tube 804 distally, a user needs to apply affirmative pressure to the lever 870 and overcome the spring 880 bias, thereby removing the lever from the line of travel of the ratchet tube. When the appropriate distal travel is reached, the user simply discontinues affirmative pressure to the lever 870, thereby allowing the spring 880 bias to dominate and cause the lever to contact the ratchet tube 804 so that the vertical surfaces 844, 894 contact one another and do not allow distal motion.

The lever 870 may also be locked in position so that the angled teeth 892 engage the angled teeth 838 of the ratchet tube 804. In order to lock the lever 870 in the position shown in FIG. 37, the lever includes a lock orifice 900 that is sized to receive a portion of a pin (not shown). The pin includes a knob mounted to a perpendicularly extending, linear projection. When the projection of the pin is inserted into and through a pin orifice 910 extending through the ratchet box 802 as well extending into the lock orifice 900, the lever 870 is not pivotally repositionable so that the teeth 892 of the lever are out of the line of travel of the teeth 838 of the ratchet tube 804. Consequently, to pivot the lever 870 and move the teeth 892 of the lever 870 out of the line of travel of the teeth 838 of the ratchet tube 804, the pin needs to be positioned so that the projection 908 is no longer concurrently received within the lock orifice 900 and the pin orifice 910.

Referencing FIGS. 37 and 44-46, after the pin is positioned so that the projection 908 is no longer received within the lock orifice 900, the lever 870 may be repositioned by application of affirmative pressure to a repositionable button 912. The repositionable button 912 includes a sled 914 that is configured to slide within a track 916 formed into the top of the lever 870. In this exemplary embodiment, the sled 914 includes a rectangular shape with four rounded corners and a cavity extending through the bottom of the sled and into a cylindrical knob 918 that is spaced apart from the sled via a rectangular mesa 920. The cavity is configured to receive a ball-point detent 922 having a spring biased ball that protrudes from the underside of the sled 914. In exemplary form, the sled 914 is configured to be received within the track 916 so that the sled may be repositioned longitudinally along the track. In particular, the mesa 920 is dimensioned to extend upward in between opposing walls of the lever 870 that delineate the track 916 so that the knob 918 appears to sit on top of these opposing walls.

A plurality of holes 924 extending through the lever 870 are longitudinally spaced apart in a generally straight line on the interior of the track 916. Each hole 924 is sized to at least partially receive the spring biased ball of the detent 922 when the detent is vertically positioned over a hole. In this manner, when a hole 924 receives at least a portion of the spring biased ball of the detent 922, this engagement is operative to retain the longitudinal position of the sled 914 with respect to the track 916.

In exemplary form, the positioning of the holes 924 corresponds to three different positions of the button 912 with respect to the lever 870 in order to vary the position of the teeth 892 with respect to the ratchet tube 804 teeth 838. In particular, these three positions are visually denoted by indicia 930 on the lever and a pointer 932 on the button 912 aligning with one another. By way of example, a first indicia 930 resembling a padlock in the locked position corresponds to the button 912 positioned so that the detent 922 engages the first hole 924A and a portion of the sled 914 is received within a proximal opening 928 of the ratchet box 802. When a portion of the sled 914 is received within the proximal opening 928, the size of the opening is operative to inhibit significant play between the button 912 and ratchet box 802, thereby inhibiting pivoting of the lever 870 in order to maintain the position of the teeth 892 in the line of travel of the ratchet tube 804 teeth 838. This action is operative to lock the longitudinal position of the ratchet box with respect to the ratchet tube. In contrast, a second indicia 930 resembling a jagged arrow corresponds to the button 912 positioned so that the detent 922 engages the second hole 924B and no portion of the sled 914 is received within either the proximal opening 928 or a distal opening 932 of the ratchet box 802. When the button 912 is in this second position, the lever 870 is able to be freely pivoted by a user depressing downward on the button to overcome the spring 880 bias and repositioning the teeth 892 of the lever 870 out of the line of travel of the ratchet tube 804 teeth 838. This action is operative to allow longitudinal repositioning of the ratchet box 802 with respect to the ratchet tube 804 in either direction. Likewise, if a user does not depress the button 912, the second position nonetheless allows the ratchet tube 804 to be repositioned proximally with respect to the ratchet box 902, but inhibits the ratchet tube from being repositioned distally with respect to the ratchet box. In other words, when the button 912 occupies the second position, which is a neutral position, the inclined proximal surfaces 846 of the ratchet tube teeth 838 may be operative to push against the inclined proximal surfaces 896 of the lever teeth 892 and overcome the spring 880 bias in order to reposition the ratchet tube 804 proximally with respect to the ratchet box 802. But distal motion of the ratchet tube 804 with respect to the ratchet box 802 is inhibited because of the interaction between the vertical surfaces 894 of the lever teeth 892 and the vertical surfaces 844 of the ratchet tube 804. Finally, a third indicia 930 resembling a padlock in the unlocked position corresponds to the button 912 positioned so that the detent 922 engages the third hole 924C and a distal portion of the sled 914 is received within the distal opening 932 of the ratchet box 802. The size of the distal opening 932 is operative to inhibit significant play between the button 912 and ratchet box 802, thereby inhibiting pivoting of the lever 870 in order to maintain the position of the teeth 892 out of the line of travel of the ratchet tube 804 teeth 838. This action is operative to allow longitudinal repositioning of the ratchet box 802 with respect to the ratchet tube 804.

Referring to FIGS. 43 and 47-49, other components mounted to the ratchet box 802 may also be repositioned in order to reposition the ratchet tube 804. Specifically, the ratchet box 802 includes a pair of gear shaft receivers 940 that each includes a gear shaft orifice 942, where the gear shaft orifices are axially aligned and receive complementary halves 944, 946 of a gear shaft. Each gear shaft half 944, 946 includes an enlarged cylindrical end 948 that includes a cavity contoured to receive a hexagonal driver (not shown). Inset from the cylindrical end 948 is a smaller diameter cylinder 950 having a smooth circumferential surface that acts as a bearing surface contacting an inner circumferential surface 952 of the gear shaft receivers 940. In this manner, the tear shaft halves 944, 946 are rotationally repositioned when positioned within the gear shaft receivers 940. Further inset from the smaller diameter cylinder 950 is a retention member 954, 956 that is differs for the two halves 944, 946. The first half 944 includes a rectangular flange 954 with a flat end 958, opposed planar top and bottom sides 960 with a threaded orifice 962 therethrough, and rounded lateral sides 964. The second half 946 includes a pair of projections 956 with a flat end and each having planar surfaces 966 that face one another. In addition, each projection 956 includes an outer surface 968 that is rounded and includes a threaded through hole 970 that is adapted to be axially aligned with the threaded through hole 962 of the other half 944. More specifically, the retention members 954, 956 cooperate and fit together to define a cylinder having a smaller diameter than the inset cylinder 950.

The smallest diameter cylinder is sized to extend into a repositionable gear 974. In exemplary form, the repositionable gear 974 includes a plurality of parallel splines 976 that are circumferentially distributed about a cylindrical base of the gear. Each spline 976 is identical and uniformly spaced apart from each other and from an inner circumferential cylindrical surface 980 that defines a cylindrical through opening configured to receive the smallest cylinder (i.e., the retention member 954, 956). In this exemplary embodiment, the splines 976 are sized and spaced apart from one another to be sequentially received within the depressions 836 on the lower row of teeth 838 extending along the ratchet tube 804. In this manner, as the ratchet tube 804 is repositioned longitudinally with respect to the ratchet box 802, the gear 974 rotates in one direction of the other depending upon whether the movement of the ratchet tube is in the proximal or distal direction. Not only does the gear 974 rotate, but so too do the complementary halves 944, 946 of the gear shaft, which are mounted to the gear. Specifically, the gear 974 includes a through hole 980 that is partially threaded and sized to receive a threaded pin 982. In particular, the threads of the through hole 980 match those of the retention member 954, 956 holes so that the threaded pin may be inserted into the holes 980, 970, 962 and correspondingly engage the retention members and gear to couple the components to one another.

Assembly of the gear 974 and gear shaft, as well as mounting the gear and gear shaft to the ratched box 802, includes positioning the gear to interpose the gear shaft receivers 940. Specifically, the ratchet box 802 includes a through opening 986 above and in between the gear shaft receivers 940 that is sized to accommodate at least partial insertion of the gear 974. More specifically, the gear 974 is inserted between the gear shaft receivers 940 so that at least some of the splines 976 extend through the opening 986 and into the interior of the ratchet box 802. As will be discussed in more detail hereafter, once assembled, the gear 974 is positioned so that the splines 976 may interface with the lower teeth 838 of the ratchet tube 804. The gear 974 is also positioned so that the through hole 980 is axially aligned with the gear shaft orifices 942. In this manner, after the gear 974 is in position, retention member 954, 956 of each gear shaft half 944, 946 is inserted through a respective gear shaft orifice 942 and through the through hole 980 so that the retention members form the smallest cylinder. In this orientation, rotation of one of the gear shaft halves 944, 946 correspondingly results in rotation of the other gear shaft half 944, 946, but does not necessarily result in rotation of the gear 974. To ensure rotation of the gear 974 when a gear shaft half 944, 946 is rotated, the through hole 980 of the gear is aligned with the holes 962, 970 extending through the gear shaft halves in order to accept insertion of the threaded pin 982. Consequently, the threaded pin 982 is inserted into the threaded holes to lock the position of the gear 974 with respect to the gear shaft halves. Thus, after the threaded pin 982 is inserted, rotation of a gear shaft half 944, 946 is also accompanied by rotation of the gear 974 and vice versa.

Referring back to FIGS. 34 and 38-43, the distal end of the ratchet box 802 includes a distal opening 856 defined by the second cylindrical interior wall 860, which ends proximally when it meets the distal flange 862. The distal opening is sized to accommodate throughput of the ratchet tube 804 as well as partial insertion of a second tube 1000 in order to mount the second tube to the ratchet box 802 using threaded engagement between helical threads 1002, which circumscribe a flanged lip 1004 of the second tube, and helical threads on the second interior wall 860 of the ratchet box. This second tube 1000 is predominantly longitudinally cylindrical and includes a smooth exterior circumferential surface 1006 that has a relatively constant diameter along the vast majority of the length of the second tube, but for the distal end 1008. An interior of the second tube 1000 is hollow to define a cylindrical through opening having a proximal orifice 1010 and a distal orifice 1012. The proximal orifice 1010 provides access to a cylindrical cavity partially defined by interior circumferential smooth wall 1016 having a diameter large enough to accommodate insertion of the distal end 826 of the ratchet tube 804.

The longitudinal profile of the second tube 1000 is substantially constant until it changes when approximately reaching the distal end 1008. Proximate the distal end 1008, the interior circumferential wall 1016 terminates at an internal, ring-shaped flange 1018 operative to change the cross-section of the cavity. In particular, the flange 1018 includes a central threaded cavity that feeds into a cylindrical cavity having a diameter less than that of the distal end 826 of the ratchet tube 804 to prohibit throughput of the ratchet tube beyond the flange. This smaller diameter cylindrical cavity is partially defined by a threaded circumferential surface 1022 that is adapted to engage a threaded adapter 1024 that is configured to mount to a ball 1026.

Figure 50:
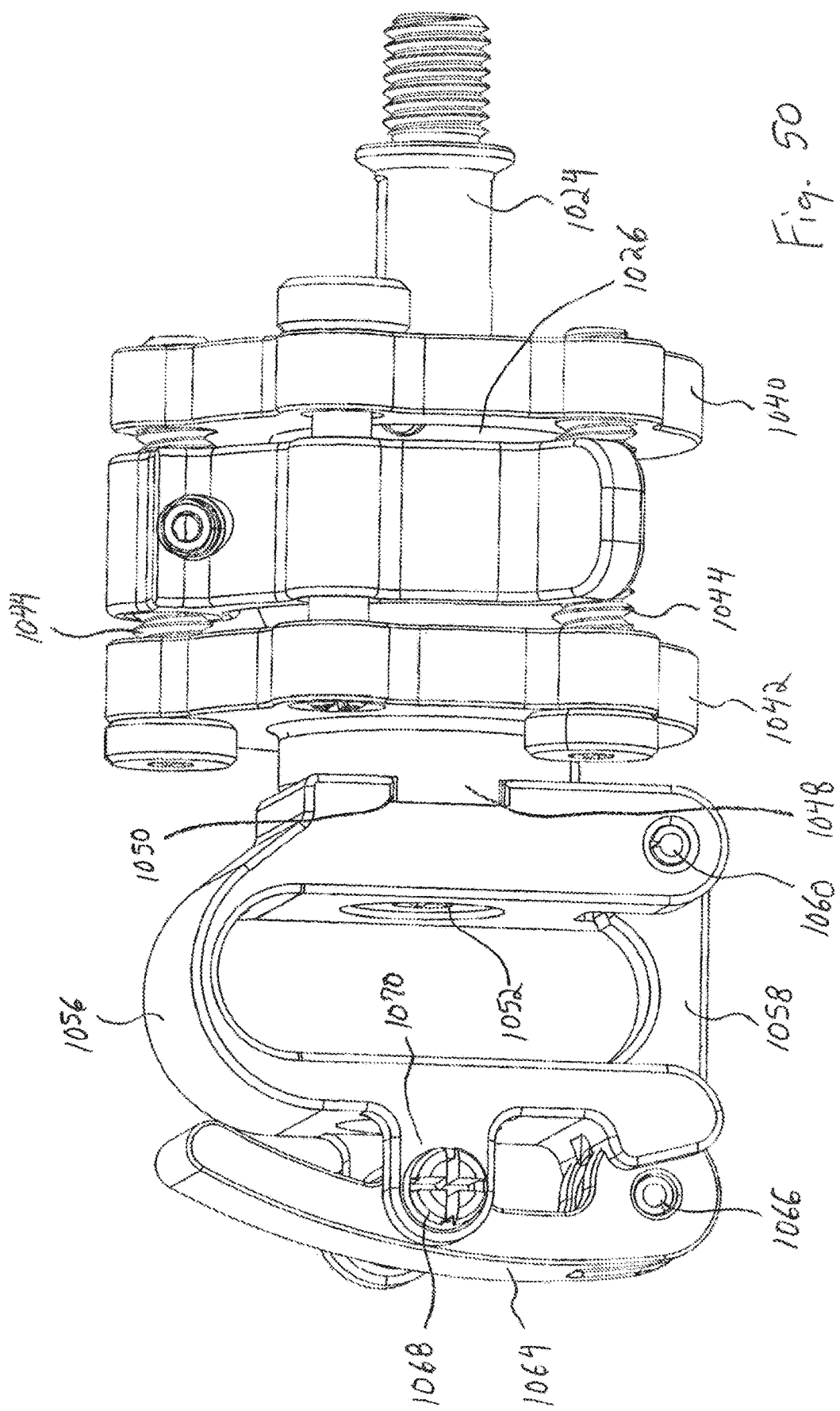
FIG. 50 is an elevated perspective view of the exemplary clamp and halo subassemblies shown in FIG. 35.

Referring to FIG. 50, the ball 1026 is concurrently mounted to the threaded adapter 1024 and to a distal assembly that includes a halo subassembly 1032 and a clamp subassembly 1034. The halo subassembly includes complementary halo frames 1040, 1042 that include a central opening therethrough. The first halo frame 1040 includes a plurality of smooth bore orifices that are each adapted to receive a threaded fastener 1044, while the second halo frame 1042 includes a plurality of threaded orifices that threadably engage the threaded fasteners, thereby coupling the frames together. Each frame 1040, 1042 also includes an arcuate interior surface adapted to match the contour of the ball 1026, thereby allowing the frames 1040, 1042 to be rotationally and axially repositionable about the ball 1026 when the threaded fasteners 1044 do not operate to compress the ball 1026 between the frames. An end of the halo subassembly 1032, opposite the threaded adapter 1024, includes a key 1048 that is received within a keyway 1050 of the clamp subassembly 1034. Likewise, a threaded fastener 1052 extends into the keyway 1050 and into the key 1048 as a means to couple the halo subassembly 1032 to the clamp subassembly 1034.

The clamp subassembly 1034 includes a U-shaped housing 1056 that is pivotally coupled to a repositionable gate 1058 via a pivot pin 1060 concurrently extending through orifices in the housing and gate. An opposite end of the gate 1058 is configured to be received in between a slit formed into the housing 1056 and be pivotally coupled to a handle 1064 via a pivot pin 1066. The handle 1064 also includes a through opening that is configured to receive a retainer 1068 that is concurrently received within a clevis 1070 of the housing 1056 in order to maintain the handle in position and maintain the gate 1058 in its closed position. Conversely, the retainer 1068 may be removed from the handle 1064 and clevis 1070, thereby allowing the handle to pivot and likewise the gate 1058 to pivot about the pin 1060 and open the gate.

It should also be noted that the opposite end (proximal end) of the ratcheting strut 800 also includes a ball 1026 concurrently mounted to a threaded adapter 1024 and to a halo subassembly 1032 and a clamp subassembly 1034. Other than orientation, the ball 1026, threaded adapter 1024, halo subassembly 1032, and clamp subassembly 1034 at the proximal end of the ratcheting strut 800 have identical structures to those aspects discussed with respect to the distal end. Consequently, a detailed discussion of these proximal components has been omitted in furtherance of brevity.

Figure 51:
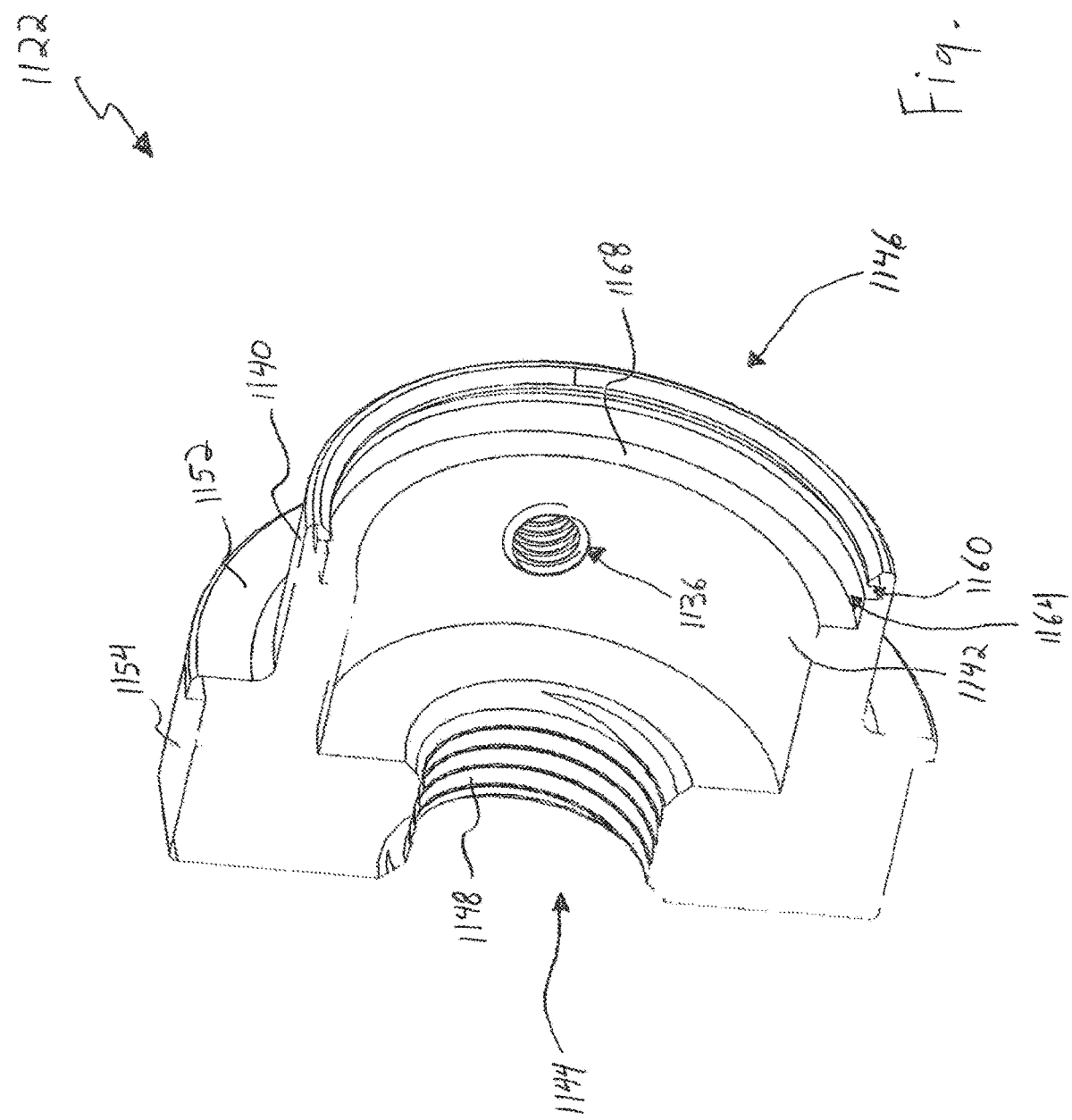
FIG. 51 is a cross-sectional view of the exemplary nut shown in FIG. 35, taken vertically and along the longitudinal axis.
Figure 52:
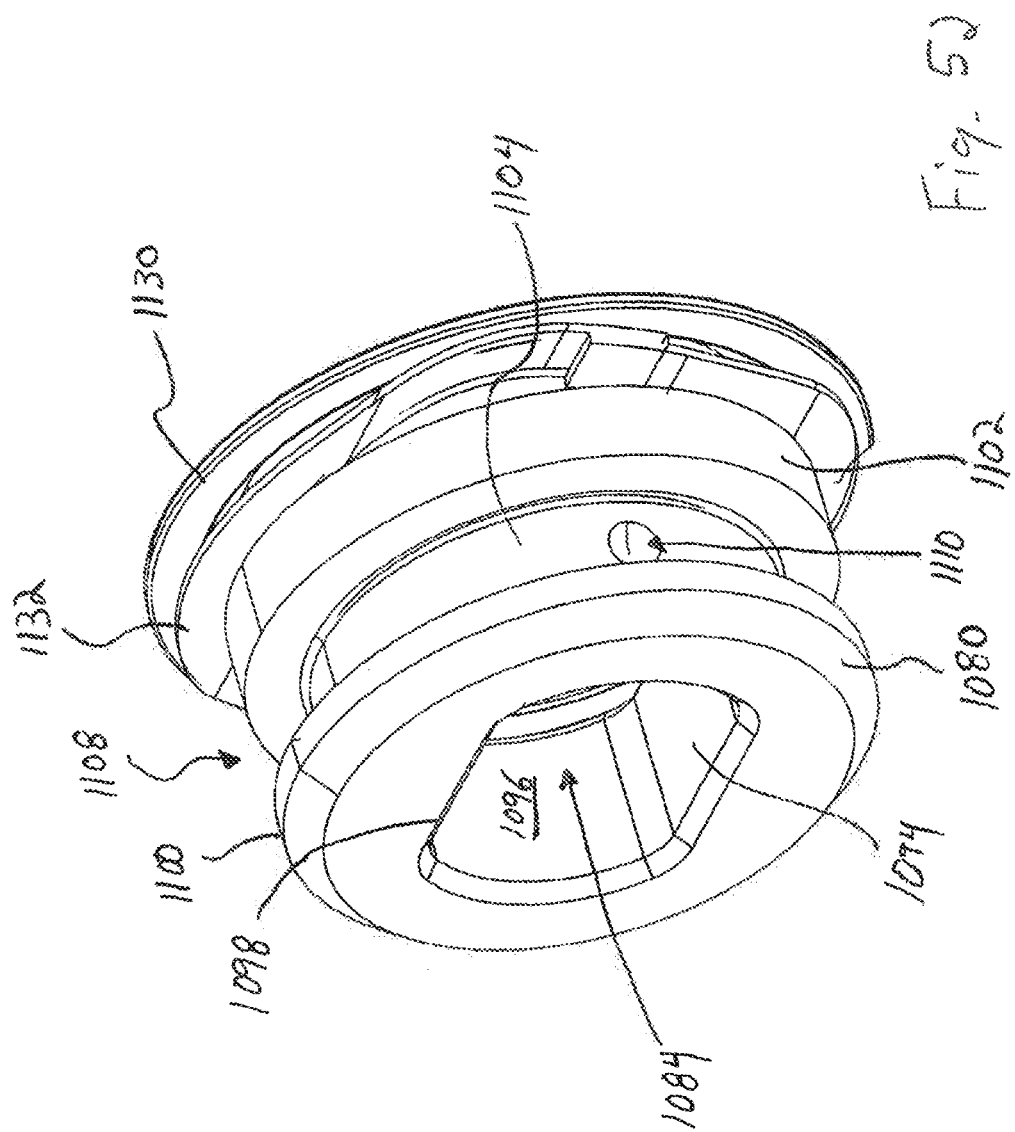
FIG. 52 is an elevated perspective view from a proximal side of the exemplary tube mount and washers as utilized in the exemplary ratcheting strut of FIG. 35.
Figure 53:
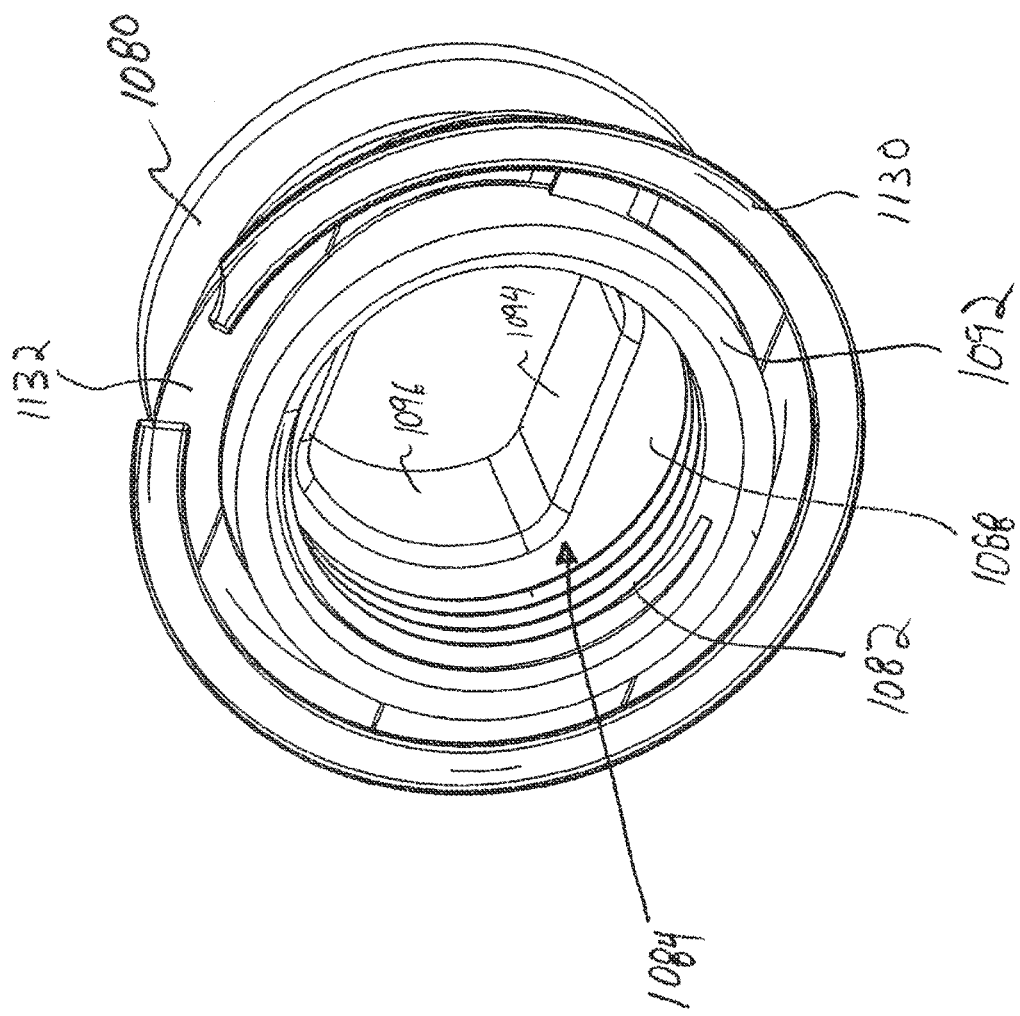
FIG. 53 is an elevated perspective view from a proximal side of the exemplary tube mount and washers as utilized in the exemplary ratcheting strut of FIG. 35.

Referring to FIGS. 51-53, a tube mount 1080 is coupled to the proximal end 828 of the ratchet tube 804 via a friction fit using a threaded engagement between the threads 830 on the proximal end of the ratchet tube and threads 1082 on the interior of the tube mount. It should be understood, however, that other means of attachment may be used such as, without limitation, adhesives, set screws, and welds. In this manner, longitudinal motion of the ratchet tube 804 results in corresponding longitudinal motion of the tube mount 1080 and vice versa. The tube mount 1080 includes a through opening 1084 that accommodates longitudinal movement of a threaded post 1090 independent of movement of the tube mount. A distal end 1092 of the tube mount includes a cylindrical collar that circumscribes the proximal end 828 of the ratchet tube 804. On the interior of this collar is a flange 1088 that provides an abutment surface against which the exposed proximal end 828 of the ratchet tube 804 contacts when fully seated within the collar. The flange 1088 also operates to change the profile of the through opening 1084 from circular along the collar to a narrower hybrid profile. This hybrid profile is defined by a pair of parallel, planar surfaces 1094 bridged by a pair of arcuate surfaces 1096 that extend longitudinally along a sleeve 1098 integrally formed with the flange 1088 and cellar. An exterior surface of the tube mount 1080 includes a pair of circumferential rings 1100, 1102 that cooperate with a smooth circumferential surface 1104 to delineate a circumferential trench 1108. Extending through the circumferential surface 1104 is a pair of through holes 1110 each adapted to partially receive a set screw 1120 mounted to a nut 1122 that is selectively rotationally repositionable with respect to the tube mount 1080. On the other side of the central ring 1102, nearer the distal end 1092, a discontinuous flat washer 1130 and a wave washer 1132 circumscribe the tube mount 1080, with the wave washer being nearer the proximal end.

In exemplary form, the nut 1122 circumscribes a proximal portion of the tube mount 1080 and is selectively rotationally repositionable with respect to the tube mount. The nut 1122 also includes one or more set screw orifices 1136 extending from a cylindrical exterior surface 1140 into an interior cylindrical surface 1142. The nut 1122 also includes proximal and distal openings 1144, 1146, where the proximal opening includes helical threads 1148 configured to engage corresponding threads 1150 on the exterior of the threaded post 1090 (see FIG. 53). Adjacent the exterior surface 1140 is a perpendicular flange 1152 interposing a hexagonal surface pattern 1154 to facilitate grasping of the nut 1122 and rotation of the nut with respect to the tube mount 1080. In this exemplary embodiment, the distal opening 1146 allows access to a cylindrical cavity defined by interior cylindrical surface 1142 in addition to access to a circumferential channel 1160 that receives the discontinuous flat washer 1130. In set proximally from the circumferential channel is a second circumferential channel 1164 partially delineated by the discontinuous flat washer 1130 and an internal flange 1168. The second circumferential channel 1164 is configured to receive the wave washer 1132 in order to couple the tube mount 1080 to the nut 1122, but at the same time allow rotational repositioning of the nut with respect to the tube mount. In order to retard rotation of the nut 1122 with respect to the tube mount 1080, a user may insert one or more set screws 1120 through the holes 1136 tighten the set screws against the smooth circumferential surface 1104 of the tube mount. For example, one may rotate the nut 1122 with respect to the tube mount 1080 in order to change the longitudinal position of the threaded post 1090 with respect to the nut and the tube mount, in addition to changing the position of the threaded post with respect to the ratchet tube 804.

Figure 54:
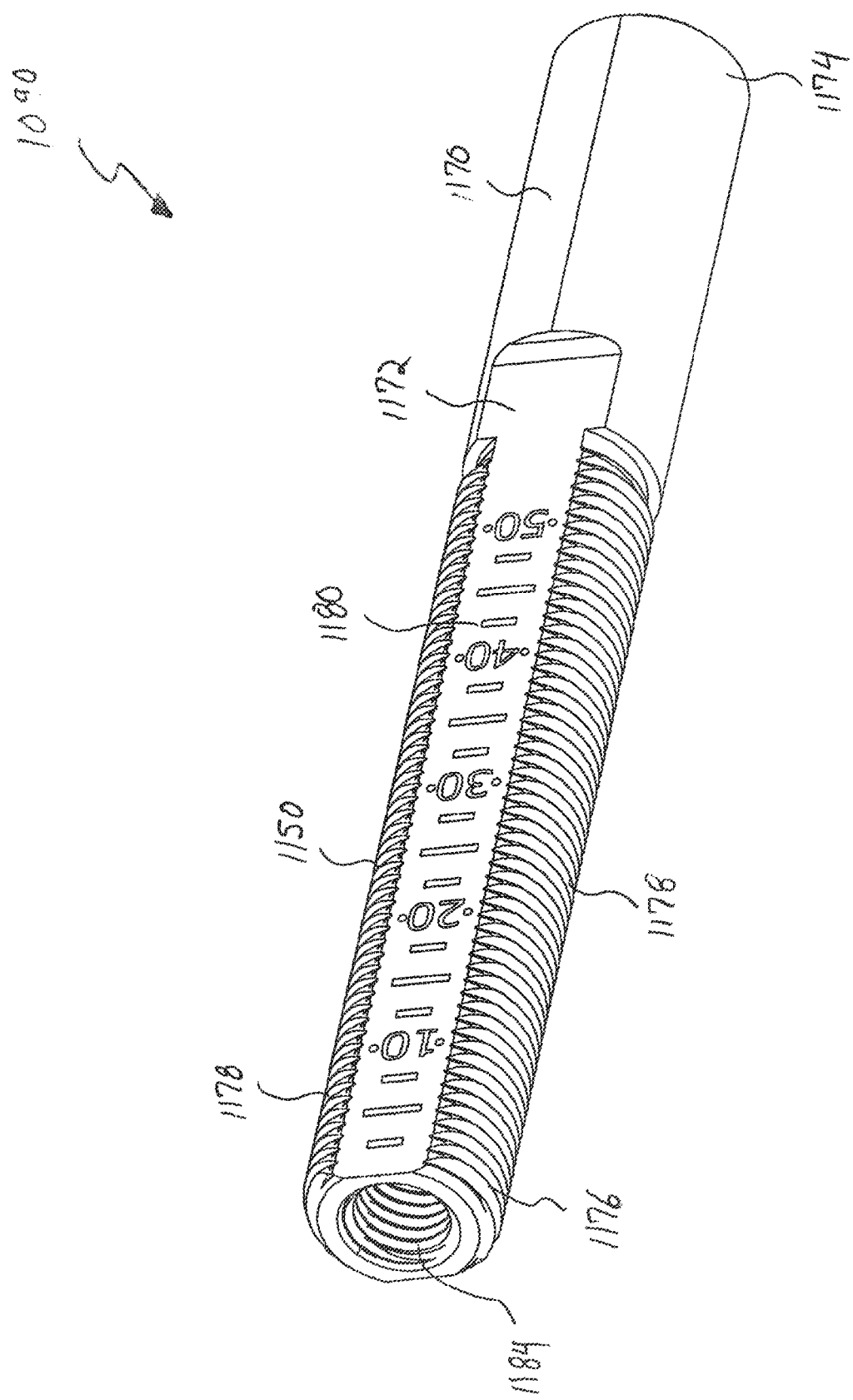
FIG. 54 is an elevated perspective view of the threaded post as shown in FIG. 35.

By way of example as shown in FIG. 54, the threaded post 1090 comprises a cylinder having a cylindrical exterior surface 1170, as well as a pair of planar surfaces 1172 extending longitudinally along a majority of the longitudinal length of the threaded post. In exemplary form, these planar surfaces 1172 may be formed by planarizing opposing sides of the cylinder to remove material from the exterior, thereby decreasing the thickness of the cylinder at certain circumferential locations. And the material removed from the cylinder can be cross-sectionally represented as a first area outlined by a first chord extending between circumferential exterior points at zero degrees and ninety degrees and by the circumferential surface extending between the same points at zero degrees and ninety degrees. Similarly, the second area may be outlined by a second chord extending between one hundred eighty degrees and two hundred seventy degrees and by the circumferential surface extending between the same points at one hundred eighty degrees and two hundred seventy degrees. The planar surfaces 1172, in exemplary form, do not extend along the entire longitudinal length of the threaded post 1090 so that a distal end 1174 of the threaded post retains a cylindrical shape, while the opposing proximal end 1176 of the threaded post is partially cylindrical. In this exemplary embodiment, the planar surfaces 1172 may include measurement indicia 1180 indicative of length increments. Nevertheless, other forms of indicia may also be used that may not necessarily be indicative of increments of length. More specifically, a pair of cylindrical surfaces 1178 extends between the planar surfaces 1172 to partially define the exterior of the threaded post 1090. Each cylindrical surface 1178 is separated from the other cylindrical surface by approximately ninety rotational degrees, except for the distal end where the cylindrical surfaces seamlessly intersect with the cylindrical exterior surface 1170. Both cylindrical surfaces 1178 are tapped along a predetermined length that extends to the proximal end 1176 to provide a series of repeating, partial threads 1150. It is these partial threads 1150 that are adapted to engage the threads 1148 of the nut 1122 so that rotational repositioning of the nut results in longitudinal repositioning of the threaded post 1090. More specifically, clockwise rotation of the nut 1122 may reposition the threaded post 1090 longitudinally in a distal direction, while counter-clockwise rotation of the nut 1122 may reposition the threaded post 1090 longitudinally in a proximal direction, or vice versa. The proximal end 1176 of the threaded post 1090 includes a cylindrical cavity that is tapped to provide internal threads 1184. These threads 1184 are adapted to be engaged by the threads of a threaded adapter 1024.

Referring back to FIGS. 35-37, in operation, the exemplary ratcheting strut 800 may be utilized to change the longitudinal length between opposing assemblies 1032. More specifically, by using the exemplary ratcheting strut 800, a user may quickly increase or decrease the longitudinal spacing between opposing ends of the device, while at the same time have the flexibility to vary the spacing in nearly infinite increments. In order to more quickly increase the spacing, a user may use the ratcheting feature of the ratchet tube 80 and reposition the tube proximally (away from the distal end 1008 of the second tube 1000) causing the inclined surfaces 846, 896 of the teeth 838, 892 to slide against one another. This proximal repositioning may be accomplished manually or by positioning a driver (not shown) within a gear shaft orifice 942 followed by rotation of the driver to rotate the gear shaft and gear 974 to reposition the ratchet tube 804 proximally. Likewise, the user may pivot the lever 870 using the button 912 in order to move the teeth 892 of the lever out of the line of travel of the teeth 838 of the ratchet tube, thereby allowing the user free movement of the ratchet tube in either the proximal or distal direction. This proximal or distal repositioning may be accomplished manually or by positioning a driver (not shown) within a gear shaft orifice 942 followed by rotation of the driver to rotate the gear shaft and gear 974 to reposition the ratchet tube 804 in either direction. In order to fine tune the spacing or add additional spacing beyond what is possible by extending the ratchet tube 804, a user may then rotate the nut 1122 in a counter clockwise direct to extend the threaded post 1090 longitudinally in the proximal direction until the desired length is reached. Conversely, the user may reduce the spacing by rotating the nut 1122 in a clockwise direct to retract the threaded post 1090 longitudinally in the distal direction until the desired length is reached. Accordingly, larger lengthwise adjustments may be made by repositioning the ratchet tube, whereas smaller lengthwise adjustments may be made by repositioning the threaded post 1090.

Following from the above description and invention summaries, it should be apparent to those of ordinary skill in the art that, while the methods and apparatuses herein described constitute exemplary embodiments of the present invention, the invention is not limited to the foregoing and changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A ratcheting strut comprising:
   a ratchet box defining a through passage, the through passage including a planar wall, a cylindrical interior wall, and a distal flange located in between the planar wall and the cylindrical interior wall;
   a first tube sized to extend at least partially through the passage, the first tube including teeth configured to engage corresponding teeth associated with the ratchet box and at least one planar surface sized to rest against the planar wall of the ratchet box to limit rotation of the first tube;
   a threaded rod operatively coupled to a first spherical element, the threaded rod repositionably mounted to the first tube; and
   a second tube having a first end and a second end, the first end resting against the distal flange when the second tube is mounted to the ratchet box, the second tube operatively coupled to a second spherical element.

2. The ratcheting strut of claim 1, wherein the first tube, the second tube, and the threaded rod are coaxial.

3. The ratcheting strut of claim 1, wherein the second tube includes a fixed length and is removably coupled to the ratchet box.

4. The ratcheting strut of claim 1, wherein the second spherical element is removably mounted to the second tube.

5. The ratcheting strut of claim 1, wherein the ratchet box includes a first lever repositionable between an engaged position and a disengaged position, the teeth associated with the ratchet box located on the first lever and configured to engage the teeth of the first tube in the engaged position and to disengage the teeth of the first tube in the disengaged position.

6. The ratcheting strut of claim 5, wherein the first lever is biased towards the engaged position.

7. The ratcheting strut of claim 1, wherein the second tube defines a first cavity sized to receive a portion of the first tube and the first tube defines a second cavity sized to receive a portion of the threaded rod.

8. The ratcheting strut of claim 7, wherein the first tube, the second tube, and the threaded rod telescopically interact with one another.

9. The ratcheting strut of claim 8, wherein, the first tube is operatively coupled to a tube mount having a tube mount orifice, the tube mount operatively coupled to a nut, the tube mount orifice sized to allow throughput of the threaded rod and disallow throughput of the first tube, the threaded rod configured to engage the nut so that rotation of the nut results in longitudinal repositioning of the threaded rod with respect to the nut, the first tube, and the tube mount.

10. The ratcheting strut of claim 1, wherein the ratchet box includes a repositionable button operatively coupled to a ratchet arm configured to engage the first tube.

11. A ratcheting strut comprising:
    a ratchet box including a through passage, the through passage including a first planar wall, a second planar wall, and a distal flange connecting a first end of the first planar wall to a first end of the second planar wall;
    a first tube sized to extend at least partially through the passage, the first tube including teeth configured to engage corresponding teeth associated with the ratchet box and a pair of planar surfaces sized to rest against the first and second planar walls to limit rotation of the first tube;
    a threaded rod operatively coupled to a first spherical element, the threaded rod repositionably mounted to the first tube; and
    a second tube having a first end and a second end, the first end resting against the distal flange when the second tube is removably coupled to the ratchet box in parallel with the first tube, the second tube operatively coupled to a second spherical element, the second tube includes a fixed length, wherein the first tube, the second tube, and the threaded rod are coaxial.

12. The ratcheting strut of claim 11, wherein the ratchet box includes a first lever repositionable between an engaged position and a disengaged position, the teeth associated with the ratchet box located on the first lever and configured to engage the teeth of the first tube in the engaged position and to disengage the teeth of the first tube in the disengaged position, and wherein the first lever is biased towards the engaged position.

13. The ratcheting strut of claim 11, wherein the ratchet box includes a repositionable button operatively coupled to a ratchet arm configured to engage the first tube.

14. The ratcheting strut of claim 11, wherein the second spherical element is removably mounted to the second tube.

15. The ratcheting strut of claim 11, wherein the second tube defines a first cavity sized to receive a portion of the first tube and the first tube defines a second cavity sized to receive a portion of the threaded rod, wherein the first tube, the second tube, and the threaded rod telescopically interact with one another, and wherein the first tube is operatively coupled to a tube mount having a tube mount orifice, the tube mount operatively coupled to a nut, the tube mount orifice sized to allow throughput of the threaded rod and disallow throughput of the first tube, the threaded rod configured to engage the nut so that rotation of the nut results in longitudinal repositioning of the threaded rod with respect to the nut, the first tube, and the tube mount.

* * * * *